(12) United States Patent
Huang et al.

(10) Patent No.: US 9,765,146 B2
(45) Date of Patent: Sep. 19, 2017

(54) FULLY HUMAN ANTI-CXC CHEMOKINE RECEPTOR 5 (CXCR5) ANTIBODIES

(71) Applicant: Sorrento Therapeutics, Inc., San Diego, CA (US)

(72) Inventors: Dingqiu Huang, San Diego, CA (US); Barbara A. Swanson, Encinitas, CA (US); Heyue Zhou, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 14/825,144

(22) Filed: Aug. 12, 2015

(65) Prior Publication Data
US 2016/0053014 A1 Feb. 25, 2016

Related U.S. Application Data

(60) Provisional application No. 62/041,017, filed on Aug. 22, 2014.

(51) Int. Cl.
*C07K 16/28* (2006.01)

(52) U.S. Cl.
CPC ...... *C07K 16/2866* (2013.01); *C07K 2317/21* (2013.01); *C07K 2317/76* (2013.01); *C07K 2317/92* (2013.01)

(58) Field of Classification Search
CPC ............ C07K 16/2866; C07K 2317/92; C07K 2317/21; C07K 2317/55; C07K 2317/622
See application file for complete search history.

(56) References Cited

U.S. PATENT DOCUMENTS

| 8,263,073 B2 | 9/2012 | Korman et al. |
| 2005/0180977 A1 | 8/2005 | Nixon et al. |
| 2007/0004910 A1 | 1/2007 | Sexton et al. |
| 2008/0267974 A1 | 10/2008 | Smith et al. |
| 2010/0196265 A1 | 8/2010 | Adams et al. |
| 2013/0209481 A1 | 8/2013 | Zhou et al. |

FOREIGN PATENT DOCUMENTS

WO 2012/010582 A1 1/2012

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
International Search Report and Written Opinion for International Application No. PCT/US2015/044926, dated Jan. 7, 2016.

* cited by examiner

*Primary Examiner* — Robert Landsman
(74) *Attorney, Agent, or Firm* — McCarter & English, LLP

(57) ABSTRACT

There is disclosed compositions and methods relating to or derived from anti-CXCR5 antibodies. More specifically, there is disclosed fully human antibodies that bind CXCR5, CXCR5-binding fragments and derivatives of such antibodies, and CXCR5-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having CXCR5 related disorders or conditions, including various inflammatory disorders and various cancers.

19 Claims, 1 Drawing Sheet

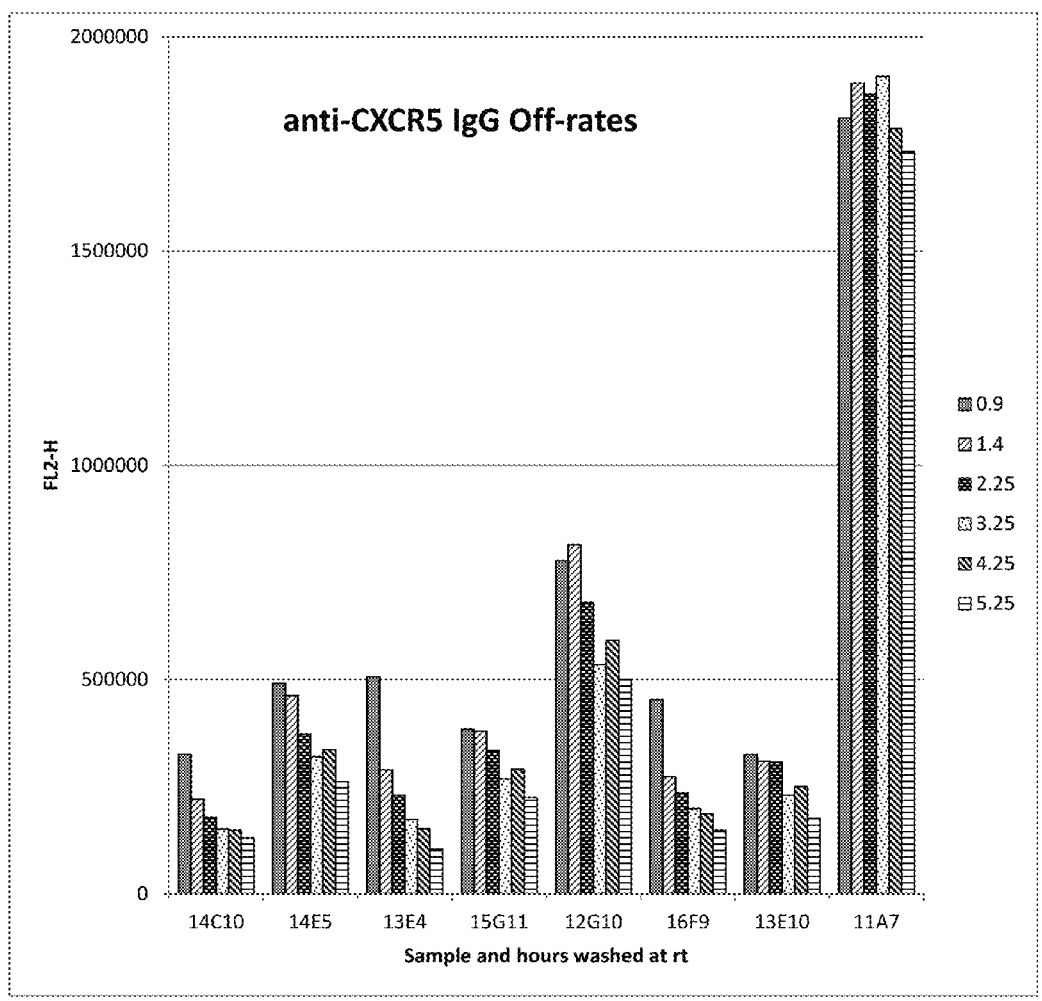

SEQUENCE LISTING

<160> NUMBER OF SEQ ID NOS: 202

<210> SEQ ID NO 1
<211> LENGTH: 119
<212> TYPE: PRT
<213> ORGANISM: Homo Sapiens

<400> SEQUENCE: 1

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Pro Phe Tyr Ser Ser Ser Asp Tyr Trp Gly Gln Gly
            100                 105                 110

Thr Leu Val Thr Val Ser Ser
        115

```
<210> SEQ ID NO 2
<211> LENGTH: 110
<212> TYPE: PRT
<213> ORGANISM: Homo Sapiens

<400> SEQUENCE: 2

Gln Ser Val Val Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Ser
                20                  25                  30

Lys Tyr Val Ser Trp Phe Gln Gln His Pro Gly Lys Ala Pro Lys Leu
            35                  40                  45

Met Ile Tyr Asp Val Ser Asn Arg Pro Ser Gly Val Tyr Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Thr Ser Ser
                85                  90                  95

Arg Thr Trp Val Phe Gly Gly Gly Thr Lys Leu Thr Val Leu
            100                 105                 110

<210> SEQ ID NO 3
<211> LENGTH: 113
<212> TYPE: PRT
<213> ORGANISM: Homo Sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Val
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Asp Tyr Trp Gly Gln Gly Thr Leu Val Thr Val Ser
            100                 105                 110

Ser

<210> SEQ ID NO 4
<211> LENGTH: 110
<212> TYPE: PRT
<213> ORGANISM: Homo Sapiens

<400> SEQUENCE: 4

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60
```

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Pro Val Phe Gly Gly Gly Thr Gln Leu Thr Val Leu
            100                 105                 110

<210> SEQ ID NO 5
<211> LENGTH: 112
<212> TYPE: PRT
<213> ORGANISM: Homo Sapiens

<400> SEQUENCE: 5

Glu Val Gln Leu Leu Glu Ser Gly Gly Gly Leu Val Gln Pro Gly Gly
 1               5                  10                  15

Ser Leu Arg Leu Ser Cys Ala Gly Ser Glu Ser Thr Phe Gly Asp Ser
             20                  25                  30

Trp Leu Asn Trp Val Arg Gln Ala Pro Gly Lys Gly Leu Glu Trp Val
         35                  40                  45

Ala Asn Ile Asn Lys Asp Gly Ser Lys Lys Glu Tyr Val Glu Ser Val
 50                  55                  60

Lys Gly Arg Phe Thr Ile Ser Arg Asp Asn Ala Lys Lys Ser Val Tyr
 65                  70                  75                  80

Leu Gln Met Asn Ser Leu Arg Val Glu Asp Thr Ala Val Tyr Tyr Cys
                 85                  90                  95

Leu Leu Lys Gly Val Trp Gly Gln Gly Thr Leu Val Thr Val Ser Ser
            100                 105                 110

<210> SEQ ID NO 6
<211> LENGTH: 107
<212> TYPE: PRT
<213> ORGANISM: Homo Sapiens

<400> SEQUENCE: 6

Ala Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Ile
                 85                  90                  95

Thr Phe Gly Pro Gly Thr Lys Val Asp Ile Lys
            100                 105

<210> SEQ ID NO 7
<211> LENGTH: 115
<212> TYPE: PRT
<213> ORGANISM: Homo Sapiens

<400> SEQUENCE: 7

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Tyr
```

```
                20                  25                  30
Ala Met His Trp Val Arg Gln Ala Pro Gly Lys Gly Leu Gln Trp Val
            35                  40                  45
Ala Val Ile Ser His Asp Gly Ser Ala Lys Tyr Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Ser Arg Trp Gly Asp Asn Trp Gly Gln Gly Thr Leu Val Thr
            100                 105                 110
Val Ser Ser
        115

<210> SEQ ID NO 8
<211> LENGTH: 111
<212> TYPE: PRT
<213> ORGANISM: Homo Sapiens

<400> SEQUENCE: 8

Ser Tyr Glu Leu Met Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
        35                  40                  45
Met Ile Tyr Asp Val Ser Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
                85                  90                  95
Ser Thr Pro Tyr Val Phe Gly Thr Gly Thr Lys Leu Thr Val Leu
            100                 105                 110

<210> SEQ ID NO 9
<211> LENGTH: 115
<212> TYPE: PRT
<213> ORGANISM: Homo Sapiens

<400> SEQUENCE: 9

Glu Val Gln Leu Leu Glu Ser Gly Gly Gly Leu Val Gln Pro Gly Arg
1               5                   10                  15
Ser Leu Arg Leu Ser Cys Ala Ala Ser Gly Phe Asn Phe Asp Ala Tyr
            20                  25                  30
Ala Met His Trp Val Arg Gln Ala Pro Gly Lys Gly Leu Glu Trp Val
        35                  40                  45
Ser Gly Ile Ser Trp Asn Ser Gly Tyr Ile Ala Tyr Ala Asp Ser Val
    50                  55                  60
Glu Gly Arg Phe Ala Ile Ser Arg Asp Asn Ser Lys Asn Thr Val Phe
65                  70                  75                  80
Leu Gln Met Asn Ser Leu Arg Ala Glu Asp Thr Ala Ile Tyr Tyr Cys
                85                  90                  95
Ala Arg Asp Arg Trp Leu Ser Tyr Trp Gly Gln Gly Thr Leu Val Thr
            100                 105                 110
Val Ser Ser
```

-continued

```
        115

<210> SEQ ID NO 10
<211> LENGTH: 110
<212> TYPE: PRT
<213> ORGANISM: Homo Sapiens

<400> SEQUENCE: 10

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Phe Val Phe Gly Gly Gly Thr Lys Leu Thr Val Leu
            100                 105                 110

<210> SEQ ID NO 11
<211> LENGTH: 120
<212> TYPE: PRT
<213> ORGANISM: Homo Sapiens

<400> SEQUENCE: 11

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Ile Thr Thr His
            20                  25                  30

Tyr Ile His Trp Val Arg Gln Ala Pro Gly Gln Gly Leu Glu Trp Met
        35                  40                  45

Gly Ile Ile Asn Pro Asn Ser Gly Arg Thr Lys Tyr Pro Gln Lys Phe
50                  55                  60

Gln Gly Arg Val Thr Met Thr Arg Asp Thr Ser Thr Asn Thr Val Tyr
65                  70                  75                  80

Met Glu Val Asn Ser Leu Arg Ser Glu Asp Thr Ala Val Tyr Tyr Cys
                85                  90                  95

Ala Thr Gly Ser Gly Ser Tyr Gly Asn Trp Phe Asp Pro Trp Gly Gln
            100                 105                 110

Gly Thr Leu Val Thr Val Ser Ser
        115                 120

<210> SEQ ID NO 12
<211> LENGTH: 139
<212> TYPE: PRT
<213> ORGANISM: Homo Sapiens

<400> SEQUENCE: 12

Gln Thr Val Val Thr Gln Pro Pro Ser Val Ser Gly Ala Pro Gly Gln
1               5                   10                  15

Arg Val Thr Val Ser Cys Thr Gly Ser Ser Ser Asn Ile Gly Ser Val
            20                  25                  30

Val Thr Gln Pro Pro Ser Val Ser Ala Ala Pro Gly Gln Lys Val Thr
        35                  40                  45
```

```
Ile Ser Cys Ser Gly Ser Ser Asn Ile Gly Asn Asn Tyr Val Ser
    50                  55                  60

Trp Tyr Gln Gln Leu Pro Gly Thr Ala Pro Lys Leu Leu Ile Tyr Asp
 65                  70                  75                  80

Asn Asn Lys Arg Pro Ser Gly Ile Pro Asp Arg Phe Ser Gly Ser Lys
                 85                  90                  95

Ser Gly Thr Ser Ala Thr Leu Gly Ile Thr Gly Leu Gln Thr Gly Asp
            100                 105                 110

Glu Ala Asp Tyr Tyr Cys Gly Thr Trp Asp Ser Ser Leu Thr Leu Tyr
            115                 120                 125

Val Phe Gly Thr Gly Thr Lys Leu Thr Val Leu
            130                 135
```

<210> SEQ ID NO 13
<211> LENGTH: 119
<212> TYPE: PRT
<213> ORGANISM: Homo Sapiens

<400> SEQUENCE: 13

```
Gln Val Gln Leu Val Gln Ser Gly Gly Glu Val Lys Lys Pro Gly Ala
 1               5                  10                  15

Leu Val Lys Val Ser Cys Lys Ala Ser Gly Tyr Thr Phe Ser Thr His
             20                  25                  30

Gly Ile Ser Trp Val Arg Gln Ala Pro Gly Gln Gly Leu Ala Trp Met
         35                  40                  45

Gly Trp Ile Ser Ala Tyr Asn Gly Lys Ala Thr Tyr Ala Gln Thr Phe
 50                  55                  60

Gln Gly Arg Val Thr Met Thr Thr Asp Thr Ser Thr Asn Thr Ala Tyr
 65                  70                  75                  80

Met Glu Leu Arg Asn Leu Arg Ser Asp Asp Thr Ala Val Tyr Tyr Cys
             85                  90                  95

Ala Arg Val Gly Ala Val Thr Gly Met Asp Ser Trp Gly Gln Gly Thr
        100                 105                 110

Leu Val Thr Val Ser Ser Ser
        115
```

<210> SEQ ID NO 14
<211> LENGTH: 110
<212> TYPE: PRT
<213> ORGANISM: Homo Sapiens

<400> SEQUENCE: 14

```
Gln Ser Val Val Thr Gln Pro Pro Ser Val Ser Ala Ala Pro Gly Gln
 1               5                  10                  15

Thr Val Thr Ile Ser Cys Ser Gly Ser Ser Asn Ile Gly Ser Lys
             20                  25                  30

Phe Val Ser Trp Tyr Gln His Val Pro Gly Thr Ala Pro Lys Leu Leu
         35                  40                  45

Ile Tyr Asp Asn Asp Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
             85                  90                  95

Ser Ala Tyr Val Phe Gly Thr Gly Thr Lys Val Thr Val Leu
        100                 105                 110
```

<210> SEQ ID NO 15
<211> LENGTH: 120
<212> TYPE: PRT
<213> ORGANISM: Homo Sapiens

<400> SEQUENCE: 15

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Ser Arg Tyr
            20                  25                  30

Ala Met His Trp Val Arg Gln Ala Pro Gly Gln Arg Leu Glu Trp Met
        35                  40                  45

Gly Trp Ile His Ala Gly Asn Gly Asn Thr Lys Tyr Ser Gln Lys Phe
    50                  55                  60

Gln Gly Arg Val Thr Ile Ser Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Ile Ala Ala Ala Gly Gly Phe Asp Tyr Trp Gly Gln
            100                 105                 110

Gly Thr Leu Val Thr Val Ser Ser
        115                 120

<210> SEQ ID NO 16
<211> LENGTH: 110
<212> TYPE: PRT
<213> ORGANISM: Homo Sapiens

<400> SEQUENCE: 16

Gln Ala Val Leu Thr Gln Pro Pro Ser Ala Ser Gly Thr Pro Gly Gln
1               5                   10                  15

Arg Val Thr Leu Ser Cys Ser Gly Ser Ser Ser Asn Ile Gly Arg Asn
            20                  25                  30

Tyr Val Tyr Trp Tyr Gln Gln Leu Pro Gly Thr Ala Pro Lys Leu Val
        35                  40                  45

Leu Tyr Val Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Arg Ala Tyr Val Phe Gly Thr Gly Thr Lys Val Thr Val Leu
            100                 105                 110

<210> SEQ ID NO 17
<211> LENGTH: 115
<212> TYPE: PRT
<213> ORGANISM: Homo Sapiens

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Ala Asn Phe Asp Tyr Trp Gly Gln Gly Thr Leu Val Thr
               100                 105                 110

Val Ser Ser
        115

<210> SEQ ID NO 18
<211> LENGTH: 111
<212> TYPE: PRT
<213> ORGANISM: Homo Sapiens

<400> SEQUENCE: 18

Gln Ala Gly Leu Thr Gln Pro Pro Ser Ala Ser Gly Ser Pro Gly Gln
  1               5                  10                  15

Ser Val Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
                 35                  40                  45

Met Ile Tyr Glu Val Ser Lys Arg Pro Ser Gly Val Pro Asp Arg Phe
         50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Lys Gly Val Val Phe Gly Gly Gly Thr Lys Leu Thr Val Leu
                100                 105                 110

<210> SEQ ID NO 19
<211> LENGTH: 119
<212> TYPE: PRT
<213> ORGANISM: Homo Sapiens

<400> SEQUENCE: 19

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
                 35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Ser Gly Pro Thr Ala Lys Phe Asp Tyr Trp Gly Gln Gly
                100                 105                 110

Thr Leu Val Thr Val Ser Ser
                115

<210> SEQ ID NO 20
<211> LENGTH: 110
```

<212> TYPE: PRT
<213> ORGANISM: Homo Sapiens

<400> SEQUENCE: 20

Gln Ser Val Leu Thr Gln Pro Ala Ser Val Ser Gly Ser Pro Gly Gln
1               5                   10                  15

Ser Val Thr Ile Ser Cys Thr Gly Thr Ser Arg Asp Val Gly Gly Tyr
            20                  25                  30

Asn Phe Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Thr Gly Ser Lys Ser Gly Asn Thr Ala Ser Leu Thr Ile Ser Gly Leu
65                  70                  75                  80

Gln Ala Glu Asp Glu Ala Asp Tyr His Cys Ser Ser Tyr Arg Arg Gly
                85                  90                  95

Asp Thr Leu Val Phe Gly Gly Gly Thr Lys Leu Thr Val Leu
            100                 105                 110

<210> SEQ ID NO 21
<211> LENGTH: 124
<212> TYPE: PRT
<213> ORGANISM: Homo Sapiens

<400> SEQUENCE: 21

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Met
        35                  40                  45

Gly Ile Ile Asn Pro Ser Gly Gly Thr Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Asp Arg Arg Val Val Ala Ala Thr Thr Pro Ser Ala Phe Asp
            100                 105                 110

Val Trp Gly Gln Gly Thr Met Val Thr Val Ser Ser
            115                 120

<210> SEQ ID NO 22
<211> LENGTH: 110
<212> TYPE: PRT
<213> ORGANISM: Homo Sapiens

<400> SEQUENCE: 22

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Val Gly Leu Gln

```
                   65                  70                  75                  80
Thr Gly Asp Glu Ala Asp Tyr Tyr Cys Ala Thr Trp Asp Ser Leu
                85                  90                  95

Ser Thr Phe Leu Phe Gly Pro Gly Thr Lys Leu Thr Val Leu
                100                 105                 110

<210> SEQ ID NO 23
<211> LENGTH: 118
<212> TYPE: PRT
<213> ORGANISM: Homo Sapiens

<400> SEQUENCE: 23

Gln Met Gln Leu Val Gln Ser Gly Ser Glu Val Lys Lys Pro Gly Ala
1               5                   10                  15

Ser Val Lys Val Ser Cys Arg Ala Ser Gly Tyr Leu Phe Thr Asn Tyr
                20                  25                  30

Gly Ile Ser Trp Val Arg Gln Ala Pro Gly Gln Gly Leu Glu Trp Met
                35                  40                  45

Gly Trp Val Ser Ala His Gly Glu Phe Thr Lys Tyr Ala Pro Ser Leu
            50                  55                  60

Gln Asp Arg Val Thr Met Thr Ser Asp Ile Ser Thr Thr Thr Ala Tyr
65                  70                  75                  80

Met Glu Leu Arg Ser Leu Arg Ser Asp Thr Gly Val Tyr Tyr Cys
                85                  90                  95

Ala Arg Asp Arg Gly Ala Asp His Phe Asp Thr Trp Gly Gln Gly Thr
                100                 105                 110

Leu Val Thr Val Ser Ser
            115

<210> SEQ ID NO 24
<211> LENGTH: 112
<212> TYPE: PRT
<213> ORGANISM: Homo Sapiens

<400> SEQUENCE: 24

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Ser Trp Leu Gln Gln Arg Pro Gly Gln Pro
                35                  40                  45

Pro Arg Leu Leu Ile Tyr Lys Ile Ser Asn Arg Phe Ser Gly Val Pro
            50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro Phe Thr Phe Gly Gln Gly Thr Lys Leu Glu Ile Lys
                100                 105                 110

<210> SEQ ID NO 25
<211> LENGTH: 116
<212> TYPE: PRT
<213> ORGANISM: Homo Sapiens

<400> SEQUENCE: 25

Gln Val Gln Leu Gln Gln Ser Gly Pro Gly Leu Leu Asn Pro Ser Gln
1               5                   10                  15
```

```
Thr Leu Ser Leu Thr Cys Val Ile Ser Gly Asp Ser Val Ser Ser Asn
            20                  25                  30

Ser Ala Thr Trp Asn Trp Ile Arg Gln Ser Pro Ser Arg Gly Leu Glu
            35                  40                  45

Trp Leu Gly Arg Thr Tyr Tyr Arg Ser Gln Trp Phe Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Trp Leu His Val Trp Gly Gln Gly Thr Thr Val
            100                 105                 110

Thr Val Ser Ser
        115

<210> SEQ ID NO 26
<211> LENGTH: 109
<212> TYPE: PRT
<213> ORGANISM: Homo Sapiens

<400> SEQUENCE: 26

Leu Pro Val Leu Thr Gln Pro Pro Ser Ala Ser Gly Thr Pro Gly Gln
1               5                   10                  15

Arg Val Thr Ile Ser Cys Ser Gly Gly Thr Ser Asn Ile Gly Asn Asn
            20                  25                  30

Asn Val Tyr Trp Tyr Gln Gln Val Pro Gly Met Ala Pro Lys Leu Leu
            35                  40                  45

Ile Phe Arg Asn Ser Gln Arg Pro Ser Gly Val Pro Asp Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Gly Asp Tyr Tyr Cys Gly Ser Tyr Ala Gly Pro Arg
                85                  90                  95

Thr Tyr Val Phe Gly Ser Gly Thr Lys Val Thr Val Leu
            100                 105

<210> SEQ ID NO 27
<211> LENGTH: 115
<212> TYPE: PRT
<213> ORGANISM: Homo Sapiens

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Gly Gln Asn Leu Asp Tyr Trp Gly Gln Gly Thr Leu Val Thr
            100                 105                 110
```

```
Val Ser Ser
        115

<210> SEQ ID NO 28
<211> LENGTH: 110
<212> TYPE: PRT
<213> ORGANISM: Homo Sapiens

<400> SEQUENCE: 28

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Ile Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Ser
                85                  90                  95

Ser Thr Gln Val Phe Gly Gly Gly Thr Lys Leu Thr Val Leu
            100                 105                 110

<210> SEQ ID NO 29
<211> LENGTH: 125
<212> TYPE: PRT
<213> ORGANISM: Homo Sapiens

<400> SEQUENCE: 29

Gln Met Gln Leu Val Gln Ser Gly Ala Val Val Lys Pro Pro Gly Ser
1               5                   10                  15

Ser Val Lys Val Ser Cys Lys Ala Ser Gly Gly Thr Ile Ser Arg Tyr
            20                  25                  30

Val Ile Ser Trp Val Arg Gln Ala Pro Gly Gln Arg Leu Glu Trp Met
        35                  40                  45

Gly Trp Ile Asn Ala Ala Asn Gly Arg Thr Lys Tyr Leu Asp Lys Phe
    50                  55                  60

Gln Gly Arg Val Thr Phe Thr Arg Asp Met Thr Ser Thr Ala Ser
65                  70                  75                  80

Met Glu Leu Ser Ser Leu Thr Ser Glu Asp Thr Ala Val Tyr Phe Cys
                85                  90                  95

Ala Arg Ser Leu Arg Glu Gln Val Gly Gly Asn Tyr Tyr Leu Met
            100                 105                 110

Asp Val Trp Gly Arg Gly Thr Thr Val Thr Val Ser Ser
        115                 120                 125

<210> SEQ ID NO 30
<211> LENGTH: 107
<212> TYPE: PRT
<213> ORGANISM: Homo Sapiens

<400> SEQUENCE: 30

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Thr Tyr
            20                  25                  30
```

```
Leu Ala Trp Phe Gln Gln Lys Pro Gly Lys Val Pro Lys Pro Leu Ile
            35                  40                  45

Tyr Ala Ala Ser Thr Leu Gln Ser Gly Val Pro Ser Arg Phe Ser Gly
     50                  55                  60

Ser Gly Ser Gly Ala Asp Phe Thr Leu Thr Ile Ser Ser Leu Gln Pro
 65                  70                  75                  80

Glu Asp Val Ala Thr Tyr Tyr Cys Gln Lys Tyr Asn Ser Val Pro Gln
                 85                  90                  95

Thr Phe Gly Gln Gly Thr Lys Val Glu Ile Lys
            100                 105
```

<210> SEQ ID NO 31
<211> LENGTH: 117
<212> TYPE: PRT
<213> ORGANISM: Homo Sapiens

<400> SEQUENCE: 31

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Gly Arg His Ser Gly Ser Tyr Leu Arg Gly Thr Leu
            100                 105                 110

Val Thr Val Ser Ser
        115
```

<210> SEQ ID NO 32
<211> LENGTH: 139
<212> TYPE: PRT
<213> ORGANISM: Homo Sapiens

<400> SEQUENCE: 32

```
Asn Phe Met Leu Thr Gln Pro Pro Ser Val Ser Lys Gly Leu Arg Gln
 1               5                  10                  15

Thr Ala Thr Leu Thr Cys Thr Gly Asn Ser Asn Asn Val Gln Ser Ala
                 20                  25                  30

Leu Thr Gln Pro Arg Ser Val Ser Gly Ser Pro Gly Gln Ser Val Thr
            35                  40                  45

Ile Ser Cys Thr Gly Thr Ser Ser Asp Val Gly Thr Tyr Asn Tyr Val
     50                  55                  60

Ser Trp Tyr Gln Gln His Pro Gly Lys Ala Pro Lys Leu Ile Ile Tyr
 65                  70                  75                  80

Asp Val Ser Ile Arg Pro Ser Gly Val Ser Asn Arg Phe Ser Gly Ser
                 85                  90                  95

Lys Ser Gly Asn Thr Ala Ser Leu Thr Ile Thr Gly Leu Gln Ala Glu
            100                 105                 110

Asp Glu Ala Asp Tyr Tyr Cys Gln Ser Tyr Asp Ser Ser Leu Ser Gly
     115                 120                 125
```

```
Val Phe Gly Gly Gly Thr Gln Leu Thr Val Leu
        130                 135

<210> SEQ ID NO 33
<211> LENGTH: 114
<212> TYPE: PRT
<213> ORGANISM: Homo Sapiens

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Leu Ser Asn Tyr
            20                  25                  30

Ala Ile His Trp Val Arg Gln Ala Pro Gly Gln Gly Leu Glu Trp Met
        35                  40                  45

Gly Trp Ile Asn Ala Val Asn Gly Asn Thr Lys Tyr Ser Gln Lys Phe
    50                  55                  60

Gln Gly Arg Val Thr Ala Thr Arg Asp Thr Ser Ala Thr Ile Phe Tyr
65                  70                  75                  80

Leu Glu Leu Ser Ser Leu Arg Ser Glu Asp Thr Ala Val Tyr Tyr Cys
                85                  90                  95

Val Leu Ile Thr Gly Ala Tyr Trp Gly Glu Gly Thr Thr Val Thr Val
            100                 105                 110

Ser Ser

<210> SEQ ID NO 34
<211> LENGTH: 110
<212> TYPE: PRT
<213> ORGANISM: Homo Sapiens

<400> SEQUENCE: 34

Leu Pro Val Leu Thr Gln Pro Pro Ser Ala Ser Gly Thr Pro Gly Gln
1               5                   10                  15

Arg Val Thr Ile Ser Cys Ser Gly Asn Val Ser Asn Ile Ala Asn Asn
            20                  25                  30

Tyr Val Tyr Trp Tyr Arg His Leu Pro Gly Thr Ala Pro Lys Leu Leu
        35                  40                  45

Met Tyr Arg Asn Asn Lys Arg Pro Ser Gly Val Pro Asp Arg Phe Thr
    50                  55                  60

Ala Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

His Gly Tyr Val Phe Gly Thr Gly Thr Lys Val Thr Val Leu
            100                 105                 110

<210> SEQ ID NO 35
<211> LENGTH: 118
<212> TYPE: PRT
<213> ORGANISM: Homo Sapiens

<400> SEQUENCE: 35

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Val Trp Val Arg Arg Ser Pro Gly Lys Gly Leu Glu Trp Ile
        35                  40                  45
```

```
Ser Tyr Ile Ser Ser Gly Gly Thr Ile Ile Tyr Ala Asp Ser Val
     50                  55                  60

Lys Gly Arg Phe Thr Ile Ser Arg His Asn Ser Glu Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Arg Ser Lys Gly His Ala Leu Asp Val Trp Gly Gln Gly Thr
            100                 105                 110

Thr Val Thr Val Ser Ser
            115
```

```
<210> SEQ ID NO 36
<211> LENGTH: 110
<212> TYPE: PRT
<213> ORGANISM: Homo Sapiens

<400> SEQUENCE: 36

Leu Pro Val Leu Thr Gln Ser Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
 65                  70                  75                  80

Pro Glu Asp Glu Ala Tyr Tyr Tyr Cys Ala Ser Trp Asp Asp Arg Leu
                 85                  90                  95

Thr Gly Tyr Val Phe Gly Ser Gly Thr Lys Val Thr Val Leu
            100                 105                 110
```

```
<210> SEQ ID NO 37
<211> LENGTH: 122
<212> TYPE: PRT
<213> ORGANISM: Homo Sapiens

<400> SEQUENCE: 37

Gln Val Gln Leu Val Glu Ser Gly Gly Gly Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Arg Ala Val Ala Gly His Tyr Tyr Gly Met Asp Val Trp
            100                 105                 110

Gly Gln Gly Thr Thr Val Thr Val Ser Ser
        115                 120
```

```
<210> SEQ ID NO 38
```

```
<211> LENGTH: 110
<212> TYPE: PRT
<213> ORGANISM: Homo Sapiens

<400> SEQUENCE: 38

Gln Ala Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Val Trp Leu Gln His Gln Gly His Pro Lys Phe Leu
        35                  40                  45

Ser Ser Arg Lys Asn Asn Arg Pro Ser Gly Ile Ser Glu Arg Phe Ser
50                  55                  60

Ala Ser Arg Ser Gly Asn Thr Ala Ser Leu Thr Ile Thr Gly Leu Gln
65                  70                  75                  80

Pro Asp Asp Glu Ala Asp Tyr Tyr Cys Ser Ala Trp Asp Ser Ser Leu
                85                  90                  95

Ser Ser Trp Val Phe Gly Gly Gly Thr Lys Leu Thr Val Leu
            100                 105                 110

<210> SEQ ID NO 39
<211> LENGTH: 119
<212> TYPE: PRT
<213> ORGANISM: Homo Sapiens

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ser Gly Ser Gly Phe Ser Phe Ser Asn Tyr
            20                  25                  30

Ala Met His Trp Val Arg Gln Ala Pro Gly Lys Gly Leu Glu His Val
        35                  40                  45

Ser Ala Ile Ser Ser Asn Gly Gly Ser Ile Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Phe Gln Met Ser Ser Leu Arg Thr Glu Asp Thr Ala Val Tyr Tyr Cys
                85                  90                  95

Val Lys Arg Val Pro Gly Thr Ser Asn Phe Asp Tyr Trp Gly Gln Gly
            100                 105                 110

Thr Leu Val Thr Val Ser Ser
        115

<210> SEQ ID NO 40
<211> LENGTH: 110
<212> TYPE: PRT
<213> ORGANISM: Homo Sapiens

<400> SEQUENCE: 40

Gln Pro Val Leu Thr Gln Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60
```

```
Gly Ser Lys Ser Gly Thr Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Arg Val Phe Gly Gly Gly Thr Lys Leu Thr Val Leu
                100                 105                 110

<210> SEQ ID NO 41
<211> LENGTH: 119
<212> TYPE: PRT
<213> ORGANISM: Homo Sapiens

<400> SEQUENCE: 41

Gln Val Gln Leu Val Glu Ser Gly Gly Gly Leu Val Gln Ser Gly Gly
 1               5                  10                  15

Ser Leu Arg Leu Ser Cys Ala Ala Ser Gly Phe Thr Phe Ser Ser Tyr
                20                  25                  30

Gly Met Gln Trp Val Arg Gln Ala Pro Gly Lys Gly Leu Glu Trp Val
             35                  40                  45

Ser Ser Ile Ser Ser Ser Gly Gly Ser Thr Tyr Ala Asp Ser Val
 50                  55                  60

Lys Gly Arg Phe Thr Ile Ser Arg Asp Asn Ser Lys Thr Leu Tyr
 65                  70                  75                  80

Leu Gln Met Ser Asn Leu Arg Ala Glu Asp Ala Val Tyr Phe Cys
                 85                  90                  95

Val Lys Gly Gly Val Leu Met Pro Ala Ala Tyr Phe Trp Gln Gly
                100                 105                 110

Thr Leu Val Thr Val Ser Ser
            115

<210> SEQ ID NO 42
<211> LENGTH: 108
<212> TYPE: PRT
<213> ORGANISM: Homo Sapiens

<400> SEQUENCE: 42

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Phe
                20                  25                  30

Tyr Val Tyr Trp Tyr Gln His Val Pro Gly Thr Ala Pro Lys Leu Leu
             35                  40                  45

Ile Tyr Arg Asn Asn Arg Arg Pro Ser Gly Val Pro Asp Arg Phe Ser
 50                  55                  60

Gly Ser Lys Ser Gly Asn Thr Ala Ser Leu Thr Ile Ser Gly Leu Gln
 65                  70                  75                  80

Ala Glu Asp Glu Ala Asp Tyr Tyr Cys Ser Ser Tyr Pro Arg Asn Thr
                 85                  90                  95

Val Leu Phe Gly Gly Gly Thr Lys Leu Thr Val Leu
                100                 105

<210> SEQ ID NO 43
<211> LENGTH: 118
<212> TYPE: PRT
<213> ORGANISM: Homo Sapiens

<400> SEQUENCE: 43

Gln Val Gln Leu Val Glu Ser Gly Ala Glu Val Lys Lys Pro Gly Ala
```

-continued

```
             1               5                  10                 15
           Ser Val Lys Val Ser Cys Lys Ala Ser Gly Trp Thr Arg Asn Tyr Met
                          20                  25                 30
           His Trp Val Arg Gln Ala Pro Gly Gln Gly Leu Glu Trp Met Gly Trp
                          35                  40                 45
           Ile Asn Pro Lys Asn Gly Gly Thr Asn Tyr Ala Gln Lys Phe Gln Asp
                          50                  55                 60
           Arg Val Thr Met Thr Arg Asp Ser Ser Ile Ser Thr Ala Tyr Met Glu
            65                 70                  75                 80
           Leu Ser Ser Leu Arg Ser Glu Asp Thr Ala Val Tyr Tyr Cys Ala Thr
                          85                  90                 95
           Gly Ile Arg Ser Thr Val Arg Gly Leu Asp Asn Trp Gly Gln Gly Thr
                         100                 105                110
           Leu Val Thr Val Ser Ser
                         115
```

<210> SEQ ID NO 44
<211> LENGTH: 110
<212> TYPE: PRT
<213> ORGANISM: Homo Sapiens

<400> SEQUENCE: 44

```
           Gln Ser Ala Leu Thr Gln Pro Ala Ser Val Ser Gly Ser Pro Gly Gln
            1               5                  10                 15
           Ser Ile Thr Ile Ser Cys Ser Gly Ser Asn Arg Asp Val Gly Gly Tyr
                          20                  25                 30
           Tyr Phe Val Ser Trp Tyr Gln Lys His Pro Gly Lys Ala Pro Arg Leu
                          35                  40                 45
           Met Ile Tyr Asp Val Ile Asn Arg Pro Ser Gly Val Pro Asp Arg Phe
                          50                  55                 60
           Ser Gly Ser Lys Ser Gly Asn Thr Ala Ser Leu Thr Ile Ser Gly Leu
            65                 70                  75                 80
           Gln Pro Glu Asp Glu Gly Tyr Tyr Cys Ser Ser Phe Thr Ser Ser
                          85                  90                 95
           Arg Thr Leu Ala Phe Gly Gly Gly Thr Lys Leu Thr Val Leu
                         100                 105                110
```

<210> SEQ ID NO 45
<211> LENGTH: 118
<212> TYPE: PRT
<213> ORGANISM: Homo Sapiens

<400> SEQUENCE: 45

```
           Gln Val Gln Leu Val Glu Ser Gly Ala Glu Val Lys Lys Pro Gly Ala
            1               5                  10                 15
           Ser Val Lys Val Ser Cys Lys Ala Ser Gly Tyr Thr Leu Thr Ser Tyr
                          20                  25                 30
           Tyr Met His Trp Val Arg Gln Ala Pro Gly Gln Gly Leu Glu Trp Met
                          35                  40                 45
           Gly Ile Ile Asn Pro Ser Gly Gly Asn Thr Ser Tyr Ala Gln Lys Phe
                          50                  55                 60
           Gln Gly Arg Val Thr Met Thr Arg Asp Thr Ser Thr Ser Thr Val Tyr
            65                 70                  75                 80
           Met Glu Leu Ser Ser Leu Arg Pro Asp Asp Thr Ala Val Tyr Tyr Cys
                          85                  90                 95
           Ala Thr Asp Gly Glu Leu Glu Ile Ala Ala Tyr Trp Gly Gln Gly Thr
```

```
                100              105              110
Leu Val Thr Val Ser Ser
        115

<210> SEQ ID NO 46
<211> LENGTH: 111
<212> TYPE: PRT
<213> ORGANISM: Homo Sapiens

<400> SEQUENCE: 46

Leu Pro Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Ala
            20                  25                  30

Tyr Asp Val His Trp Tyr Gln Gln Leu Pro Gly Thr Ala Pro Lys Leu
        35                  40                  45

Leu Ile Tyr Ser Asn Asn Glu Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ser
                85                  90                  95

Leu Asn Gly Tyr Val Phe Gly Thr Gly Thr Lys Leu Thr Val Leu
            100                 105                 110

<210> SEQ ID NO 47
<211> LENGTH: 118
<212> TYPE: PRT
<213> ORGANISM: Homo Sapiens

<400> SEQUENCE: 47

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Arg Arg Gly Asp His Gly Asp Tyr Trp Gly Gln Gly Thr
            100                 105                 110

Leu Val Thr Val Ser Ser
        115

<210> SEQ ID NO 48
<211> LENGTH: 110
<212> TYPE: PRT
<213> ORGANISM: Homo Sapiens

<400> SEQUENCE: 48

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Thr Asp Ile Gly Val Tyr
            20                  25                  30
```

Asp His Val Ser Trp Tyr Gln Gln His Pro Gly Lys Ala Pro Arg Leu
        35                  40                  45

Ile Leu Ser Gly Val Tyr Lys Arg Pro Ser Ala Val Ser Asp Arg Phe
 50                  55                  60

Phe Gly Ser Lys Ser Gly Ser Thr Ala Ser Leu Thr Ile Ser Gly Leu
65                  70                  75                  80

Gln Pro Asp Asp Glu Ala Glu Tyr Arg Cys Met Ser Tyr Thr Thr Ser
                85                  90                  95

Lys Thr Tyr Val Phe Gly Thr Gly Thr Lys Leu Thr Val Leu
            100                 105                 110

<210> SEQ ID NO 49
<211> LENGTH: 116
<212> TYPE: PRT
<213> ORGANISM: Homo Sapiens

<400> SEQUENCE: 49

Gln Val Gln Leu Gln Gln Ser Gly Pro Gly Leu Leu Asn Pro Ser Gln
1               5                   10                  15

Thr Leu Ser Leu Thr Cys Val Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Gln Trp Phe Asn Asp Tyr Ala
 50                  55                  60

Val Ser Val Lys Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Trp Leu His Val Trp Gly Gln Gly Thr Thr Val
            100                 105                 110

Thr Val Ser Ser
        115

<210> SEQ ID NO 50
<211> LENGTH: 115
<212> TYPE: PRT
<213> ORGANISM: Homo Sapiens

<400> SEQUENCE: 50

Gln Ala Gly Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Met Tyr Lys Ser Asp Ser Asp Lys Gln Gln Gly Ser Gly Val
 50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Tyr Val Phe Gly Thr Gly Thr Lys Val
            100                 105                 110

Thr Val Leu
        115

<210> SEQ ID NO 51
<211> LENGTH: 114
<212> TYPE: PRT
<213> ORGANISM: Homo Sapiens

<400> SEQUENCE: 51

```
Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala His Gly Gly Asp Tyr Tyr Trp Gly Gln Gly Thr Pro Val Thr Val
            100                 105                 110

Ser Ser
```

<210> SEQ ID NO 52
<211> LENGTH: 110
<212> TYPE: PRT
<213> ORGANISM: Homo Sapiens

<400> SEQUENCE: 52

```
Gln Ser Ala Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Gly Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110
```

<210> SEQ ID NO 53
<211> LENGTH: 115
<212> TYPE: PRT
<213> ORGANISM: Homo Sapiens

<400> SEQUENCE: 53

```
Glu Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Lys Ser Tyr
                20                  25                  30

Pro Met Ala Trp Val Arg Gln Ala Pro Gly Lys Gly Leu Glu Trp Val
            35                  40                  45

Ser Ser Ile Ser Ser Ser Gly Asp His Arg Tyr Tyr Ala Asp Ser Val
```

```
                 50                  55                  60

Lys Gly Arg Phe Thr Ile Ser Arg Asp Asn Ala Arg Asn Ser Leu Ser
 65                  70                  75                  80

Leu Gln Met Asn Asn Leu Arg Ala Glu Asp Thr Ala Val Tyr Tyr Cys
                 85                  90                  95

Pro Ala Gly Arg Asp Phe Asp His Trp Gly Arg Gly Thr Leu Val Thr
                100                 105                 110

Val Ser Ser
        115

<210> SEQ ID NO 54
<211> LENGTH: 110
<212> TYPE: PRT
<213> ORGANISM: Homo Sapiens

<400> SEQUENCE: 54

Gln Ala Gly Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Ile Ile Asn Glu Val Phe Asn Arg Pro Ser Gly Ser Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Pro Thr Thr Ser
                 85                  90                  95

Lys Thr Leu Val Phe Gly Gly Gly Thr Lys Val Thr Val Leu
                100                 105                 110

<210> SEQ ID NO 55
<211> LENGTH: 119
<212> TYPE: PRT
<213> ORGANISM: Homo Sapiens

<400> SEQUENCE: 55

Glu Val Gln Leu Val Gln Ser Gly Gly Gly Leu Val Gln Pro Gly Gly
  1               5                  10                  15

Ser Leu Arg Leu Ser Cys Ser Ala Ser Gly Phe Thr Phe Ser Ser Tyr
                 20                  25                  30

Ala Met His Trp Val Arg Gln Ala Pro Gly Lys Gly Leu Glu Tyr Val
             35                  40                  45

Ser Ala Ile Ser Ser Asn Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Val Lys Gly Arg Thr Gly Arg Asp Gly Tyr Asn Asp Trp Gly Gln Gly
                100                 105                 110

Thr Leu Val Thr Val Ser Ser
        115

<210> SEQ ID NO 56
<211> LENGTH: 107
<212> TYPE: PRT
```

<213> ORGANISM: Homo Sapiens

<400> SEQUENCE: 56

```
Asp Ile Val Met Thr Gln Ser Pro Pro Ser Leu Ser Ala Ser Val Gly
1               5                   10                  15

Asp Ser Val Ala Ile Thr Cys Arg Ala Ser Gln Asp Ile Arg Asn Asp
            20                  25                  30

Leu Gly Trp Phe Gln Gln Lys Pro Gly Thr Ala Pro Lys Arg Leu Ile
        35                  40                  45

Phe Ala Ala Ser Gly Leu Gln Ser Gly Val Pro Ser Arg Phe Arg Gly
    50                  55                  60

Ser Gly Ser Gly Thr Glu Phe Thr Leu Thr Ile Asn Asn Leu Gln Pro
65                  70                  75                  80

Glu Asp Ser Ala Thr Tyr Tyr Cys Leu Gln His Tyr Arg Phe Pro Arg
                85                  90                  95

Val Phe Gly Gln Gly Thr Lys Val Glu Ile Lys
            100                 105
```

<210> SEQ ID NO 57
<211> LENGTH: 119
<212> TYPE: PRT
<213> ORGANISM: Homo Sapiens

<400> SEQUENCE: 57

```
Glu Val Gln Leu Val Glu Ser Gly Gly Gly Leu Val Gln Pro Gly Gly
1               5                   10                  15

Ser Pro Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Ala Val Arg Gly Val Ser Pro Phe Asp Tyr Trp Gly Gln Gly
            100                 105                 110

Thr Leu Val Thr Val Ser Ser
        115
```

<210> SEQ ID NO 58
<211> LENGTH: 111
<212> TYPE: PRT
<213> ORGANISM: Homo Sapiens

<400> SEQUENCE: 58

```
Gln Ser Val Val Thr Gln Pro Pro Ser Val Ser Gly Ala Pro Gly Gln
1               5                   10                  15

Arg Val Thr Val Ser Cys Thr Gly Ser Ser Asn Ile Gly Ser Arg
            20                  25                  30

Tyr Ala Val Asn Trp Tyr Gln Gln Leu Pro Gly Arg Ala Pro Lys Leu
        35                  40                  45

Leu Ile Tyr Gly Asn Thr Asn Arg Pro Ser Gly Val Pro Asp Arg Phe
    50                  55                  60

Ser Ala Ser Lys Ser Gly Thr Ser Ala Ser Leu Ala Ile Ser Gly Leu
65                  70                  75                  80
```

-continued

```
Gln Ala Glu Asp Glu Ala Asp Tyr Tyr Cys Gln Ser Phe Asp Ser Ser
                85                  90                  95

Leu Arg Gly Tyr Val Phe Gly Thr Gly Thr Lys Val Thr Val Leu
            100                 105                 110

<210> SEQ ID NO 59
<211> LENGTH: 120
<212> TYPE: PRT
<213> ORGANISM: Homo Sapiens

<400> SEQUENCE: 59

Gln Val Gln Leu Gln Gln Ser Gly Pro Gly Leu Val Arg Pro Ser Gln
1               5                   10                  15

Thr Val Ser Leu Thr Cys Val Ile Ser Gly Asp Ser Val Ser Ser Asn
            20                  25                  30

Arg Val Gly Trp Asn Trp Leu Arg Gln Ser Pro Ser Arg Gly Leu Glu
        35                  40                  45

Trp Leu Gly Gly Thr Ala Tyr Arg Ser Thr Trp Arg Leu Tyr Tyr Pro
    50                  55                  60

Pro Ser Leu Lys Ser Arg Val Thr Ile Thr Pro Asp Thr Ser Arg Asn
65                  70                  75                  80

Gln Phe Ser Leu Leu Leu Asn Ser Val Thr Pro Asp Asp Thr Ala Val
                85                  90                  95

Tyr Tyr Cys Ala Arg Gly Phe Val Glu Ala Phe Asp Val Trp Gly Gln
            100                 105                 110

Gly Thr Met Val Thr Val Ser Ser
        115                 120

<210> SEQ ID NO 60
<211> LENGTH: 110
<212> TYPE: PRT
<213> ORGANISM: Homo Sapiens

<400> SEQUENCE: 60

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Arg
                85                  90                  95

Ser Thr Leu Val Phe Gly Gly Gly Thr Gln Leu Thr Val Leu
            100                 105                 110

<210> SEQ ID NO 61
<211> LENGTH: 116
<212> TYPE: PRT
<213> ORGANISM: Homo Sapiens

<400> SEQUENCE: 61

Gln Val Gln Leu Gln Gln Ser Gly Pro Gly Leu Val Lys Pro Ser Gln
1               5                   10                  15
```

```
Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Phe Tyr Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Ser Ser Val Thr Pro Glu Asp Thr Ala Val
                 85                  90                  95

Tyr Tyr Cys Ala Arg Trp Leu His Val Trp Gly Gln Gly Thr Thr Val
            100                 105                 110

Thr Val Ser Ser
            115

<210> SEQ ID NO 62
<211> LENGTH: 110
<212> TYPE: PRT
<213> ORGANISM: Homo Sapiens

<400> SEQUENCE: 62

Gln Ser Val Leu Thr Gln Pro Pro Ser Ala Ser Gly Thr Pro Gly Gln
 1               5                  10                  15

Arg Val Thr Ile Pro Cys Ser Gly Ser Ser Ser Asn Ile Gly Ser Lys
             20                  25                  30

Thr Val Ser Trp Tyr Gln Gln Leu Pro Gly Thr Ala Pro Lys Leu Leu
         35                  40                  45

Ile Tyr Ser Ser Asp Gln Arg Pro Ser Gly Val Pro Asp Arg Phe Ser
 50                  55                  60

Ala Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Gly Ser Leu
                 85                  90                  95

Asp Gly Tyr Val Phe Gly Thr Gly Thr Lys Val Thr Val Leu
            100                 105                 110

<210> SEQ ID NO 63
<211> LENGTH: 117
<212> TYPE: PRT
<213> ORGANISM: Homo Sapiens

<400> SEQUENCE: 63

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asp Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Gln Ala Arg Ser Gly Ser Ser Leu Gly Gln Gly Thr Leu
            100                 105                 110
```

Val Thr Val Ser Ser
        115

<210> SEQ ID NO 64
<211> LENGTH: 110
<212> TYPE: PRT
<213> ORGANISM: Homo Sapiens

<400> SEQUENCE: 64

Gln Ala Val Leu Thr Gln Pro Pro Ser Val Ser Gln Ala Leu Arg Gln
1               5                   10                  15

Thr Ala Thr Leu Thr Cys Thr Gly Asn Ser Asn Asn Val Gly Ser Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Phe Ser
    50                  55                  60

Ala Ser Arg Ser Gly Asp Thr Ala Ser Leu Thr Ile Ser Gly Leu Gln
65                  70                  75                  80

Pro Glu Asp Glu Ala Asp Tyr Phe Cys Ser Ala Trp Asp Asn Ser Leu
                85                  90                  95

Arg Ala Trp Val Phe Gly Gly Gly Thr Lys Leu Thr Val Leu
            100                 105                 110

<210> SEQ ID NO 65
<211> LENGTH: 125
<212> TYPE: PRT
<213> ORGANISM: Homo Sapiens

<400> SEQUENCE: 65

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Val Val Arg Asn Gln Asn Tyr Tyr Tyr Gly Met
            100                 105                 110

Asp Val Trp Gly Gln Gly Thr Val Thr Val Ser Ser
        115                 120                 125

<210> SEQ ID NO 66
<211> LENGTH: 112
<212> TYPE: PRT
<213> ORGANISM: Homo Sapiens

<400> SEQUENCE: 66

Asp Ile Gln Leu Thr Gln Ser Pro Leu Ser Leu Pro Val Thr Leu Gly
1               5                   10                  15

Gln Pro Ala Ser Ile Ser Cys Met Ser Ser Gln Ser Leu Val His Ser
            20                  25                  30

Asp Gly Asn Thr Tyr Leu Asn Trp Phe Gln Gln Arg Pro Gly Gln Ser

```
                    35                   40                   45
Pro Arg Arg Leu Ile Tyr Lys Val Ser Asn Arg Asp Ser Gly Val Pro
 50                   55                   60

Asp Arg Phe Ser Gly Ser Gly Ser Gly Thr Asp Phe Thr Leu Lys Ile
 65                   70                   75                   80

Ser Arg Val Glu Ala Glu Asp Val Gly Val Tyr Tyr Cys Met Gln Gly
                     85                   90                   95

Ser His Trp Pro Arg Thr Phe Gly Gln Gly Thr Arg Leu Glu Ile Lys
                    100                  105                  110

<210> SEQ ID NO 67
<211> LENGTH: 115
<212> TYPE: PRT
<213> ORGANISM: Homo Sapiens

<400> SEQUENCE: 67

Glu Val Gln Leu Val Glu Ser Gly Gly Gly Val Val Gln Pro Gly Arg
 1                    5                   10                   15

Ser Leu Arg Leu Ser Cys Ala Ala Ser Gly Phe Thr Phe Ser Ser Tyr
                     20                   25                   30

Ala Met His Trp Val Arg Gln Ala Pro Gly Lys Gly Leu Glu Trp Val
                     35                   40                   45

Ala Val Ile Ser Tyr Asp Gly Ser Asn Lys Tyr Tyr Ala Asp Ser Val
 50                   55                   60

Lys Gly Arg Phe Thr Ile Ser Arg Asp Asn Ser Lys Asn Thr Leu Tyr
 65                   70                   75                   80

Leu Gln Met Asn Ser Leu Arg Ala Glu Asp Thr Ala Val Tyr Tyr Cys
                     85                   90                   95

Ala Arg Gly Ala Leu Ala Gly Tyr Trp Gly Gln Gly Thr Leu Val Thr
                    100                  105                  110

Val Ser Ser
           115

<210> SEQ ID NO 68
<211> LENGTH: 113
<212> TYPE: PRT
<213> ORGANISM: Homo Sapiens

<400> SEQUENCE: 68

Asp Val Val Met Thr Gln Ser Pro Leu Ser Leu Pro Val Thr Leu Gly
 1                    5                   10                   15

Gln Pro Ala Ser Ile Ser Cys Arg Ser Ser Gln Ser Leu Val His Ser
                     20                   25                   30

Asp Gly Asn Thr Tyr Leu Asn Trp Phe Gln Gln Arg Pro Gly Gln Ser
                     35                   40                   45

Pro Arg Arg Leu Ile Tyr Lys Val Ser Asn Arg Asp Ser Gly Val Pro
 50                   55                   60

Asp Arg Phe Ser Gly Ser Gly Ser Gly Thr Asp Phe Thr Leu Lys Ile
 65                   70                   75                   80

Ser Arg Val Glu Ala Glu Asp Val Gly Val Tyr Tyr Cys Met Gln Gly
                     85                   90                   95

Thr His Trp Pro Pro Trp Thr Phe Gly Gly Gly Thr Lys Leu Glu Ile
                    100                  105                  110

Lys

<210> SEQ ID NO 69
```

```
<211> LENGTH: 117
<212> TYPE: PRT
<213> ORGANISM: Homo Sapiens

<400> SEQUENCE: 69
```

Glu Val Gln Leu Val Glu Ser Gly Gly Gly Leu Ile Gln Pro Gly Gly
1               5                   10                  15

Ser Leu Thr Leu Ser Cys Ala Ala Ser Gly Val Ile Val Ser Ser Tyr
            20                  25                  30

Tyr Met Ser Trp Val Arg Gln Ala Pro Gly Lys Gly Leu Glu Trp Val
        35                  40                  45

Ser Val Val Ser Pro Ser Gly Arg Thr Tyr Tyr Lys Asp Ser Val Lys
50                  55                  60

Gly Arg Phe Thr Ile Ser Arg Asp Thr Ser Lys Asn Thr Val Ser Leu
65                  70                  75                  80

Gln Met Asn Asn Leu Arg Gly Glu Asp Ala Ala Ile Tyr Tyr Cys Thr
                85                  90                  95

Arg Thr Ser Gly Leu Tyr Gly Thr Asp Val Trp Gly Gln Gly Thr Thr
            100                 105                 110

Val Thr Val Ser Ser
            115

```
<210> SEQ ID NO 70
<211> LENGTH: 107
<212> TYPE: PRT
<213> ORGANISM: Homo Sapiens

<400> SEQUENCE: 70
```

Ala Ile Arg Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Phe Ala Thr Tyr Tyr Cys Gln Gln Tyr Asn Ser Tyr Thr Tyr
                85                  90                  95

Thr Phe Gly Gln Gly Thr Lys Leu Glu Ile Lys
            100                 105

```
<210> SEQ ID NO 71
<211> LENGTH: 116
<212> TYPE: PRT
<213> ORGANISM: Homo Sapiens

<400> SEQUENCE: 71
```

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Asp Phe Ser Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Thr Lys Lys Tyr Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Glu Thr Glu Asp Thr Ala Val Tyr Tyr Cys
                 85                  90                  95

Thr Arg Gly Phe Arg Ile Phe Gly Tyr Trp Gly Gln Gly Thr Leu Val
            100                 105                 110

Thr Val Ser Ser
            115

<210> SEQ ID NO 72
<211> LENGTH: 112
<212> TYPE: PRT
<213> ORGANISM: Homo Sapiens

<400> SEQUENCE: 72

Asp Ile Val Met Thr Gln Ser Pro Leu Ser Ser Pro Val Thr Leu Gly
 1               5                  10                  15

Gln Pro Ala Ser Ile Ser Cys Arg Ser Ser Gln Ser Leu Val His Ser
                20                  25                  30

Asn Gly Asn Thr Tyr Leu Ser Trp Leu Gln Gln Arg Pro Gly Gln Pro
             35                 40                  45

Pro Arg Leu Leu Leu Tyr Arg Ile Ser Asn Arg Phe Ser Gly Val Pro
 50                  55                  60

Asp Arg Phe Ser Gly Ser Gly Ala Gly Thr Asn Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Arg Thr Phe Gly Gln Gly Thr Lys Val Asp Ile Lys
            100                 105                 110

<210> SEQ ID NO 73
<211> LENGTH: 121
<212> TYPE: PRT
<213> ORGANISM: Homo Sapiens

<400> SEQUENCE: 73

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Asp Tyr
                20                  25                  30

Tyr Met His Trp Val Arg Gln Ala Pro Gly Glu Gly Leu Glu Trp Met
             35                 40                  45

Gly Trp Ile Asn Pro Asn Ser Gly Asp Thr Asn Tyr Pro Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Glu Met Ala Lys Leu Gly Ile Arg Asn Leu Asp Tyr Trp Gly
            100                 105                 110

Gln Gly Thr Leu Val Thr Val Ser Ser
            115                 120

<210> SEQ ID NO 74
<211> LENGTH: 109
<212> TYPE: PRT
<213> ORGANISM: Homo Sapiens
```

```
<400> SEQUENCE: 74

Gln Ser Ala Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Tyr
            20                  25                  30

Arg Val Asn Trp Tyr Gln Gln Leu Ser Gly Ala Ala Pro Lys Leu Leu
        35                  40                  45

Ile Tyr Arg Asn Asn Gln Arg Pro Ser Gly Val Ser Asn Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Ser Ser Tyr Thr Ser Ser Ser
                85                  90                  95

Ala Val Val Phe Gly Gly Gly Thr Lys Leu Thr Val Leu
            100                 105

<210> SEQ ID NO 75
<211> LENGTH: 120
<212> TYPE: PRT
<213> ORGANISM: Homo Sapiens

<400> SEQUENCE: 75

Gln Val Gln Leu Gln Gln Ser Gly Pro Gly Leu Val Lys Pro Ser Gln
1               5                   10                  15

Thr Leu Ser Leu Thr Cys Val Ile Ser Gly Asp Ser Val Ser Asn Asn
            20                  25                  30

Arg Ala Ala Trp Asn Trp Ile Arg Gln Ser Pro Ser Gly Gly Leu Glu
        35                  40                  45

Trp Leu Gly Arg Thr Tyr Tyr Arg Ser Lys Trp Tyr Ser Asp Tyr Gly
    50                  55                  60

Ala Ser Val Lys Ser Arg Ile Thr Val Asn Pro Asp Thr Ser Lys Asn
65                  70                  75                  80

Gln Phe Ser Leu Gln Val Asn Ser Val Thr Pro Asp Asp Thr Ala Val
                85                  90                  95

Tyr Tyr Cys Ala Arg Gly Lys Val Ser Ala Phe Asp Ile Trp Gly Gln
            100                 105                 110

Gly Thr Met Val Thr Val Ser Ser
        115                 120

<210> SEQ ID NO 76
<211> LENGTH: 110
<212> TYPE: PRT
<213> ORGANISM: Homo Sapiens

<400> SEQUENCE: 76

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Arg His
            20                  25                  30

Ala Val Asn Trp Tyr Gln Gln Leu Pro Gly Thr Ala Pro Lys Leu Leu
        35                  40                  45

Ile Tyr Arg Ser Asn Gln Arg Pro Ser Gly Val Ser Asn Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Ser Ser Tyr Thr Ser Ser Ser
```

```
                    85                  90                  95

Thr Pro Tyr Val Phe Gly Thr Gly Thr Lys Leu Thr Val Leu
                100                 105                 110

<210> SEQ ID NO 77
<211> LENGTH: 115
<212> TYPE: PRT
<213> ORGANISM: Homo Sapiens

<400> SEQUENCE: 77

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Thr Val Glu Asp Thr Ala Val Tyr Tyr Cys
                85                  90                  95

Ala Arg Gly Gly Tyr Pro Arg Gly Trp Gly Gln Gly Thr Leu Val Thr
                100                 105                 110

Val Ser Ser
        115

<210> SEQ ID NO 78
<211> LENGTH: 112
<212> TYPE: PRT
<213> ORGANISM: Homo Sapiens

<400> SEQUENCE: 78

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Ile Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Val Gly Val Tyr Tyr Cys Met Gln Gly
                85                  90                  95

Thr His Trp Pro Pro Thr Phe Gly Gln Gly Thr Lys Val Glu Ile Lys
                100                 105                 110

<210> SEQ ID NO 79
<211> LENGTH: 114
<212> TYPE: PRT
<213> ORGANISM: Homo Sapiens

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

-continued

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Phe
 50                  55                  60

Gln Gly Arg Val Thr Met Thr Thr Asp Thr Ser Thr Ser Thr Ala Tyr
 65                  70                  75                  80

Met Glu Leu Ser Ser Leu Lys Ser Glu Asp Thr Ala Val Tyr Tyr Cys
                 85                  90                  95

Ala Thr Leu Gly Gly Ala Thr Trp Gly Gln Gly Thr Thr Val Thr Val
                 100                 105                 110

Ser Ser

<210> SEQ ID NO 80
<211> LENGTH: 110
<212> TYPE: PRT
<213> ORGANISM: Homo Sapiens

<400> SEQUENCE: 80

Leu Pro Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Val Val Phe Gly Gly Gly Thr Lys Leu Thr Val Leu
                 100                 105                 110

<210> SEQ ID NO 81
<211> LENGTH: 116
<212> TYPE: PRT
<213> ORGANISM: Homo Sapiens

<400> SEQUENCE: 81

Gln Val Gln Leu Gln Gln Ser Gly Pro Gly Leu Val Lys Pro Ser Gln
 1               5                  10                  15

Thr Leu Ser Leu Thr Cys Val Ile Ser Gly Asp Ser Val Ser Ser Asn
             20                  25                  30

Ser Ala Ala Trp Asn Trp Ile Arg Gln Ser Pro Ser Gly Ala Leu Glu
         35                  40                  45

Trp Leu Gly Arg Thr Tyr Tyr Arg Ser Lys Trp Tyr Asn Asp Tyr Ala
 50                  55                  60

Pro Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Lys Trp Leu Ser Val Trp Gly Gln Gly Thr Thr Val
                 100                 105                 110

Thr Val Ser Ser
         115

<210> SEQ ID NO 82
<211> LENGTH: 110
<212> TYPE: PRT
<213> ORGANISM: Homo Sapiens

<400> SEQUENCE: 82

Gln Ala Gly Leu Thr Gln Pro Pro Ser Ala Ser Gly Thr Pro Gly Gln
1               5                   10                  15

Arg Val Thr Ile Pro Cys Ser Gly Ser Ser Asn Ile Gly Ser Lys
            20                  25                  30

Thr Val Ser Trp Tyr Gln Gln Leu Pro Gly Thr Ala Pro Lys Leu Leu
        35                  40                  45

Ile Tyr Ser Ser Asp Gln Arg Pro Ser Gly Val Pro Asp Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asp Gly Tyr Val Phe Gly Thr Gly Thr Lys Leu Thr Val Leu
            100                 105                 110

<210> SEQ ID NO 83
<211> LENGTH: 116
<212> TYPE: PRT
<213> ORGANISM: Homo Sapiens

<400> SEQUENCE: 83

Gln Val Gln Leu Val Gln Ser Gly Ser Val Leu Lys Lys Pro Gly Ala
1               5                   10                  15

Ser Val Lys Val Ser Cys Glu Thr Ser Gly Tyr Ser Phe Thr Ser Tyr
            20                  25                  30

Gly Leu His Trp Leu Arg Gln Ala Pro Gly Gln Gly Leu Gln Trp Met
        35                  40                  45

Gly Trp Ile His Pro Asn Thr Gly Asn Pro Ser Tyr Ala Pro Gly Phe
    50                  55                  60

Thr Gly Arg Tyr Val Phe Ser Arg Asp Thr Ser Val Ser Thr Thr Tyr
65                  70                  75                  80

Leu Gln Ile Asn Ser Leu Glu Asp Gly Asp Thr Ala Ile Tyr Phe Cys
                85                  90                  95

Ala Arg Ala Arg Tyr Gly Leu Asp Val Trp Gly Gln Gly Thr Thr Val
            100                 105                 110

Thr Val Ser Ser
        115

<210> SEQ ID NO 84
<211> LENGTH: 110
<212> TYPE: PRT
<213> ORGANISM: Homo Sapiens

<400> SEQUENCE: 84

Gln Thr Val Val Thr Gln Pro Pro Ser Val Ser Ala Ala Pro Gly Gln
1               5                   10                  15

Lys Val Thr Ile Ser Cys Ser Gly Ser Ser Asn Ile Gly Ser His
            20                  25                  30

Phe Val Ser Trp Tyr Gln Gln Leu Pro Gly Thr Ala Pro Lys Leu Leu
        35                  40                  45

Ile Tyr Asp Asn Lys Lys Arg Pro Ser Gly Ile Pro Asp Arg Phe Ser

```
                50                  55                  60
Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Gly Val Phe Gly Gly Gly Thr Lys Val Thr Val Leu
            100                 105                 110
```

<210> SEQ ID NO 85
<211> LENGTH: 115
<212> TYPE: PRT
<213> ORGANISM: Homo Sapiens

<400> SEQUENCE: 85

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Ser Ser Gly Ser Thr Met Tyr Tyr Ala Asp Ser Val
     50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Asp Asp Asp Thr Ala Val Tyr Tyr Cys
                 85                  90                  95

Ala Arg Gly Gly Tyr Pro Arg Tyr Trp Gly Gln Gly Thr Thr Val Thr
            100                 105                 110

Val Ser Ser
        115
```

<210> SEQ ID NO 86
<211> LENGTH: 110
<212> TYPE: PRT
<213> ORGANISM: Homo Sapiens

<400> SEQUENCE: 86

```
Gln Pro Val Leu Thr Gln Pro Pro Ser Val Ser Lys Gly Leu Arg Gln
  1               5                  10                  15

Thr Ala Thr Leu Thr Cys Thr Gly Asn Ser Ser Asn Val Gly Asn Leu
             20                  25                  30

Gly Ala Ala Trp Leu Gln Gln His Gln Gly Arg Pro Pro Lys Leu Leu
         35                  40                  45

Ser Tyr Arg Asn Asn Asn Arg Pro Ser Gly Ile Ser Glu Arg Leu Ser
     50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ala Ala Trp Asp Thr Ser Leu
                 85                  90                  95

Arg Val Trp Val Phe Gly Gly Gly Thr Lys Leu Thr Val Leu
            100                 105                 110
```

<210> SEQ ID NO 87
<211> LENGTH: 120
<212> TYPE: PRT
<213> ORGANISM: Homo Sapiens

<400> SEQUENCE: 87

Glu Val Gln Leu Leu Glu Ser Gly Ala Glu Val Lys Pro Gly Ala
1               5                   10                  15

Ser Val Lys Val Ser Cys Lys Ala Ser Gly Tyr Thr Phe Ser Arg Tyr
            20                  25                  30

Ala Met His Trp Val Arg Gln Ala Pro Gly Gln Arg Leu Glu Trp Met
        35                  40                  45

Gly Trp Ile His Ala Gly Asn Gly Asn Thr Lys Tyr Ser Gln Lys Phe
    50                  55                  60

Gln Gly Arg Val Thr Ile Ser Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Ile Ala Ala Ala Gly Gly Phe Asp Tyr Trp Gly Gln
                100                 105                 110

Gly Thr Leu Val Thr Val Ser Ser
            115                 120

<210> SEQ ID NO 88
<211> LENGTH: 110
<212> TYPE: PRT
<213> ORGANISM: Homo Sapiens

<400> SEQUENCE: 88

Ser Tyr Val Leu Thr Gln Pro Pro Ser Ala Ser Gly Thr Pro Gly Gln
1               5                   10                  15

Arg Val Thr Leu Ser Cys Ser Gly Ser Ser Ser Asn Ile Gly Arg Asn
            20                  25                  30

Tyr Val Tyr Trp Tyr Gln Gln Leu Pro Gly Thr Ala Pro Lys Leu Val
        35                  40                  45

Leu Tyr Val Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Arg Ala Tyr Val Phe Gly Thr Gly Thr Gln Leu Thr Val Leu
                100                 105                 110

<210> SEQ ID NO 89
<211> LENGTH: 116
<212> TYPE: PRT
<213> ORGANISM: Homo Sapiens

<400> SEQUENCE: 89

Gln Val Thr Leu Arg Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Trp Met Ser Trp Val Arg Gln Ala Pro Gly Lys Gly Leu Glu Trp Val
        35                  40                  45

Ala Ser Ile Lys Lys Asp Ala Ser Gly Glu Tyr Tyr Val Asp Ser Val
    50                  55                  60

Lys Gly Arg Phe Ser Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Gly Trp Val Leu Asp Val Trp Gly Gln Gly Thr Thr Val
            100                 105                 110

Thr Val Ser Ser
        115

<210> SEQ ID NO 90
<211> LENGTH: 108
<212> TYPE: PRT
<213> ORGANISM: Homo Sapiens

<400> SEQUENCE: 90

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 91
<211> LENGTH: 120
<212> TYPE: PRT
<213> ORGANISM: Homo Sapiens

<400> SEQUENCE: 91

Glu Val Gln Leu Val Glu Ser Gly Gly Leu Ile Gln Pro Gly Gly
1               5                   10                  15

Ser Leu Arg Leu Ser Cys Ser Ala Ser Gly Phe Thr Leu Asn Asn Tyr
            20                  25                  30

Tyr Met Asn Trp Val Arg Gln Ala Pro Gly Lys Gly Leu Glu Trp Val
        35                  40                  45

Ser Val Ile Tyr Ser Gly Gly Asn Thr Phe Tyr Ala Asp Ser Val Lys
    50                  55                  60

Gly Arg Phe Ile Ile Ser Arg Asp Ser Ser Lys Asn Ile Leu Tyr Leu
65                  70                  75                  80

Gln Met Asn Ser Leu Arg Ala Glu Asp Thr Ala Val Tyr Tyr Cys Ala
                85                  90                  95

Arg Lys Tyr Cys Ser Gly Gly Tyr Cys Lys Tyr Asp Tyr Trp Gly Gln
            100                 105                 110

Gly Thr Leu Val Thr Val Ser Ser
        115                 120

<210> SEQ ID NO 92
<211> LENGTH: 108
<212> TYPE: PRT
<213> ORGANISM: Homo Sapiens

<400> SEQUENCE: 92

Gln Pro Val Leu Thr Gln Pro Pro Ser Ala Ser Gly Thr Pro Gly Gln
1               5                   10                  15

```
Arg Val Thr Ile Ser Cys Ser Gly Ser Ser Asn Ile Gly Ser Asn
            20                  25                  30

Phe Val Tyr Trp Tyr Gln Gln Phe Pro Gly Met Ala Pro Lys Leu Leu
            35                  40                  45

Ile Tyr Arg Asn Asn Gln Arg Pro Ser Gly Val Pro Asp Arg Phe Ser
 50                      55                  60

Gly Ser Lys Ser Gly Thr Ser Ala Ser Leu Val Ile Ser Gly Leu Arg
 65                  70                  75                  80

Ser Glu Asp Glu Ala Thr Tyr Tyr Cys Ala Ser Trp Glu Thr Ser Leu
                85                  90                  95

Ser Gly Pro Arg Val Phe Gly Gly Gly Thr Lys Leu
                100                 105
```

<210> SEQ ID NO 93
<211> LENGTH: 120
<212> TYPE: PRT
<213> ORGANISM: Homo Sapiens

<400> SEQUENCE: 93

```
Glu Val Gln Leu Leu Glu Ser Gly Ala Glu Val Lys Lys Pro Gly Ala
 1               5                   10                  15

Ser Val Lys Val Ser Cys Lys Ala Ser Gly Tyr Thr Phe Ser Arg Tyr
            20                  25                  30

Ala Met His Trp Val Arg Gln Ala Pro Gly Gln Arg Leu Glu Trp Met
            35                  40                  45

Gly Trp Ile His Ala Gly Asn Gly Asn Thr Lys Tyr Ser Gln Lys Phe
 50                      55                  60

Gln Gly Arg Val Thr Ile Ser Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Ser Ile Ala Ala Ala Gly Gly Phe Asp Tyr Trp Gly Gln
                100                 105                 110

Gly Thr Leu Val Thr Val Ser Ser
        115                 120
```

<210> SEQ ID NO 94
<211> LENGTH: 110
<212> TYPE: PRT
<213> ORGANISM: Homo Sapiens

<400> SEQUENCE: 94

```
Leu Leu Val Leu Thr Gln Ser Pro Ser Ala Ser Gly Thr Pro Gly Gln
 1               5                   10                  15

Arg Val Thr Leu Ser Cys Ser Gly Ser Ser Ser Asn Ile Gly Arg Asn
            20                  25                  30

Tyr Val Tyr Trp Tyr Gln Gln Leu Pro Gly Thr Ala Pro Lys Leu Val
            35                  40                  45

Leu Tyr Val Asn Asp Lys Arg Pro Ser Gly Ile Pro Asp Arg Phe Ser
 50                      55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                85                  90                  95

Arg Ala Tyr Val Phe Gly Thr Gly Thr Lys Val Thr Val Leu
                100                 105                 110
```

```
<210> SEQ ID NO 95
<211> LENGTH: 115
<212> TYPE: PRT
<213> ORGANISM: Homo Sapiens

<400> SEQUENCE: 95

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Met Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Asp Asp Thr Ala Val Tyr Tyr Cys
                85                  90                  95

Ala Arg Gly Gly Tyr Pro Arg Tyr Trp Gly Gln Gly Thr Thr Val Thr
            100                 105                 110

Val Ser Ser
        115

<210> SEQ ID NO 96
<211> LENGTH: 110
<212> TYPE: PRT
<213> ORGANISM: Homo Sapiens

<400> SEQUENCE: 96

Gln Ser Val Leu Thr Gln Pro Pro Ser Val Ser Lys Gly Leu Arg Gln
1               5                   10                  15

Thr Ala Thr Leu Thr Cys Thr Gly Asn Ser Ser Asn Val Gly Asn Leu
            20                  25                  30

Gly Ala Ala Trp Leu Gln Gln His Gln Gly Arg Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ala Ala Trp Asp Thr Ser Leu
                85                  90                  95

Arg Val Trp Val Phe Gly Gly Gly Thr Gln Leu Thr Val Leu
            100                 105                 110

<210> SEQ ID NO 97
<211> LENGTH: 121
<212> TYPE: PRT
<213> ORGANISM: Homo Sapiens

<400> SEQUENCE: 97

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
```

```
            50                   55                   60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Ser Gly Leu Ser Gly Val Gly Ala Thr Asn Val His Tyr Trp Gly
            100                 105                 110

Gln Gly Thr Leu Val Thr Val Ser Ser
        115                 120

<210> SEQ ID NO 98
<211> LENGTH: 110
<212> TYPE: PRT
<213> ORGANISM: Homo Sapiens

<400> SEQUENCE: 98

Leu Pro Val Leu Thr Gln Pro Pro Ser Val Ser Lys Gly Leu Arg Gln
 1               5                  10                  15

Thr Ala Thr Leu Thr Cys Thr Gly Asn Thr Asn Val Gly Asn Gln
                 20                  25                  30

Gly Ala Ala Trp Leu Gln Gln His Gln Gly His Pro Pro Lys Leu Leu
             35                  40                  45

Ser Tyr Arg Asn Asn Asn Arg Pro Ser Gly Ile Ser Glu Arg Leu Ser
 50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ser Ala Trp Asp Ser Ser Leu
                 85                  90                  95

Asn Val Trp Val Phe Gly Gly Gly Thr Lys Leu Thr Val Leu
            100                 105                 110

<210> SEQ ID NO 99
<211> LENGTH: 116
<212> TYPE: PRT
<213> ORGANISM: Homo Sapiens

<400> SEQUENCE: 99

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Ala Met His Trp Val Arg Arg Ala Pro Gly Gln Arg Leu Glu Trp Met
             35                  40                  45

Gly Trp Ile Asn Ala Gly Asn Gly Asn Thr Lys Tyr Ser Gln Lys Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Ile Val Ala Thr Ile Trp Gly Gln Gly Thr Leu Val
            100                 105                 110

Thr Val Ser Ser
        115

<210> SEQ ID NO 100
<211> LENGTH: 110
<212> TYPE: PRT
```

<213> ORGANISM: Homo Sapiens

<400> SEQUENCE: 100

Gln Pro Val Leu Thr Gln Pro Ala Ser Val Ser Gly Ser Pro Gly Gln
1               5                   10                  15

Ser Ile Thr Ile Ser Cys Thr Gly Thr Arg Ser Asp Val Gly Thr Tyr
            20                  25                  30

Asn Leu Val Ser Trp Tyr Gln Arg His Pro Gly Arg Ala Pro Lys Leu
        35                  40                  45

Met Ile Tyr Glu Val Ser Lys Arg Pro Ser Gly Ile Ser Asn Leu Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Cys Ser Tyr Thr Gly Arg
                85                  90                  95

Leu Thr Leu Val Phe Gly Gly Gly Thr Lys Leu Thr Val Leu
            100                 105                 110

<210> SEQ ID NO 101
<211> LENGTH: 119
<212> TYPE: PRT
<213> ORGANISM: Homo Sapiens

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Arg Ala Val Ala Gly Arg Gly Ser Tyr Trp Gly Gln Gly
            100                 105                 110

Thr Leu Val Thr Val Ser Ser
        115

<210> SEQ ID NO 102
<211> LENGTH: 110
<212> TYPE: PRT
<213> ORGANISM: Homo Sapiens

<400> SEQUENCE: 102

Gln Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Leu Val Ser Trp Tyr Gln Arg His Pro Gly Lys Ala Pro Lys Leu
        35                  40                  45

Val Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

```
Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Leu Thr Val Leu
            100                 105                 110

<210> SEQ ID NO 103
<211> LENGTH: 115
<212> TYPE: PRT
<213> ORGANISM: Homo Sapiens

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Leu Ala Pro Gly Lys Gly Leu Glu Trp Val
        35                  40                  45

Ala Val Ile Ser Tyr Asp Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Asn Asn Leu Asp Tyr Trp Gly Gln Gly Thr Leu Val Thr
            100                 105                 110

Val Ser Ser
        115

<210> SEQ ID NO 104
<211> LENGTH: 110
<212> TYPE: PRT
<213> ORGANISM: Homo Sapiens

<400> SEQUENCE: 104

Gln Pro Val Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Arg Tyr
            20                  25                  30

Asn Tyr Val Ser Trp Tyr Gln Gln Tyr Pro Gly Lys Ala Pro Lys Leu
        35                  40                  45

Ile Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Thr Ser Ser
                85                  90                  95

Arg Thr Leu Val Phe Gly Gly Gly Thr Lys Leu Thr Val Leu
            100                 105                 110

<210> SEQ ID NO 105
<211> LENGTH: 119
<212> TYPE: PRT
<213> ORGANISM: Homo Sapiens

<400> SEQUENCE: 105

Gln Val Gln Leu Val Gln Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                85                  90                  95

Ala Arg Lys Gly Leu Ala Ala Pro Gly Lys Gly Tyr Trp Gly Gln Gly
            100                 105                 110

Thr Leu Val Thr Val Ser Ser
            115

<210> SEQ ID NO 106
<211> LENGTH: 110
<212> TYPE: PRT
<213> ORGANISM: Homo Sapiens

<400> SEQUENCE: 106

Leu Pro Val Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Arg Tyr
            20                  25                  30

Gly Tyr Val Ser Trp Tyr Gln Gln His Pro Gly Lys Ala Pro Gln Leu
            35                  40                  45

Met Ile Tyr Glu Val Asn Lys Arg Pro Ser Gly Val Pro Asp Arg Phe
 50                  55                  60

Ser Gly Ser Lys Ser Asp Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 107
<211> LENGTH: 123
<212> TYPE: PRT
<213> ORGANISM: Homo Sapiens

<400> SEQUENCE: 107

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Pro Ile Pro Lys Ser Thr Val Ala Gly Thr Ser Tyr
            100                 105                 110

Trp Gly Gln Gly Thr Leu Val Thr Val Ser Ser
            115                 120

<210> SEQ ID NO 108
<211> LENGTH: 111
<212> TYPE: PRT
<213> ORGANISM: Homo Sapiens

<400> SEQUENCE: 108

Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Asn Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Thr Gly Thr Lys Leu Thr Val Leu
            100                 105                 110

<210> SEQ ID NO 109
<211> LENGTH: 124
<212> TYPE: PRT
<213> ORGANISM: Homo Sapiens

<400> SEQUENCE: 109

Glu Val Gln Leu Val Glu Ser Gly Gly Gly Val Val Gln Pro Gly Gly
1               5                   10                  15

Ser Leu Arg Leu Ser Cys Glu Thr Ser Gly Phe Val Phe Ser Asp Tyr
            20                  25                  30

Ala Met His Trp Val Arg Gln Ala Pro Gly Lys Gly Leu Asp Trp Val
        35                  40                  45

Ala Val Met Ser Ser Asp Gly Ser Asn Lys Tyr Tyr Gly Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Phe Cys
                85                  90                  95

Ala Arg Thr Asn Thr Arg Leu Phe Phe Gly Gly Lys Leu Arg Gly Asp
            100                 105                 110

Phe Trp Gly Gln Gly Thr Leu Val Thr Val Ser Ser
            115                 120

<210> SEQ ID NO 110
<211> LENGTH: 110
<212> TYPE: PRT
<213> ORGANISM: Homo Sapiens

<400> SEQUENCE: 110

Gln Ser Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu

```
                35                  40                  45
Phe Tyr Arg Asn Asn Arg Pro Ser Gly Ile Ser Glu Arg Phe Ser
 50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ser Ala Trp Asp Ser Ser Leu
                 85                  90                  95

Ser Ala Arg Val Phe Gly Gly Gly Thr Lys Leu Thr Val Leu
            100                 105                 110

<210> SEQ ID NO 111
<211> LENGTH: 112
<212> TYPE: PRT
<213> ORGANISM: Homo Sapiens

<400> SEQUENCE: 111

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Lys Gly Leu Glu Trp Val
         35                  40                  45

Ser Val Ile Tyr Ser Gly Gly Ser Thr Tyr Tyr Ala Asp Ser Val Lys
 50                  55                  60

Gly Arg Phe Thr Ile Ser Arg His Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Tyr Val Val Trp Gly Gln Gly Thr Leu Val Thr Val Ser Ser
            100                 105                 110

<210> SEQ ID NO 112
<211> LENGTH: 110
<212> TYPE: PRT
<213> ORGANISM: Homo Sapiens

<400> SEQUENCE: 112

Gln Pro Val Leu Thr Gln Pro Pro Ser Val Ser Lys Asp Leu Arg Gln
 1               5                  10                  15

Thr Ala Thr Leu Thr Cys Thr Gly Asn Ser Asn Asn Val Gly Asn Gln
             20                  25                  30

Gly Ala Thr Trp Leu Gln Gln His Gln Gly His Pro Pro Lys Leu Leu
         35                  40                  45

Ser Tyr Lys Asn Asn Asn Arg Pro Ser Gly Ile Ser Glu Arg Phe Ser
 50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ser Ala Trp Asp Ser Ser Leu
                 85                  90                  95

Ser Ala Trp Val Phe Gly Gly Gly Thr Gln Leu Thr Val Leu
            100                 105                 110

<210> SEQ ID NO 113
<211> LENGTH: 115
<212> TYPE: PRT
<213> ORGANISM: Homo Sapiens

<400> SEQUENCE: 113
```

```
Gln Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Thr Lys Asn Ser Leu Tyr
65                  70                  75                  80

Leu Gln Leu Ser Ser Leu Arg Ala Glu Asp Thr Ala Leu Tyr Tyr Cys
            85                  90                  95

Ala Thr Gly Arg Thr Met Ala Leu Trp Gly Gln Gly Thr Thr Val Thr
        100                 105                 110

Val Ser Ser
        115
```

<210> SEQ ID NO 114
<211> LENGTH: 110
<212> TYPE: PRT
<213> ORGANISM: Homo Sapiens

<400> SEQUENCE: 114

```
Gln Ala Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Asp Val Ser Lys Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
            85                  90                  95

Ser Thr Leu Val Phe Gly Gly Gly Thr Lys Leu Thr Val Leu
        100                 105                 110
```

<210> SEQ ID NO 115
<211> LENGTH: 117
<212> TYPE: PRT
<213> ORGANISM: Homo Sapiens

<400> SEQUENCE: 115

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95
```

```
Ala Arg Asn Thr Val Thr Tyr His Asp Val Trp Gly Gln Gly Thr Thr
                100                 105                 110

Val Thr Val Ser Ser
            115

<210> SEQ ID NO 116
<211> LENGTH: 110
<212> TYPE: PRT
<213> ORGANISM: Homo Sapiens

<400> SEQUENCE: 116

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Asn Asp Val Ser Asn Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu
            100                 105                 110

<210> SEQ ID NO 117
<211> LENGTH: 118
<212> TYPE: PRT
<213> ORGANISM: Homo Sapiens

<400> SEQUENCE: 117

Gln Ile Thr Leu Lys Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Trp Ala Thr Tyr Pro Asp Tyr Trp Gly Gln Gly Thr
            100                 105                 110

Leu Val Thr Val Ser Ser
            115

<210> SEQ ID NO 118
<211> LENGTH: 110
<212> TYPE: PRT
<213> ORGANISM: Homo Sapiens

<400> SEQUENCE: 118

Gln Ser Val Leu Thr Gln Pro Ala Ser Val Ser Gly Ser Gln Gly Gln
1               5                   10                  15
```

```
Ser Ile Thr Ile Ser Cys Thr Gly Thr Ser Ser Asp Val Gly Ala Tyr
                20                  25                  30

Asn Tyr Val Ser Trp Tyr Gln Gln Tyr Pro Gly Glu Ala Pro Arg Leu
            35                  40                  45

Ile Leu Tyr Asp Val Ser Gln Arg Pro Ser Gly Ile Ser Asn Arg Phe
 50                  55                  60

Ser Gly Ser Lys Ser Gly Asn Met Ala Ser Leu Thr Ile Ser Gly Leu
 65                  70                  75                  80

Gln Ala Glu Asp Glu Ala Asp Tyr Tyr Cys Ser Ser Tyr Arg Ser Ser
                85                  90                  95

Ser Thr Val Val Phe Gly Gly Gly Thr Lys Val Thr Val Leu
                100                 105                 110

<210> SEQ ID NO 119
<211> LENGTH: 119
<212> TYPE: PRT
<213> ORGANISM: Homo Sapiens

<400> SEQUENCE: 119

Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Leu Ser Gly Pro Thr Ala Lys Phe Asp Tyr Trp Gly Gln Gly
                100                 105                 110

Thr Leu Val Thr Val Ser Ser
        115

<210> SEQ ID NO 120
<211> LENGTH: 111
<212> TYPE: PRT
<213> ORGANISM: Homo Sapiens

<400> SEQUENCE: 120

Gln Ala Gly Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Lys Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Arg
                85                  90                  95

Ser Thr Leu Phe Val Phe Gly Thr Gly Thr Lys Val Thr Val Leu
                100                 105                 110
```

<210> SEQ ID NO 121
<211> LENGTH: 115
<212> TYPE: PRT
<213> ORGANISM: Homo Sapiens

<400> SEQUENCE: 121

Gln Val Gln Leu Val Glu Ser Gly Gly Gly Val Val Gln Pro Gly Arg
1               5                   10                  15

Ser Leu Arg Leu Tyr Cys Ala Ala Ser Gly Phe Ile Phe Ser Ser Tyr
            20                  25                  30

Ala Ile His Trp Val Arg Gln Ala Pro Gly Lys Gly Leu Glu Trp Val
        35                  40                  45

Ala Val Ile Ser Tyr Asp Gly Ser Lys Lys Tyr Tyr Ala Asp Ser Val
    50                  55                  60

Glu Gly Arg Phe Thr Ile Ser Arg Asp Asn Ser Lys Asn Ser Leu Tyr
65                  70                  75                  80

Leu Gln Met Asn Ser Leu Arg Val Asp Asp Thr Ala Val Tyr Tyr Cys
                85                  90                  95

Ala Ala His Arg Gln Leu Gly Tyr Trp Gly Gln Gly Thr Leu Val Thr
            100                 105                 110

Val Ser Ser
        115

<210> SEQ ID NO 122
<211> LENGTH: 110
<212> TYPE: PRT
<213> ORGANISM: Homo Sapiens

<400> SEQUENCE: 122

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu
            100                 105                 110

<210> SEQ ID NO 123
<211> LENGTH: 126
<212> TYPE: PRT
<213> ORGANISM: Homo Sapiens

<400> SEQUENCE: 123

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val

```
                     50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Leu Thr Arg Gly Ser Asp Tyr Tyr Gly Ser Gly Arg Ser Met
                100                 105                 110

Asn Asp Tyr Trp Gly Gln Gly Thr Leu Val Thr Val Ser Ser
                115                 120                 125

<210> SEQ ID NO 124
<211> LENGTH: 112
<212> TYPE: PRT
<213> ORGANISM: Homo Sapiens

<400> SEQUENCE: 124

Asp Ile Val Met Thr Gln Thr Pro Leu Ser Leu Pro Val Thr Leu Gly
 1               5                  10                  15

Gln Pro Ala Ser Ile Ser Cys Arg Ser Ser Gln Ser Leu Val His Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                    85                  90                  95

Thr His Trp Pro Pro Thr Phe Gly Gln Gly Thr Lys Val Glu Ile Lys
                100                 105                 110

<210> SEQ ID NO 125
<211> LENGTH: 115
<212> TYPE: PRT
<213> ORGANISM: Homo Sapiens

<400> SEQUENCE: 125

Gln Val Gln Leu Val Glu Ser Gly Gly Gly Leu Val Gln Pro Gly Arg
 1               5                  10                  15

Ser Leu Arg Leu Ser Cys Thr Ala Ser Gly Phe Thr Phe Gly Asp Tyr
                20                  25                  30

Ala Val Thr Trp Val Arg Gln Ala Pro Gly Lys Gly Leu Glu Trp Val
            35                  40                  45

Gly Phe Ile Arg Ser Met Thr Tyr Gly Gly Pro Thr Gln Tyr Ala Ala
        50                  55                  60

Ser Val Lys Gly Arg Phe Thr Ile Ser Arg Asp Asp Ser Lys Gly Ile
 65                  70                  75                  80

Ala Tyr Leu Gln Met Asn Arg Leu Lys Thr Glu Asp Thr Ala Val Tyr
                    85                  90                  95

Phe Cys Thr Val Ala Gly Gln His Trp Gly Gln Gly Thr Leu Val Thr
                100                 105                 110

Val Ser Ser
        115

<210> SEQ ID NO 126
<211> LENGTH: 108
<212> TYPE: PRT
```

<213> ORGANISM: Homo Sapiens

<400> SEQUENCE: 126

Ser Tyr Glu Leu Thr Gln Pro Leu Ser Val Ser Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr His Asn
                85                  90                  95

Tyr Val Phe Gly Thr Gly Thr Lys Val Thr Val Leu
            100                 105

<210> SEQ ID NO 127
<211> LENGTH: 127
<212> TYPE: PRT
<213> ORGANISM: Homo Sapiens

<400> SEQUENCE: 127

Glu Val Gln Leu Val Glu Ser Gly Gly Gly Leu Val Lys Pro Gly Arg
1               5                   10                  15

Ser Leu Arg Leu Ser Cys Thr Ala Ser Gly Phe Pro Phe Gly Asp Tyr
            20                  25                  30

Ala Met Ser Trp Phe Arg Gln Ala Pro Gly Lys Gly Leu Glu Trp Val
        35                  40                  45

Ala Leu Ile Ser Tyr Asp Gly Arg Asn Asn Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Phe Tyr Cys
                85                  90                  95

Ala Arg Asp Arg Met Arg Gly Pro Gly Gly Arg Phe Tyr Tyr Tyr His
            100                 105                 110

Ala Met Asp Val Trp Gly Gln Gly Thr Thr Val Thr Val Ser Ser
        115                 120                 125

<210> SEQ ID NO 128
<211> LENGTH: 110
<212> TYPE: PRT
<213> ORGANISM: Homo Sapiens

<400> SEQUENCE: 128

Ser Tyr Glu Leu Met Gln Pro Pro Ser Val Ser Arg Gly Leu Arg Gln
1               5                   10                  15

Thr Ala Thr Leu Thr Cys Ala Gly Thr Arg Asn Asp Val Gly Asn Glu
            20                  25                  30

Gly Ala Ser Trp Leu Gln Gln His Gln Gly His Pro Pro Lys Leu Leu
        35                  40                  45

Ser Tyr Arg Asp Thr Asn Arg Pro Ser Gly Ile Ser Asp Arg Phe Ser
    50                  55                  60

Ala Ser Arg Ser Gly Asn Thr Ala Ser Leu Thr Ile Ser Gly Leu Gln
65                  70                  75                  80

-continued

```
Pro Glu Asp Glu Ala Asp Tyr Tyr Cys Ser Ala Trp Asp Ser Ser Leu
                85                  90                  95

Arg Ala Trp Val Phe Gly Gly Gly Thr Lys Leu Thr Val Leu
            100                 105                 110

<210> SEQ ID NO 129
<211> LENGTH: 124
<212> TYPE: PRT
<213> ORGANISM: Homo Sapiens

<400> SEQUENCE: 129

Gln Val Thr Leu Arg Glu Ser Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Thr Trp Ile Arg Gln Ala Pro Gly Lys Gly Leu Glu Trp Val
                35                  40                  45

Ser Tyr Ile Ser Thr Gly Gly Thr Ile Tyr Tyr Ala Asp Ser Val Lys
            50                  55                  60

Gly Arg Phe Thr Ile Ser Arg Asp Asn Ala Lys Asn Ser Leu Tyr Leu
65              70                  75                  80

Gln Met Asp Ser Leu Arg Ala Glu Asp Thr Ala Val Tyr Tyr Cys Ala
                85                  90                  95

Gly Gly Ala Arg Asp Cys Gly Gly Gly Thr Cys Lys Arg Gly Phe
            100                 105                 110

His Trp Gly Gln Gly Thr Leu Val Thr Val Ser Ser
        115                 120

<210> SEQ ID NO 130
<211> LENGTH: 110
<212> TYPE: PRT
<213> ORGANISM: Homo Sapiens

<400> SEQUENCE: 130

Gln Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser Tyr
                20                  25                  30

Asp Tyr Val Ser Trp Tyr Gln Gln His Pro Gly Lys Ala Pro Lys Val
                35                  40                  45

Met Ile Tyr Asp Val Ser Lys Arg Pro Ser Gly Val Ser Asn Arg Phe
            50                  55                  60

Ser Gly Ser Lys Ser Gly Asn Thr Ala Ser Leu Thr Ile Ser Gly Leu
65              70                  75                  80

Gln Asp Glu Asp Glu Ala Asp Tyr Tyr Cys Arg Ser Tyr Thr Ser Ser
                85                  90                  95

Ala Thr Tyr Val Phe Gly Thr Gly Thr Lys Val Thr Val Leu
            100                 105                 110

<210> SEQ ID NO 131
<211> LENGTH: 117
<212> TYPE: PRT
<213> ORGANISM: Homo Sapiens

<400> SEQUENCE: 131

Glu Val Gln Leu Leu Glu Ser Gly Gly Gly Leu Val Lys Pro Gly Gly
1               5                   10                  15
```

```
Ser Leu Arg Leu Ser Cys Ala Ala Ser Gly Phe Thr Phe Asn Asn Tyr
            20                  25                  30

Ala Met His Trp Val Arg Gln Ala Pro Gly Lys Gly Leu Glu Trp Leu
        35                  40                  45

Thr Val Ile Ser Phe Tyr Gly Gly Lys Gln Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asp Asn Gly Arg His Phe Asp Tyr Trp Gly Gln Gly Thr Leu
            100                 105                 110

Val Thr Val Ser Ser
            115

<210> SEQ ID NO 132
<211> LENGTH: 110
<212> TYPE: PRT
<213> ORGANISM: Homo Sapiens

<400> SEQUENCE: 132

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Arg Ser Gly
                85                  90                  95

Arg Thr Tyr Val Phe Gly Ser Gly Thr Lys Val Thr Val Leu
            100                 105                 110

<210> SEQ ID NO 133
<211> LENGTH: 120
<212> TYPE: PRT
<213> ORGANISM: Homo Sapiens

<400> SEQUENCE: 133

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Thr Thr His
            20                  25                  30

Tyr Ile His Trp Val Arg Gln Ala Pro Gly Gln Gly Leu Glu Trp Met
        35                  40                  45

Gly Ile Ile Asn Pro Asn Ser Gly Arg Thr Lys Tyr Pro Gln Lys Phe
    50                  55                  60

Gln Gly Arg Val Thr Met Thr Arg Asp Thr Ser Thr Asn Thr Val Tyr
65                  70                  75                  80

Met Glu Val Asn Ser Leu Arg Ser Glu Asp Thr Ala Val Tyr Tyr Cys
                85                  90                  95

Ala Thr Gly Ser Gly Ser Tyr Gly Asn Trp Phe Asp Pro Trp Gly Gln
            100                 105                 110
```

```
Gly Thr Leu Val Thr Val Ser Ser
        115             120
```

<210> SEQ ID NO 134
<211> LENGTH: 110
<212> TYPE: PRT
<213> ORGANISM: Homo Sapiens

<400> SEQUENCE: 134

```
Gln Ser Val Val Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Thr Leu Tyr Val Phe Gly Thr Gly Thr Lys Leu Thr Val Leu
            100                 105                 110
```

<210> SEQ ID NO 135
<211> LENGTH: 131
<212> TYPE: PRT
<213> ORGANISM: Homo Sapiens

<400> SEQUENCE: 135

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Leu Asn Trp Val Arg Gln Ala Pro Gly Gln Gly Leu Glu Trp Met
        35                  40                  45

Gly Trp Ile Asn Pro Asn Asn Gly Gly Thr Asn Tyr Ala Gln Arg Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Thr Ala Val Tyr Tyr Cys
                85                  90                  95

Val Arg Gly Thr Arg Lys Tyr Tyr His Asp Ser Asn Gly Arg Arg Arg
            100                 105                 110

Asp Tyr Tyr Tyr Gly Met Asp Val Trp Gly Gln Gly Thr Thr Val Thr
        115                 120                 125

Val Ser Ser
    130
```

<210> SEQ ID NO 136
<211> LENGTH: 106
<212> TYPE: PRT
<213> ORGANISM: Homo Sapiens

<400> SEQUENCE: 136

```
Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

```
                20                  25                  30
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Lys Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Lys Phe Tyr Pro Pro
                85                  90                  95

Asn Phe Gly Gly Gly Thr Lys Val Glu Ile
                100                 105

<210> SEQ ID NO 137
<211> LENGTH: 115
<212> TYPE: PRT
<213> ORGANISM: Homo Sapiens

<400> SEQUENCE: 137

Glu Val Gln Leu Val Glu Ser Gly Gly Gly Leu Val Lys Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Arg Trp Leu Asp Tyr Trp Gly Gln Gly Thr Leu Val Thr
                100                 105                 110

Val Ser Ser
        115

<210> SEQ ID NO 138
<211> LENGTH: 111
<212> TYPE: PRT
<213> ORGANISM: Homo Sapiens

<400> SEQUENCE: 138

Gln Pro Val Leu Thr Gln Pro Ala Ser Val Ser Gly Ser Pro Gly Gln
 1               5                  10                  15

Ser Ile Ala Ile Ser Cys Thr Gly Thr Ser Ser Asp Val Gly Ser Asn
                20                  25                  30

Asn Arg Val Ser Trp Tyr Gln Gln His Pro Gly Lys Ala Pro Lys Leu
            35                  40                  45

Met Ile Tyr Glu Val Asp Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Trp Asp Ser Ser
                85                  90                  95

Leu Ser Ala Tyr Val Phe Gly Thr Gly Thr Lys Leu Thr Val Leu
                100                 105                 110
```

<210> SEQ ID NO 139
<211> LENGTH: 119
<212> TYPE: PRT
<213> ORGANISM: Homo Sapiens

<400> SEQUENCE: 139

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Ala Val Ala Gly Thr His Phe Asp Tyr Trp Gly Gln Gly
            100                 105                 110

Thr Leu Val Thr Val Ser Ser
        115

<210> SEQ ID NO 140
<211> LENGTH: 110
<212> TYPE: PRT
<213> ORGANISM: Homo Sapiens

<400> SEQUENCE: 140

Ser Tyr Glu Leu Met Gln Pro Pro Ser Val Ser Gly Thr Pro Gly Gln
1               5                   10                  15

Arg Val Thr Ile Ser Cys Ser Gly Ser Thr Ser Asn Val Gly Ser Asn
            20                  25                  30

Thr Val Asn Trp Tyr Arg Gln Phe Pro Gly Thr Ala Pro Lys Leu Leu
        35                  40                  45

Ile Tyr Ala Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asn Glu Ala Asp Tyr Tyr Cys Ala Ala Trp Asp Asp Ser Leu
                85                  90                  95

Asn Gly Tyr Val Phe Gly Thr Gly Thr Lys Leu Thr Val Leu
            100                 105                 110

<210> SEQ ID NO 141
<211> LENGTH: 127
<212> TYPE: PRT
<213> ORGANISM: Homo Sapiens

<400> SEQUENCE: 141

Glu Val Gln Leu Val Gln Ser Gly Ala Glu Val Lys Lys Pro Gly Ala
1               5                   10                  15

Ser Leu Lys Ile Ser Cys Arg Ala Ser Gly Tyr Thr Phe Thr Arg Asn
            20                  25                  30

Tyr Ile His Trp Val Arg Gln Ala Pro Gly Gln Gly Leu Glu Trp Leu
        35                  40                  45

Gly Ile Ile Asn Pro Asn Gly Gly Ser Thr Arg Tyr Ser Gln Lys Phe
    50                  55                  60

```
Gln Gly Arg Val Thr Met Thr Arg Asp Thr Ser Thr Arg Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Pro Lys Tyr Cys Ser Gly Ser Ser Cys Tyr Ser Gly
            100                 105                 110

Gly Val Asp Tyr Trp Gly Gln Gly Thr Leu Val Thr Val Ser Ser
        115                 120                 125
```

<210> SEQ ID NO 142
<211> LENGTH: 110
<212> TYPE: PRT
<213> ORGANISM: Homo Sapiens

<400> SEQUENCE: 142

```
Gln Pro Val Leu Thr Gln Pro Leu Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Tyr Gln Arg Pro Ser Gly Val Pro Asp Arg Phe Ser
50                  55                  60

Gly Ser Thr Ser Gly Thr Ser Ala Ser Leu Ala Ile Ser Gly Leu Arg
65                  70                  75                  80

Ser Glu Asp Glu Ala Asp Tyr His Cys Ala Ala Trp Asp Gly Ser Met
                85                  90                  95

Arg Gly Trp Val Phe Gly Gly Gly Thr Lys Leu Thr Val Leu
            100                 105                 110
```

<210> SEQ ID NO 143
<211> LENGTH: 118
<212> TYPE: PRT
<213> ORGANISM: Homo Sapiens

<400> SEQUENCE: 143

```
Gln Ile Thr Leu Lys Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Asn Gly Trp Ala Thr Tyr Pro Asp Tyr Trp Gly Gln Gly Thr
            100                 105                 110

Leu Val Thr Val Ser Ser
        115
```

<210> SEQ ID NO 144
<211> LENGTH: 110
<212> TYPE: PRT
<213> ORGANISM: Homo Sapiens

<400> SEQUENCE: 144

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu
            100                 105                 110

<210> SEQ ID NO 145
<211> LENGTH: 111
<212> TYPE: PRT
<213> ORGANISM: Homo Sapiens

<400> SEQUENCE: 145

Glu Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Val Ile Ser His Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Ser Ser Leu Arg Ala Glu Asp Thr Ala Val Tyr Tyr Cys
                85                  90                  95

Ala Arg Ala Thr Phe Gly Gln Gly Thr Leu Val Thr Val Ser Ser
            100                 105                 110

<210> SEQ ID NO 146
<211> LENGTH: 110
<212> TYPE: PRT
<213> ORGANISM: Homo Sapiens

<400> SEQUENCE: 146

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Cys Ser His Ala Gly Ser
                85                  90                  95

```
Ser Thr Tyr Val Phe Gly Thr Gly Thr Lys Val Thr Val Leu
            100                 105                 110
```

<210> SEQ ID NO 147
<211> LENGTH: 126
<212> TYPE: PRT
<213> ORGANISM: Homo Sapiens

<400> SEQUENCE: 147

```
Glu Val Gln Leu Leu Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Thr Arg Gly Ser Asp Tyr Tyr Gly Ser Gly Arg Ser Met
            100                 105                 110

Asn Asp Tyr Trp Gly Gln Gly Thr Leu Val Thr Val Ser Ser
        115                 120                 125
```

<210> SEQ ID NO 148
<211> LENGTH: 111
<212> TYPE: PRT
<213> ORGANISM: Homo Sapiens

<400> SEQUENCE: 148

```
Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Thr Phe Gly Gln Gly Thr Lys Leu Glu Ile Lys
            100                 105                 110
```

<210> SEQ ID NO 149
<211> LENGTH: 120
<212> TYPE: PRT
<213> ORGANISM: Homo Sapiens

<400> SEQUENCE: 149

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Ile Phe Ser Arg Tyr
                20                  25                  30

Gly Met His Trp Val Arg Gln Ala Pro Gly Lys Gly Leu Glu Trp Val
```

```
                35                  40                  45

Ala Val Thr Ser Tyr Asp Gly Arg Ser Lys Tyr Tyr Thr Asp Ser Val
     50                  55                  60

Gln Gly Arg Phe Thr Ile Ser Arg Asp Asn Ser Lys Asn Thr Leu Asp
 65                  70                  75                  80

Leu Gln Met Asn Ser Leu Arg Ala Glu Asp Thr Ala Val Tyr Tyr Cys
                 85                  90                  95

Ala Arg Leu His Thr Val Gly Pro Trp His Phe Asp Leu Trp Gly Arg
            100                 105                 110

Gly Thr Leu Val Thr Val Ser Ser
            115                 120

<210> SEQ ID NO 150
<211> LENGTH: 110
<212> TYPE: PRT
<213> ORGANISM: Homo Sapiens

<400> SEQUENCE: 150

Ser Tyr Glu Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Val Pro Lys Leu
            35                  40                  45

Met Ile Tyr Glu Val Ser Asn Arg Pro Ser Gly Val Ser Asn Arg Phe
     50                  55                  60

Ser Gly Ser Lys Ser Gly Asn Ala Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Val Phe Gly Gly Gly Thr Lys Leu Thr Val Leu
            100                 105                 110

<210> SEQ ID NO 151
<211> LENGTH: 115
<212> TYPE: PRT
<213> ORGANISM: Homo Sapiens

<400> SEQUENCE: 151

Glu Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Arg Tyr
                20                  25                  30

Gly Met His Trp Val Arg Gln Ser Pro Gly Lys Gly Leu Glu Trp Val
            35                  40                  45

Ala Gly Ile Ser Tyr Asp Gly Ser Asp Lys Tyr Tyr Ala Asp Ser Val
     50                  55                  60

Lys Gly Arg Phe Thr Ile Ser Arg Ala Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Arg Ala Arg Gly Leu Asp Tyr Trp Gly Gln Gly Thr Thr Val Thr
            100                 105                 110

Val Ser Ser
        115
```

```
<210> SEQ ID NO 152
<211> LENGTH: 110
<212> TYPE: PRT
<213> ORGANISM: Homo Sapiens

<400> SEQUENCE: 152

Gln Ala Val Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ser Tyr
            20                  25                  30

Asn Leu Val Ser Trp Tyr Gln Gln His Pro Gly Lys Ala Pro Lys Leu
        35                  40                  45

Ile Ile Tyr Glu Val Asn Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Ile
                85                  90                  95

Asn Thr Val Val Phe Gly Gly Gly Thr Gln Leu Thr Val Leu
            100                 105                 110

<210> SEQ ID NO 153
<211> LENGTH: 117
<212> TYPE: PRT
<213> ORGANISM: Homo Sapiens

<400> SEQUENCE: 153

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Ser Arg Gly Ser Asp Tyr Trp Gly Gln Gly Thr Leu
            100                 105                 110

Val Thr Val Ser Ser
        115

<210> SEQ ID NO 154
<211> LENGTH: 110
<212> TYPE: PRT
<213> ORGANISM: Homo Sapiens

<400> SEQUENCE: 154

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Asp Val Ser Arg Arg Pro Ser Gly Ile Ser Ser Arg Phe
50                  55                  60
```

```
Ser Gly Ser Lys Ser Gly Asn Thr Ala Ser Leu Thr Ile Ser Gly Leu
 65                  70                  75                  80

Gln Thr Glu Asp Asp Gly Asp Tyr Tyr Cys Leu Ser Tyr Thr Thr Ser
             85                  90                  95

Arg Ala Val Val Phe Gly Gly Gly Thr Lys Leu Thr Val Leu
            100                 105                 110
```

<210> SEQ ID NO 155
<211> LENGTH: 121
<212> TYPE: PRT
<213> ORGANISM: Homo Sapiens

<400> SEQUENCE: 155

```
Gln Val Gln Leu Val Glu Ser Gly Gly Val Val Gln Pro Gly Met
 1               5                  10                  15

Ser Leu Arg Leu Ser Cys Ala Ala Ser Gly Phe Thr Phe Ser Ser His
                20                  25                  30

Ala Met His Trp Val Arg Gln Ala Pro Gly Lys Gly Leu Glu Trp Val
             35                  40                  45

Ala Gln Ile Trp Ser Asp Gly Ser Asn Arg Tyr Tyr Ser Asp Ser Val
 50                  55                  60

Lys Gly Arg Phe Thr Ile Ser Arg Asp Gln Ser Lys Asn Thr Val Ser
 65                  70                  75                  80

Leu Gln Met Asn Ser Leu Arg Ala Glu Asp Thr Ala Val Tyr Phe Cys
                85                  90                  95

Ala Arg Asp Gly Gln Ser Met Ala Pro Tyr Ala Met Asp Val Trp Gly
            100                 105                 110

Gln Gly Thr Met Val Thr Val Ser Ser
        115                 120
```

<210> SEQ ID NO 156
<211> LENGTH: 111
<212> TYPE: PRT
<213> ORGANISM: Homo Sapiens

<400> SEQUENCE: 156

```
Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu His Lys
                20                  25                  30

Asn Gly Asn Asn Tyr Leu Asp Trp Tyr Leu Gln Arg Pro Gly Gln Ser
             35                  40                  45

Pro Gln Leu Leu Ile Tyr Leu Ala Ser Asn Arg Ala Ser Gly Val Pro
 50                  55                  60

Asp Arg Phe Ser Gly Ser Gly Ser Gly Thr Asp Phe Thr Leu Glu Ile
 65                  70                  75                  80

Ser Arg Val Gln Pro Glu Asp Val Gly Val Tyr Tyr Cys Met Gln Gly
                85                  90                  95

Leu Gln Thr Pro Thr Phe Gly Pro Gly Thr Lys Val Glu Ile Lys
            100                 105                 110
```

<210> SEQ ID NO 157
<211> LENGTH: 116
<212> TYPE: PRT
<213> ORGANISM: Homo Sapiens

<400> SEQUENCE: 157

```
Gln Val Gln Leu Gln Gln Ser Gly Pro Gly Leu Leu Asn Pro Ser Gln
  1               5                  10                  15

Thr Leu Ser Leu Thr Cys Val Ile Ser Gly Asp Ser Val Ser Ser Asn
             20                  25                  30

Ser Ala Thr Trp Asn Trp Ile Arg Gln Ser Pro Ser Arg Gly Leu Glu
             35                  40                  45

Trp Leu Gly Arg Thr Tyr Tyr Arg Ser Gln Trp Phe Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Ser Ser Val Thr Pro Glu Asp Thr Ala Val
             85                  90                  95

Tyr Tyr Cys Ala Arg Trp Leu His Val Trp Gly Gln Gly Thr Thr Val
            100                 105                 110

Thr Val Ser Ser
            115
```

<210> SEQ ID NO 158
<211> LENGTH: 110
<212> TYPE: PRT
<213> ORGANISM: Homo Sapiens

<400> SEQUENCE: 158

```
Gln Ser Val Val Thr Gln Pro Pro Ser Val Ser Ala Ala Pro Gly Gln
  1               5                  10                  15

Lys Val Thr Ile Ser Cys Ser Gly Ser Ser Ser Asn Ile Gly Ser Lys
             20                  25                  30

Ala Val Asn Trp Tyr Gln Gln Leu Pro Gly Thr Ala Pro Lys Leu Leu
             35                  40                  45

Ile Tyr Gly Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Ala Ser Leu
             85                  90                  95

Asn Gly Tyr Val Phe Gly Thr Gly Thr Lys Val Thr Val Leu
            100                 105                 110
```

<210> SEQ ID NO 159
<211> LENGTH: 125
<212> TYPE: PRT
<213> ORGANISM: Homo Sapiens

<400> SEQUENCE: 159

```
Glu Val Gln Leu Leu Glu Ser Gly Gly Gly Leu Ile Gln Pro Gly Gly
  1               5                  10                  15

Ser Leu Arg Leu Ser Cys Ala Ala Ser Gly Phe Thr Phe Asn Ser Tyr
             20                  25                  30

Gly Met His Trp Val Arg Gln Ala Pro Gly Lys Gly Leu Glu Trp Val
             35                  40                  45

Ala Val Ile Ser Tyr Asp Gly Ser Asn Thr Tyr Tyr Ala Asp Ser Val
 50                  55                  60

Lys Gly Arg Phe Thr Met Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95
```

Ala Arg Leu Gln Lys Gln Val Arg Gln Leu Leu Arg Asn Asp Ala Phe
            100                 105                 110

Asp Ile Trp Gly Gln Gly Thr Met Val Thr Val Ser Ser
            115                 120                 125

<210> SEQ ID NO 160
<211> LENGTH: 111
<212> TYPE: PRT
<213> ORGANISM: Homo Sapiens

<400> SEQUENCE: 160

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Lys Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
    50                  55                  60

Ala Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Phe Met Val Phe Gly Gly Gly Thr Lys Leu Thr Val Leu
            100                 105                 110

<210> SEQ ID NO 161
<211> LENGTH: 121
<212> TYPE: PRT
<213> ORGANISM: Homo Sapiens

<400> SEQUENCE: 161

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Thr Val Ser Thr Asn
            20                  25                  30

Arg Ala Ala Trp Tyr Trp Ile Arg Gln Ser Pro Ser Arg Gly Leu Glu
        35                  40                  45

Trp Leu Gly Arg Thr His Tyr Arg Ser Arg Trp Leu Asn Asp Tyr Ala
    50                  55                  60

Pro Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Ala Ala Gly Arg Ala Phe Asp Ile Trp Gly
            100                 105                 110

Gln Gly Thr Leu Val Thr Val Ser Ser
        115                 120

<210> SEQ ID NO 162
<211> LENGTH: 110
<212> TYPE: PRT
<213> ORGANISM: Homo Sapiens

<400> SEQUENCE: 162

Gln Ala Gly Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn

```
                    20                  25                  30
Tyr Val Tyr Trp Tyr Gln Gln Leu Pro Gly Thr Ala Pro Lys Leu Leu
                35                  40                  45

Ile Tyr Arg Asn Asn Gln Arg Pro Ser Gly Val Pro Asp Arg Phe Ser
         50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Trp Val Phe Gly Gly Gly Thr Gln Leu Thr Val Leu
            100                 105                 110

<210> SEQ ID NO 163
<211> LENGTH: 120
<212> TYPE: PRT
<213> ORGANISM: Homo Sapiens

<400> SEQUENCE: 163

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Ala Phe Asn Asn Tyr
                20                  25                  30

Gly Met His Trp Val Arg Gln Ala Pro Gly Lys Gly Leu Glu Trp Met
            35                  40                  45

Ala Val Ile Ser Asn Asp Gly Asn Arg Gln Tyr Tyr Val Asp Ser Val
         50                  55                  60

Lys Gly Arg Phe Leu Ile Ser Arg Asp Asn Pro Thr Arg Thr Val Tyr
 65                  70                  75                  80

Leu Glu Met Asn Ser Leu Thr Thr Asp Asp Thr Gly Thr Tyr Tyr Cys
                 85                  90                  95

Ala Lys Pro Ser Ser Gly Trp Phe Arg Ala Phe Asp Val Trp Gly Pro
            100                 105                 110

Gly Thr Met Val Thr Val Ser Ser
            115                 120

<210> SEQ ID NO 164
<211> LENGTH: 107
<212> TYPE: PRT
<213> ORGANISM: Homo Sapiens

<400> SEQUENCE: 164

Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Thr Ile Ser Thr Tyr
                20                  25                  30

Leu Asn Trp Tyr Gln Gln Lys Pro Gly Lys Ala Pro Lys Leu Leu Ile
            35                  40                  45

Tyr Asp Ala Ser Ser Leu Gln Ser Gly Val Pro Ser Arg Phe Thr Gly
         50                  55                  60

Ser Ala Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ile Pro Leu
                 85                  90                  95

Thr Phe Gly Gly Gly Thr Lys Leu Glu Ile Lys
            100                 105
```

```
<210> SEQ ID NO 165
<211> LENGTH: 118
<212> TYPE: PRT
<213> ORGANISM: Homo Sapiens

<400> SEQUENCE: 165

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Arg Arg Gly Ala Pro Asp Tyr Trp Gly Gln Gly Thr
            100                 105                 110

Leu Val Thr Val Ser Ser
            115

<210> SEQ ID NO 166
<211> LENGTH: 107
<212> TYPE: PRT
<213> ORGANISM: Homo Sapiens

<400> SEQUENCE: 166

Glu Thr Thr Leu Thr Gln Ser Pro Gly Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Leu
                85                  90                  95

Thr Phe Gly Gly Gly Thr Lys Val Glu Ile Lys
            100                 105

<210> SEQ ID NO 167
<211> LENGTH: 120
<212> TYPE: PRT
<213> ORGANISM: Homo Sapiens

<400> SEQUENCE: 167

Glu Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Thr Asn Tyr
                20                  25                  30

Tyr Ile His Trp Val Arg Gln Ala Pro Gly Gln Gly Leu Glu Trp Met
            35                  40                  45

Gly Ile Ile Asn Pro Ser Gly Gly Ser Ile Gly Ser Pro Gln Lys Phe
        50                  55                  60
```

```
Gln Gly Arg Val Thr Met Thr Arg Asp Thr Ser Thr Asn Thr Val Tyr
 65                  70                  75                  80

Met Glu Leu Ser Ser Leu Arg Ser Glu Asp Thr Ala Val Tyr Tyr Cys
                 85                  90                  95

Ala Ser Arg Ser Phe Gly Asn Asp Gly Val Phe Asp Ile Trp Gly Gln
            100                 105                 110

Gly Thr Met Val Thr Val Ser Ser
        115                 120

<210> SEQ ID NO 168
<211> LENGTH: 110
<212> TYPE: PRT
<213> ORGANISM: Homo Sapiens

<400> SEQUENCE: 168

Leu Pro Val Leu Thr Gln Pro Arg Ser Val Ser Gly Ser Pro Arg Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala His Tyr Tyr Cys Lys Ser Tyr Thr Thr Ser
                 85                  90                  95

Arg Thr Trp Val Phe Gly Gly Gly Thr Lys Leu Thr Val Leu
            100                 105                 110

<210> SEQ ID NO 169
<211> LENGTH: 116
<212> TYPE: PRT
<213> ORGANISM: Homo Sapiens

<400> SEQUENCE: 169

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Asn Arg Tyr Phe Asp Tyr Trp Gly Gln Gly Thr Leu Val
            100                 105                 110

Thr Val Ser Ser
        115

<210> SEQ ID NO 170
<211> LENGTH: 111
<212> TYPE: PRT
<213> ORGANISM: Homo Sapiens
```

<400> SEQUENCE: 170

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ser Arg
            20                  25                  30

Tyr Asp Val His Trp Tyr Gln Gln Leu Pro Gly Gly Ala Pro Lys Leu
            35                  40                  45

Leu Ile Tyr Ser Asn Thr Asn Arg Pro Ser Gly Val Pro Asp Arg Phe
        50                  55                  60

Ser Ala Ser Lys Ser Gly Thr Ser Ala Ser Leu Ala Ile Ser Gly Leu
65                  70                  75                  80

Gln Ala Gly Asp Glu Ala Asp Tyr Phe Cys Gln Ser Phe Asp Ser Ser
                85                  90                  95

Leu Arg Gly Tyr Val Phe Gly Thr Gly Thr Lys Val Thr Val Leu
            100                 105                 110

<210> SEQ ID NO 171
<211> LENGTH: 121
<212> TYPE: PRT
<213> ORGANISM: Homo Sapiens

<400> SEQUENCE: 171

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Arg Leu Val Gly Arg Leu Gly Ala Phe Asp Ile Trp Gly
            100                 105                 110

Gln Gly Thr Met Val Thr Val Ser Ser
            115                 120

<210> SEQ ID NO 172
<211> LENGTH: 111
<212> TYPE: PRT
<213> ORGANISM: Homo Sapiens

<400> SEQUENCE: 172

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Arg Asn Ser Asn Arg Pro Ser Gly Val Pro Asp Arg Phe
        50                  55                  60

Ser Gly Ser Lys Ser Asp Thr Ser Ala Ser Leu Thr Ile Ser Gly Leu
65                  70                  75                  80

```
Gln Ala Glu Asp Glu Ala Asp Tyr Tyr Cys Ser Ser Tyr Arg Ser Gly
                85                  90                  95

Ser Thr Pro Tyr Val Phe Gly Thr Gly Thr Lys Leu Thr Val Leu
            100                 105                 110

<210> SEQ ID NO 173
<211> LENGTH: 113
<212> TYPE: PRT
<213> ORGANISM: Homo Sapiens

<400> SEQUENCE: 173

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Asp Tyr Trp Gly Gln Gly Thr Leu Val Thr Val Ser
            100                 105                 110

Ser

<210> SEQ ID NO 174
<211> LENGTH: 111
<212> TYPE: PRT
<213> ORGANISM: Homo Sapiens

<400> SEQUENCE: 174

Ser Tyr Glu Leu Met Gln Pro Pro Ser Ala Ser Glu Thr Pro Gly Gln
1               5                   10                  15

Arg Val Thr Ile Ser Cys Ser Gly Ser Ser Ser Asn Ile Gly Ser Asn
            20                  25                  30

Phe Val Tyr Trp Tyr Gln Gln Leu Pro Gly Met Ala Pro Lys Leu Leu
        35                  40                  45

Ile Tyr Lys Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Arg Asp Asp Ser Leu
                85                  90                  95

Ser Gly Ser Val Val Phe Gly Gly Gly Thr Lys Val Thr Val Leu
            100                 105                 110

<210> SEQ ID NO 175
<211> LENGTH: 115
<212> TYPE: PRT
<213> ORGANISM: Homo Sapiens

<400> SEQUENCE: 175

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Trp Leu Asp Ser Trp Gly Gln Gly Thr Leu Val Thr
            100                 105                 110

Val Ser Ser
        115
```

<210> SEQ ID NO 176
<211> LENGTH: 110
<212> TYPE: PRT
<213> ORGANISM: Homo Sapiens

<400> SEQUENCE: 176

```
Gln Ala Gly Leu Thr Gln Pro His Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn His Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Val Thr Val Leu
            100                 105                 110
```

<210> SEQ ID NO 177
<211> LENGTH: 121
<212> TYPE: PRT
<213> ORGANISM: Homo Sapiens

<400> SEQUENCE: 177

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Tyr Met His Trp Val Arg Gln Ala Pro Gly Gln Gly Pro Glu Trp Met
        35                  40                  45

Gly Ile Ile Asn Pro Ile Gly Gly Ser Thr Thr Tyr Ala Gln Lys Phe
    50                  55                  60

Gln Gly Arg Val Thr Met Thr Ser Asp Thr Ala Thr Ser Thr Ala Tyr
65                  70                  75                  80

Met Glu Leu Ser Gly Leu Arg Ser Glu Asp Thr Ala Ile Tyr Tyr Cys
                85                  90                  95

Ala Arg Ser Arg Lys Asn Gln Trp His Tyr Gly Met Asp Val Trp Gly
            100                 105                 110

Glu Gly Thr Thr Val Thr Val Ser Ser
        115                 120
```

<210> SEQ ID NO 178
<211> LENGTH: 107
<212> TYPE: PRT
<213> ORGANISM: Homo Sapiens

<400> SEQUENCE: 178

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Val Pro Pro
                85                  90                  95

Thr Phe Gly Gln Gly Thr Lys Val Glu Ile Lys
            100                 105

<210> SEQ ID NO 179
<211> LENGTH: 116
<212> TYPE: PRT
<213> ORGANISM: Homo Sapiens

<400> SEQUENCE: 179

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Ala Phe Asn Arg Tyr
            20                  25                  30

Gly Met His Trp Val Arg Gln Ala Pro Gly Gln Gly Leu Glu Trp Val
        35                  40                  45

Ala Val Ile Ser Tyr Asp Gly Ser Leu Lys Tyr Tyr Ala Asp Ser Val
    50                  55                  60

Lys Gly Arg Phe Thr Ile Ser Arg Asp Asn Ser Asn Asn Thr Leu Tyr
65                  70                  75                  80

Leu Gln Met Asn Ser Leu Ser Ala Asp Asp Thr Ala Val Tyr Tyr Cys
                85                  90                  95

Ala Lys Gly Gly Ala Ala Leu Asp Ser Trp Gly Gln Gly Thr Leu Val
            100                 105                 110

Thr Val Ser Ser
        115

<210> SEQ ID NO 180
<211> LENGTH: 112
<212> TYPE: PRT
<213> ORGANISM: Homo Sapiens

<400> SEQUENCE: 180

Asp Val Val Met Thr Gln Ser Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Thr Thr Tyr Leu Ser Trp Leu Gln Gln Arg Pro Gly Gln Pro
        35                  40                  45

-continued

Pro Arg Leu Leu Ile Tyr Lys Ile Ser Asn Arg Phe Ser Gly Val Pro
            50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Thr Gln Phe Pro Pro Met Phe Gly Gln Gly Thr Lys Val Glu Ile Lys
                100                 105                 110

<210> SEQ ID NO 181
<211> LENGTH: 119
<212> TYPE: PRT
<213> ORGANISM: Homo Sapiens

<400> SEQUENCE: 181

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Thr Ala Lys Phe Asp Tyr Trp Gly Gln Gly
                100                 105                 110

Thr Leu Val Thr Val Ser Ser
            115

<210> SEQ ID NO 182
<211> LENGTH: 111
<212> TYPE: PRT
<213> ORGANISM: Homo Sapiens

<400> SEQUENCE: 182

Gln Ser Val Leu Thr Gln Pro Ala Ser Val Ser Gly Ser Pro Gly Gln
1               5                   10                  15

Ser Ile Ser Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Ile Ser Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Arg Ser
                85                  90                  95

Ser Thr Pro Trp Val Phe Gly Gly Gly Thr Lys Leu Thr Val Leu
                100                 105                 110

<210> SEQ ID NO 183
<211> LENGTH: 119
<212> TYPE: PRT
<213> ORGANISM: Homo Sapiens

<400> SEQUENCE: 183

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Leu Ser Gly Pro Thr Ala Lys Phe Asp Tyr Trp Gly Gln Gly
            100                 105                 110

Thr Leu Val Thr Val Ser Ser
            115

<210> SEQ ID NO 184
<211> LENGTH: 110
<212> TYPE: PRT
<213> ORGANISM: Homo Sapiens

<400> SEQUENCE: 184

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Lys Ile Tyr Asp Val Ser Lys Trp Pro Ser Gly Ile Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Lys Asn
            85                  90                  95

Lys Thr Leu Ile Phe Gly Gly Gly Thr Lys Leu Thr Val Leu
            100                 105                 110

<210> SEQ ID NO 185
<211> LENGTH: 111
<212> TYPE: PRT
<213> ORGANISM: Homo Sapiens

<400> SEQUENCE: 185

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95

Ala Arg Ala Thr Phe Gly Gln Gly Thr Leu Val Thr Val Ser Ser
                100                 105                 110

<210> SEQ ID NO 186
<211> LENGTH: 111
<212> TYPE: PRT
<213> ORGANISM: Homo Sapiens

<400> SEQUENCE: 186

Gln Pro Val Leu Thr Gln Pro Ala Ser Val Ser Gly Ser Pro Gly Gln
1               5                   10                  15

Ser Ile Thr Val Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Pro Tyr Val Phe Gly Thr Gly Thr Lys Val Thr Val Leu
                100                 105                 110

<210> SEQ ID NO 187
<211> LENGTH: 120
<212> TYPE: PRT
<213> ORGANISM: Homo Sapiens

<400> SEQUENCE: 187

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Ile Ala Ala Val Gly Met Asp Val Trp Gly Gln
                100                 105                 110

Gly Thr Thr Val Thr Val Ser Ser
        115                 120

<210> SEQ ID NO 188
<211> LENGTH: 111
<212> TYPE: PRT
<213> ORGANISM: Homo Sapiens

<400> SEQUENCE: 188

Asp Ile Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val Tyr Arg
            20                  25                  30
```

```
Asp Gly Asn Thr Tyr Leu Asn Trp Phe Gln Gln Arg Pro Gly Gln Ser
        35                  40                  45

Pro Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Leu Thr Phe Gly Gln Gly Thr Lys Val Glu Ile
                100                 105                 110

<210> SEQ ID NO 189
<211> LENGTH: 116
<212> TYPE: PRT
<213> ORGANISM: Homo Sapiens

<400> SEQUENCE: 189

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Asn
                 20                  25                  30

Gly Met His Trp Val Arg Gln Ala Pro Gly Lys Gly Leu Glu Trp Val
        35                  40                  45

Ala Ala Ile Ser Tyr Asn Gly Arg Asn Gln Tyr Tyr Ala Asp Ser Leu
 50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Thr Pro Ala Ala Thr Leu Asp Tyr Trp Gly Gln Gly Thr Leu Val
                100                 105                 110

Thr Val Ser Ser
        115

<210> SEQ ID NO 190
<211> LENGTH: 110
<212> TYPE: PRT
<213> ORGANISM: Homo Sapiens

<400> SEQUENCE: 190

Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
        35                  40                  45

Met Ile Tyr Asp Val Thr Tyr Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Val Phe Gly Thr Gly Thr Lys Val Thr Val Leu
                100                 105                 110

<210> SEQ ID NO 191
```

```
<211> LENGTH: 111
<212> TYPE: PRT
<213> ORGANISM: Homo Sapiens

<400> SEQUENCE: 191

Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Thr Phe Gly Gln Gly Thr Leu Val Thr Val Ser Ser
            100                 105                 110

<210> SEQ ID NO 192
<211> LENGTH: 110
<212> TYPE: PRT
<213> ORGANISM: Homo Sapiens

<400> SEQUENCE: 192

Gln Ser Ala Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Thr Val Asn Trp Tyr Gln Gln Leu Pro Gly Thr Ala Pro Lys Leu Leu
        35                  40                  45

Ile His Ser Asn Thr Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Tyr Val Phe Gly Ser Gly Thr Lys Val Thr Val Leu
            100                 105                 110

<210> SEQ ID NO 193
<211> LENGTH: 114
<212> TYPE: PRT
<213> ORGANISM: Homo Sapiens

<400> SEQUENCE: 193

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Thr Ile Ser Tyr Asp Gly Ser Asn Asn Tyr Tyr Ala Ala Ser Val
    50                  55                  60

Lys Gly Arg Phe Thr Val Ser Arg Asp Asn Ser Thr Leu Tyr Leu Gln
65                  70                  75                  80
```

```
Met Asn Ser Leu Arg Ala Glu Asp Thr Ala Val Tyr Tyr Cys Ala Gly
                85                  90                  95

Ala Ile Ala Ala Ala Gly Val Trp Gly Gln Gly Thr Leu Val Thr Val
            100                 105                 110

Ser Ser
```

<210> SEQ ID NO 194
<211> LENGTH: 110
<212> TYPE: PRT
<213> ORGANISM: Homo Sapiens

<400> SEQUENCE: 194

```
Leu Pro Val Leu Thr Gln Pro Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asp Arg Phe
        50                  55                  60

Ser Gly Ser Lys Ser Gly Asn Thr Ala Ser Leu Asn Ile Ser Gly Leu
65                  70                  75                  80

Gln Pro Asp Asp Glu Ala Glu Tyr Tyr Cys Ser Ser Tyr Arg Thr Lys
                85                  90                  95

Asn Thr Leu Val Phe Gly Gly Gly Thr Lys Leu Thr Val Leu
            100                 105                 110
```

<210> SEQ ID NO 195
<211> LENGTH: 115
<212> TYPE: PRT
<213> ORGANISM: Homo Sapiens

<400> SEQUENCE: 195

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Ala Leu Ala Tyr Asp Gly Thr Asn Lys Tyr Tyr Ala Glu Ser Val
        50                  55                  60

Lys Gly Arg Phe Ala Ile Ser Arg Asp Asn Ser Lys Asn Thr Val Phe
65                  70                  75                  80

Leu Gln Met Asn Ser Leu Arg Ala Glu Asp Thr Ala Ile Tyr Tyr Cys
                85                  90                  95

Ala Arg Asp Arg Trp Leu Ser Tyr Trp Gly Gln Gly Thr Leu Val Thr
            100                 105                 110

Val Ser Ser
        115
```

<210> SEQ ID NO 196
<211> LENGTH: 110
<212> TYPE: PRT
<213> ORGANISM: Homo Sapiens

<400> SEQUENCE: 196

```
Gln Ala Gly Leu Thr Gln Pro Ser Leu Ser Gly Ser Pro Gly Gln
1               5                   10                  15
```

```
Thr Val Thr Ile Ser Cys Thr Gly Thr Ser Ser Asp Val Gly Gly Tyr
            20                  25                  30

Asn His Val Ser Trp Tyr Gln Gln His Pro Asp Lys Ala Pro Gln Val
        35                  40                  45

Ile Ile Tyr Asp Val Asn Lys Arg Pro Ser Glu Val Pro Asp Arg Phe
 50                  55                  60

Ser Gly Ser Lys Ser Gly Asn Thr Ala Ser Leu Thr Ile Ser Gly Leu
 65                  70                  75                  80

Gln Pro Glu Asp Glu Ala His Tyr Tyr Cys Thr Ser Tyr Ala Gly Ser
                 85                  90                  95

His Lys Leu Leu Phe Gly Gly Gly Thr Lys Leu Thr Val Leu
            100                 105                 110

<210> SEQ ID NO 197
<211> LENGTH: 124
<212> TYPE: PRT
<213> ORGANISM: Homo Sapiens

<400> SEQUENCE: 197

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Met
        35                  40                  45

Gly Ile Ile Asn Pro Ser Gly Gly Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Val Arg Asp Arg Arg Val Val Ala Ala Thr Thr Pro Ser Ala Phe Asp
            100                 105                 110

Val Trp Gly Gln Gly Thr Met Val Thr Val Ser Ser
            115                 120

<210> SEQ ID NO 198
<211> LENGTH: 110
<212> TYPE: PRT
<213> ORGANISM: Homo Sapiens

<400> SEQUENCE: 198

Gln Ser Val Val Thr Gln Pro Pro Ser Val Ser Ala Ala Pro Gly Gln
1               5                   10                  15

Arg Val Thr Ile Ser Cys Ser Gly Ser Thr Ser Asn Ile Gly Ser Asn
            20                  25                  30

Tyr Val Ser Trp Tyr His Gln Leu Pro Gly Thr Ala Pro Lys Leu Leu
        35                  40                  45

Val Tyr His Asn Asp Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Val Trp Val Phe Gly Gly Gly Thr Lys Val Thr Val Leu
            100                 105                 110
```

<210> SEQ ID NO 199
<211> LENGTH: 115
<212> TYPE: PRT
<213> ORGANISM: Homo Sapiens

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Gly Gln Asn Leu Asp Tyr Trp Gly Gln Gly Thr Leu Val Thr
            100                 105                 110

Val Ser Ser
        115

<210> SEQ ID NO 200
<211> LENGTH: 110
<212> TYPE: PRT
<213> ORGANISM: Homo Sapiens

<400> SEQUENCE: 200

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Ile Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Ser
                85                  90                  95

Ser Thr Gln Val Phe Gly Gly Gly Thr Lys Leu Thr Val Leu
            100                 105                 110

<210> SEQ ID NO 201
<211> LENGTH: 123
<212> TYPE: PRT
<213> ORGANISM: Homo Sapiens

<400> SEQUENCE: 201

Glu Val Gln Leu Val Glu Ser Gly Gly Glu Val Lys Lys Pro Gly Ala
1               5                   10                  15

Ser Val Lys Leu Ser Cys Lys Ser Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

-continued

```
Gly Ile Ile Asn Pro Ser Gly Gly Ser Thr Ser Ser Ala Gln Lys Phe
    50              55                  60

Gln Gly Arg Val Thr Met Thr Arg Asp Thr Ser Thr Arg Thr Val Tyr
65              70                  75                  80

Met Glu Leu Ser Ser Leu Arg Ser Glu Asp Thr Ala Val Tyr Tyr Cys
                85                  90                  95

Ala Arg Gly Ala Pro Asn Trp Asn Tyr Ala Arg Thr Leu Phe Asp Tyr
                100                 105                 110

Trp Gly Gln Gly Thr Leu Val Thr Val Ser Ser
            115                 120

<210> SEQ ID NO 202
<211> LENGTH: 111
<212> TYPE: PRT
<213> ORGANISM: Homo Sapiens

<400> SEQUENCE: 202

Ser Tyr Glu Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Ser Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Ser Ser
                85                  90                  95

Thr Thr His Val Val Phe Gly Gly Gly Thr Lys Leu Thr Val Leu
                100                 105                 110
```

FULLY HUMAN ANTI-CXC CHEMOKINE RECEPTOR 5 (CXCR5) ANTIBODIES

CROSS REFERENCE TO RELATED APPLICATION

The present patent application claims priority from U.S. provisional patent application 62/041,017 filed 22 Aug. 2014.

TECHNICAL FIELD

The present disclosure provides compositions and methods relating to or derived from anti-CXCR5 antibodies. More specifically, the present disclosure provides human antibodies that bind CXCR5, CXCR5-binding fragments and derivatives of such antibodies, and CXCR5-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having CXCR5 related disorders or conditions, including various inflammatory disorders and various cancers.

BACKGROUND

CXCR5, also known as Burkitt lymphoma receptor (BLR1), CD185, MDR15 and MGC117347, is a G protein-coupled receptor which is a member of the CXC chemokine receptor family. A ligand is BLC, also known as CXCL13, which is a B cell chemoattractant. The unprocessed CXCR5 precursor is 372 amino acids in length with a molecular weight of 42 $K_D$. CXCR5 has a role in B cell migration and localization within particular anatomic compartments. Knockout mice lack peripheral lymph nodes, have fewer Peyer's patches and have decreased B cell levels.

SUMMARY

The present disclosure provides a fully human antibody of an IgG class that binds to an CXCR5 epitope with a binding affinity of at least $10^{-6}$M, which has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called 52A9 herein), SEQ ID NO. 3/SEQ ID NO. 4 (called 52A10 herein), SEQ ID NO. 5/SEQ ID NO. 6 (called 52B10 herein), SEQ ID NO. 7/SEQ ID NO. 8 (called 52C6 herein), SEQ ID NO. 9/SEQ ID NO. 10 (called 52D6 herein), SEQ ID NO. 11/SEQ ID NO. 12 (called 52D7 herein), SEQ ID NO. 13/SEQ ID NO. 14 (called 52D11 herein), SEQ ID NO. 15/SEQ ID NO. 16 (called 52E1 herein), SEQ ID NO. 17/SEQ ID NO. 18 (called 52E10 herein), SEQ ID NO. 19/SEQ ID NO. 20 (called 52H9 herein), SEQ ID NO. 21/SEQ ID NO. 22 (called PC12 herein), SEQ ID NO. 23/SEQ ID NO. 24 (called PD10 herein), SEQ ID NO. 25/SEQ ID NO. 26 (called D3-4 herein), SEQ ID NO. 27/SEQ ID NO. 28 (called E2-1 herein), SEQ ID NO. 29/SEQ ID NO. 30 (called A4 or 7A7 herein), SEQ ID NO. 31/SEQ ID NO. 32 (called A8 herein), SEQ ID NO. 33/SEQ ID NO. 34 (called A12 herein), SEQ ID NO. 35/SEQ ID NO. 36 (called B3 herein), SEQ ID NO. 37/SEQ ID NO. 38 (called C8 herein), SEQ ID NO. 39/SEQ ID NO. 40 (called F8 or 10G9 herein), SEQ ID NO. 41/SEQ ID NO. 42 (called G11 herein), SEQ ID NO. 43/SEQ ID NO. 44 (called H3 herein), SEQ ID NO. 45/SEQ ID NO. 46 (called H5 herein), SEQ ID NO. 47/SEQ ID NO. 48 (called H6 herein), SEQ ID NO. 25/SEQ ID NO.

49 (called 2D3 herein), SEQ ID NO. 50/SEQ ID NO. 51 (called 3A11 herein), SEQ ID NO. 52/SEQ ID NO. 53 (called 3B9 herein), SEQ ID NO. 54/SEQ ID NO. 55 (called 3D11 herein), SEQ ID NO. 56/SEQ ID NO. 57 (called 3D12 or 4E12 herein), SEQ ID NO. 58/SEQ ID NO. 59 (called 3E7 herein), SEQ ID NO. 60/SEQ ID NO. 61 (called 3E12 herein), SEQ ID NO. 62/SEQ ID NO. 63 (called 3F7 herein), SEQ ID NO. 64/SEQ ID NO. 65 (called 3G2 herein), SEQ ID NO. 66/SEQ ID NO. 67 (called 3G7 herein), SEQ ID NO. 68/SEQ ID NO. 69 (called 4A5 herein), SEQ ID NO. 70/SEQ ID NO. 71 (called 4E9 herein), SEQ ID NO. 72/SEQ ID NO. 73 (called 4F1 herein), SEQ ID NO. 74/SEQ ID NO. 75 (called 4F4 herein), SEQ ID NO. 76/SEQ ID NO. 77 (called 4H2 herein), SEQ ID NO. 78/SEQ ID NO. 79 (called 5A8 herein), SEQ ID NO. 80/SEQ ID NO. 81 (called 5F1 herein), SEQ ID NO. 82/SEQ ID NO. 83 (called 6A4 herein), SEQ ID NO. 84/SEQ ID NO. 85 (called 6F9 herein), SEQ ID NO. 15/SEQ ID NO. 86 (called 6G5 herein), SEQ ID NO. 87/SEQ ID NO. 88 (called 7B11 or 8B2 herein), SEQ ID NO. 89/SEQ ID NO. 90 (called 7H10 herein), SEQ ID NO. 15/SEQ ID NO. 91 (called 8D12 herein), SEQ ID NO. 92/SEQ ID NO. 93 (called 8H5 herein), SEQ ID NO. 94/SEQ ID NO. 95 (called 9A10 herein), SEQ ID NO. 96/SEQ ID NO. 97 (called 10A12 herein), SEQ ID NO. 98/SEQ ID NO. 99 (called 10B2 herein), SEQ ID NO. 100/SEQ ID NO. 101 (called 10C3 herein), SEQ ID NO. 102/SEQ ID NO. 103 (called 10O7 herein), SEQ ID NO. 104/SEQ ID NO. 105 (called 11E3 herein), SEQ ID NO. 106/SEQ ID NO. 107 (called 11A12 herein), SEQ ID NO. 108/SEQ ID NO. 109 (called 11A7 herein), SEQ ID NO. 110/SEQ ID NO. 111 (called 11C3 herein), SEQ ID NO. 112/SEQ ID NO. 113 (called 11D3 herein), SEQ ID NO. 114/SEQ ID NO. 115 (called 11D4 herein), SEQ ID NO. 116/SEQ ID NO. 117 (called 11D7 herein), SEQ ID NO. 118/SEQ ID NO. 119 (called 11F3 herein), SEQ ID NO. 120/SEQ ID NO. 121 (called 11G3 herein), SEQ ID NO. 122/SEQ ID NO. 123 (called 12A4 herein), SEQ ID NO. 124/SEQ ID NO. 125 (called 12B11 or 14E10 herein), SEQ ID NO. 126/SEQ ID NO. 127 (called 12B4 herein), SEQ ID NO. 128/SEQ ID NO. 129 (called 12C1 herein), SEQ ID NO. 130/SEQ ID NO. 131 (called 12C6 herein), SEQ ID NO. 132/SEQ ID NO. 133 (called 12D11 herein), SEQ ID NO. 134/SEQ ID NO. 135 (called 12D3 herein), SEQ ID NO. 136/SEQ ID NO. 137 (called 12G10 herein), SEQ ID NO. 138/SEQ ID NO. 139 (called 13E10 herein), SEQ ID NO. 114/SEQ ID NO. 140 (called 13E4 herein), SEQ ID NO. 141/SEQ ID NO. 142 (called 13A3 herein), SEQ ID NO. 143/SEQ ID NO. 144 (called 13F8 herein), SEQ ID NO. 145/SEQ ID NO. 146 (called 13F9 herein), SEQ ID NO. 147/SEQ ID NO. 148 (called 13G9 herein), SEQ ID NO. 149/SEQ ID NO. 150 (called 14E5 herein), SEQ ID NO. 151/SEQ ID NO. 152 (called 14B11 herein), SEQ ID NO. 25/SEQ ID NO. 153 (called 14B4 herein), SEQ ID NO. 154/SEQ ID NO. 155 (called 14C10 herein), SEQ ID NO. 156/SEQ ID NO. 157 (called 14C11 herein), SEQ ID NO. 158/SEQ ID NO. 159 (called 14C3 herein), SEQ ID NO. 160/SEQ ID NO. 161 (called 14D7 herein), SEQ ID NO. 162/SEQ ID NO. 163 (called 14F11 herein), SEQ ID NO. 164/SEQ ID NO. 165 (called 14F8 herein), SEQ ID NO. 1664/SEQ ID NO. 167 (called 15C9 herein), SEQ ID NO. 168/SEQ ID NO. 169 (called 15D7 herein), SEQ ID NO. 170/SEQ ID NO. 171 (called 14D9 herein), SEQ ID NO. 172/SEQ ID NO. 173 (called 15F9 herein), SEQ ID NO. 174/SEQ ID NO. 175 (called 15G11 herein), SEQ ID NO. 176/SEQ ID NO. 177 (called 15G7 herein), SEQ ID NO. 19/SEQ ID NO. 178 (called 15G9 herein), SEQ ID NO. 179/SEQ ID NO. 180 (called 15H10 herein), SEQ ID NO. 181/SEQ ID NO. 182 (called 15H12 herein), SEQ ID NO. 183/SEQ ID NO. 184 (called 16E3 herein), SEQ ID NO. 185/SEQ ID NO. 186 (called 16A6 herein), SEQ ID NO. 187/SEQ ID NO. 188 (called 16A8 herein), SEQ ID NO. 189/SEQ ID NO. 190 (called 16B1 herein), SEQ ID NO. 191/SEQ ID NO. 192 (called 16B7 herein), SEQ ID NO. 193/SEQ ID NO. 194 (called 16F8 herein), SEQ ID NO. 195/SEQ ID NO. 196 (called 16F9 herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 25/SEQ ID NO. 49, SEQ ID NO. 50/SEQ ID NO. 51, SEQ ID NO. 52/SEQ ID NO. 53, SEQ ID NO. 54/SEQ ID NO. 55, SEQ ID NO. 56/SEQ ID NO. 57, SEQ ID NO. 58/SEQ ID NO. 59, SEQ ID NO. 60/SEQ ID NO. 61, SEQ ID NO. 62/SEQ ID NO. 63, SEQ ID NO. 64/SEQ ID NO. 65, SEQ ID NO. 66/SEQ ID NO. 67, SEQ ID NO. 68/SEQ ID NO. 69, SEQ ID NO. 70/SEQ ID NO. 71, SEQ ID NO. 72/SEQ ID NO. 73, SEQ ID NO. 74/SEQ ID NO. 75, SEQ ID NO. 76/SEQ ID NO. 77, SEQ ID NO. 78/SEQ ID NO. 79, SEQ ID NO. 80/SEQ ID NO. 81, SEQ ID NO. 82/SEQ ID NO. 83, SEQ ID NO. 84/SEQ ID NO. 85, SEQ ID NO. 15/SEQ ID NO. 86, SEQ ID NO. 87/SEQ ID NO. 88, SEQ ID NO. 89/SEQ ID NO. 90, SEQ ID NO. 15/SEQ ID NO. 91, SEQ ID NO. 92/SEQ ID NO. 93, SEQ ID NO. 94/SEQ ID NO. 95, SEQ ID NO. 96/SEQ ID NO. 97, SEQ ID NO. 98/SEQ ID NO. 99, SEQ ID NO. 100/SEQ ID NO. 101, SEQ ID NO. 102/SEQ ID NO. 103, SEQ ID NO. 104/SEQ ID NO. 105, SEQ ID NO. 106/SEQ ID NO. 107, SEQ ID NO. 108/SEQ ID NO. 109, SEQ ID NO. 110/SEQ ID NO. 111, SEQ ID NO. 112/SEQ ID NO. 113, SEQ ID NO. 114/SEQ ID NO. 115, SEQ ID NO. 116/SEQ ID NO. 117, SEQ ID NO. 118/SEQ ID NO. 119, SEQ ID NO. 120/SEQ ID NO. 121, SEQ ID NO. 122/SEQ ID NO. 123, SEQ ID NO. 124/SEQ ID NO. 125, SEQ ID NO. 126/SEQ ID NO. 127, SEQ ID NO. 128/SEQ ID NO. 129, SEQ ID NO. 130/SEQ ID NO. 131, SEQ ID NO. 132/SEQ ID NO. 133, SEQ ID NO. 134/SEQ ID NO. 135, SEQ ID NO. 136/SEQ ID NO. 137, SEQ ID NO. 138/SEQ ID NO. 139, SEQ ID NO. 114/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 25/SEQ ID NO. 153, SEQ ID NO. 154/SEQ ID NO. 155, SEQ ID NO. 156/SEQ ID NO. 157, SEQ ID NO. 158/SEQ ID NO. 159, SEQ ID NO. 160/SEQ ID NO. 161, SEQ ID NO. 162/SEQ ID NO. 163, SEQ ID NO. 164/SEQ ID NO. 165, SEQ ID NO. 1664/SEQ ID NO. 167, SEQ ID NO. 168/SEQ ID NO. 169, SEQ ID NO. 170/SEQ ID NO. 171, SEQ ID NO. 172/SEQ ID NO. 173, SEQ ID NO. 174/SEQ ID NO. 175, SEQ ID NO. 176/SEQ ID NO. 177, SEQ ID NO. 19/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 25/SEQ ID NO. 49, SEQ ID NO. 50/SEQ ID NO. 51, SEQ ID NO. 52/SEQ ID NO. 53, SEQ ID NO. 54/SEQ ID NO. 55, SEQ ID NO. 56/SEQ ID NO. 57, SEQ ID NO. 58/SEQ ID NO. 59, SEQ ID NO. 60/SEQ ID NO. 61, SEQ ID NO. 62/SEQ ID NO. 63, SEQ ID NO. 64/SEQ ID NO. 65, SEQ ID NO. 66/SEQ ID NO. 67, SEQ ID NO. 68/SEQ ID NO. 69, SEQ ID NO. 70/SEQ ID NO. 71, SEQ ID NO. 72/SEQ ID NO. 73, SEQ ID NO. 74/SEQ ID NO. 75, SEQ ID NO. 76/SEQ ID NO. 77, SEQ ID NO. 78/SEQ ID NO. 79, SEQ ID NO. 80/SEQ ID NO. 81, SEQ ID NO. 82/SEQ ID NO. 83, SEQ ID NO. 84/SEQ ID NO. 85, SEQ ID NO. 15/SEQ ID NO. 86, SEQ ID NO. 87/SEQ ID NO. 88, SEQ ID NO. 89/SEQ ID NO. 90, SEQ ID NO. 15/SEQ ID NO. 91, SEQ ID NO. 92/SEQ ID NO. 93, SEQ ID NO. 94/SEQ ID NO. 95, SEQ ID NO. 96/SEQ ID NO. 97, SEQ ID NO. 98/SEQ ID NO. 99, SEQ ID NO. 100/SEQ ID NO. 101, SEQ ID NO. 102/SEQ ID NO. 103, SEQ ID NO. 104/SEQ ID NO. 105, SEQ ID NO. 106/SEQ ID NO. 107, SEQ ID NO. 108/SEQ ID NO. 109, SEQ ID NO. 110/SEQ ID NO. 111, SEQ ID NO. 112/SEQ ID NO. 113, SEQ ID NO. 114/SEQ ID NO. 115, SEQ ID NO. 116/SEQ ID NO. 117, SEQ ID NO. 118/SEQ ID NO. 119, SEQ ID NO. 120/SEQ ID NO. 121, SEQ ID NO. 122/SEQ ID NO. 123, SEQ ID NO. 124/SEQ ID NO. 125, SEQ ID NO. 126/SEQ ID NO. 127, SEQ ID NO. 128/SEQ ID NO. 129, SEQ ID NO. 130/SEQ ID NO. 131, SEQ ID NO. 132/SEQ ID NO. 133, SEQ ID NO. 134/SEQ ID NO. 135, SEQ ID NO. 136/SEQ ID NO. 137, SEQ ID NO. 138/SEQ ID NO. 139, SEQ ID NO. 114/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 25/SEQ ID NO. 153, SEQ ID NO. 154/SEQ ID NO. 155, SEQ ID NO. 156/SEQ ID NO. 157, SEQ ID NO. 158/SEQ ID NO. 159, SEQ ID NO. 160/SEQ ID NO. 161, SEQ ID NO. 162/SEQ ID NO. 163, SEQ ID NO. 164/SEQ ID NO. 165, SEQ ID NO. 1664/SEQ ID NO. 167, SEQ ID NO. 168/SEQ ID NO. 169, SEQ ID NO. 170/SEQ ID NO. 171, SEQ ID NO. 172/SEQ ID NO. 173, SEQ ID NO. 174/SEQ ID NO. 175, SEQ ID NO. 176/SEQ ID NO. 177, SEQ ID NO. 19/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, and combinations thereof.

The present disclosure further provides a method for treating an inflammatory disease, comprising administering an effective amount of an anti-CXCR5 polypeptide, wherein the anti-CXCR5 polypeptide is selected from the group consisting of a fully human antibody of an IgG class that binds to a CXCR5 epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof;

wherein the fully human antibody Fab fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2 (called 52A9 herein), SEQ ID NO. 3/SEQ ID NO. 4 (called 52A10 herein), SEQ ID NO. 5/SEQ ID NO. 6 (called 52B10 herein), SEQ ID NO. 7/SEQ ID NO. 8 (called 52C6 herein), SEQ ID NO. 9/SEQ ID NO. 10 (called 52D6 herein), SEQ ID NO. 11/SEQ ID NO. 12 (called 52D7 herein), SEQ ID NO. 13/SEQ ID NO. 14 (called 52D11 herein), SEQ ID NO. 15/SEQ ID NO. 16 (called 52E1 herein), SEQ ID NO. 17/SEQ ID NO. 18 (called 52E10 herein), SEQ ID NO. 19/SEQ ID NO. 20 (called 52H9 herein), SEQ ID NO. 21/SEQ ID NO. 22 (called PC12 herein), SEQ ID NO. 23/SEQ ID NO. 24 (called PD10 herein), SEQ ID NO. 25/SEQ ID NO. 26 (called D3-4 herein), SEQ ID NO. 27/SEQ ID NO. 28 (called E2-1 herein), SEQ ID NO. 29/SEQ ID NO. 30 (called A4 or 7A7 herein), SEQ ID NO. 31/SEQ ID NO. 32 (called A8 herein), SEQ ID NO. 33/SEQ ID NO. 34 (called A12 herein), SEQ ID NO. 35/SEQ ID NO. 36 (called B3 herein), SEQ ID NO. 37/SEQ ID NO. 38 (called C8 herein), SEQ ID NO. 39/SEQ ID NO. 40 (called F8 or 10G9 herein), SEQ ID NO. 41/SEQ ID NO. 42 (called G11 herein), SEQ ID NO. 43/SEQ ID NO. 44 (called H3 herein), SEQ ID NO. 45/SEQ ID NO. 46 (called H5 herein), SEQ ID NO. 47/SEQ ID NO. 48 (called H6 herein), SEQ ID NO. 25/SEQ ID NO. 49 (called 2D3 herein), SEQ ID NO. 50/SEQ ID NO. 51 (called 3A11 herein), SEQ ID NO. 52/SEQ ID NO. 53 (called 3B9 herein), SEQ ID NO. 54/SEQ ID NO. 55 (called 3D11 herein), SEQ ID NO. 56/SEQ ID NO. 57 (called 3D12 or 4E12 herein), SEQ ID NO. 58/SEQ ID NO. 59 (called 3E7 herein), SEQ ID NO. 60/SEQ ID NO. 61 (called 3E12 herein), SEQ ID NO. 62/SEQ ID NO. 63 (called 3F7 herein), SEQ ID NO. 64/SEQ ID NO. 65 (called 3G2 herein), SEQ ID NO. 66/SEQ ID NO. 67 (called 3G7 herein), SEQ ID NO. 68/SEQ ID NO. 69 (called 4A5 herein), SEQ ID NO. 70/SEQ ID NO. 71 (called 4E9 herein), SEQ ID NO. 72/SEQ ID NO. 73 (called 4F1 herein), SEQ ID NO. 74/SEQ ID NO. 75 (called 4F4 herein), SEQ ID NO. 76/SEQ ID NO. 77 (called 4H2 herein), SEQ ID NO. 78/SEQ ID NO. 79 (called 5A8 herein), SEQ ID NO. 80/SEQ ID NO. 81 (called 5F1 herein), SEQ ID NO. 82/SEQ ID NO. 83 (called 6A4 herein), SEQ ID NO. 84/SEQ ID NO. 85 (called 6F9 herein), SEQ ID NO. 15/SEQ ID NO. 86 (called 6G5 herein), SEQ ID NO. 87/SEQ ID NO. 88 (called 7B11 or 8B2 herein), SEQ ID NO. 89/SEQ ID NO. 90 (called 7H10 herein), SEQ ID NO. 15/SEQ ID NO. 91 (called 8D12 herein), SEQ ID NO. 92/SEQ ID NO. 93 (called 8H5 herein), SEQ ID NO. 94/SEQ ID NO. 95 (called 9A10 herein), SEQ ID NO. 96/SEQ ID NO. 97 (called 10A12 herein), SEQ ID NO. 98/SEQ ID NO. 99 (called 10B2 herein), SEQ ID NO. 100/SEQ ID NO. 101 (called 10C3 herein), SEQ ID NO. 102/SEQ ID NO. 103 (called 10O7 herein), SEQ ID NO. 104/SEQ ID NO. 105 (called 11E3 herein), SEQ ID NO. 106/SEQ ID NO. 107 (called 11A12 herein), SEQ ID NO. 108/SEQ ID NO. 109 (called 11A7 herein), SEQ ID NO. 110/SEQ ID NO. 111 (called 11C3 herein), SEQ ID NO. 112/SEQ ID NO. 113 (called 11D3 herein), SEQ ID NO. 114/SEQ ID NO. 115 (called 11D4 herein), SEQ ID NO. 116/SEQ ID NO. 117 (called 11D7 herein), SEQ ID NO. 118/SEQ ID NO. 119 (called 11F3 herein), SEQ ID NO. 120/SEQ ID NO. 121 (called 11G3 herein), SEQ ID NO. 122/SEQ ID NO. 123 (called 12A4 herein), SEQ ID NO. 124/SEQ ID NO. 125 (called 12B11 or 14E10 herein), SEQ ID NO. 126/SEQ ID NO. 127 (called 12B4 herein), SEQ ID NO. 128/SEQ ID NO. 129 (called 12C1 herein), SEQ ID NO. 130/SEQ ID NO. 131 (called 12C6 herein), SEQ ID NO. 132/SEQ ID NO. 133 (called 12D11 herein), SEQ ID NO. 134/SEQ ID NO. 135 (called 12D3 herein), SEQ ID NO. 136/SEQ ID NO. 137 (called 12G10 herein), SEQ ID NO. 138/SEQ ID NO. 139 (called 13E10 herein), SEQ ID NO. 114/SEQ ID NO. 140 (called 13E4 herein), SEQ ID NO. 141/SEQ ID NO. 142 (called 13A3 herein), SEQ ID NO. 143/SEQ ID NO. 144 (called 13F8 herein), SEQ ID NO. 145/SEQ ID NO. 146 (called 13F9 herein), SEQ ID NO. 147/SEQ ID NO. 148 (called 13G9 herein), SEQ ID NO. 149/SEQ ID NO. 150 (called 14E5 herein), SEQ ID NO. 151/SEQ ID NO. 152 (called 14B11 herein), SEQ ID NO. 25/SEQ ID NO. 153 (called 14B4 herein), SEQ ID NO. 154/SEQ ID NO. 155 (called 14C10 herein), SEQ ID NO. 156/SEQ ID NO. 157 (called 14C11 herein), SEQ ID NO. 158/SEQ ID NO. 159 (called 14C3 herein), SEQ ID NO. 160/SEQ ID NO. 161 (called 14D7 herein), SEQ ID NO. 162/SEQ ID NO. 163 (called 14F11 herein), SEQ ID NO. 164/SEQ ID NO. 165 (called 14F8 herein), SEQ ID NO. 1664/SEQ ID NO. 167 (called 15C9 herein), SEQ ID NO. 168/SEQ ID NO. 169 (called 15D7 herein), SEQ ID NO. 170/SEQ ID NO. 171 (called 14D9 herein), SEQ ID NO. 172/SEQ ID NO. 173 (called 15F9 herein), SEQ ID NO. 174/SEQ ID NO. 175 (called 15G11 herein), SEQ ID NO. 176/SEQ ID NO. 177 (called 15G7 herein), SEQ ID NO. 19/SEQ ID NO. 178 (called 15G9 herein), SEQ ID NO. 179/SEQ ID NO. 180 (called 15H10 herein), SEQ ID NO. 181/SEQ ID NO. 182 (called 15H12 herein), SEQ ID NO. 183/SEQ ID NO. 184 (called 16E3 herein), SEQ ID NO. 185/SEQ ID NO. 186 (called 16A6 herein), SEQ ID NO. 187/SEQ ID NO. 188 (called 16A8 herein), SEQ ID NO. 189/SEQ ID NO. 190 (called 16B1 herein), SEQ ID NO. 191/SEQ ID NO. 192 (called 16B7 herein), SEQ ID NO. 193/SEQ ID NO. 194 (called 16F8 herein), SEQ ID NO. 195/SEQ ID NO. 196 (called 16F9 herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called 52A9 herein), SEQ ID NO. 3/SEQ ID NO. 4 (called 52A10 herein), SEQ ID NO. 5/SEQ ID NO. 6 (called 52B10 herein), SEQ ID NO. 7/SEQ ID NO. 8 (called 52C6 herein), SEQ ID NO. 9/SEQ ID NO. 10 (called 52D6 herein), SEQ ID NO. 11/SEQ ID NO. 12 (called 52D7 herein), SEQ ID NO. 13/SEQ ID NO. 14 (called 52D11 herein), SEQ ID NO. 15/SEQ ID NO. 16 (called 52E1 herein), SEQ ID NO. 17/SEQ ID NO. 18 (called 52E10 herein), SEQ ID NO. 19/SEQ ID NO. 20 (called 52H9 herein), SEQ ID NO. 21/SEQ ID NO. 22 (called PC12 herein), SEQ ID NO. 23/SEQ ID NO. 24 (called PD10 herein), SEQ ID NO. 25/SEQ ID NO. 26 (called D3-4 herein), SEQ ID NO. 27/SEQ ID NO. 28 (called E2-1 herein), SEQ ID NO. 29/SEQ ID NO. 30 (called A4 or 7A7 herein), SEQ ID NO. 31/SEQ ID NO. 32 (called A8 herein), SEQ ID NO. 33/SEQ ID NO. 34 (called A12 herein), SEQ ID NO. 35/SEQ ID NO. 36 (called B3 herein), SEQ ID NO. 37/SEQ ID NO. 38 (called C8 herein), SEQ ID NO. 39/SEQ ID NO. 40 (called F8 or 10G9 herein), SEQ ID NO. 41/SEQ ID NO. 42 (called G11 herein), SEQ ID NO. 43/SEQ ID NO. 44 (called H3 herein), SEQ ID NO. 45/SEQ ID NO. 46 (called H5 herein), SEQ ID NO. 47/SEQ ID NO. 48 (called H6 herein), SEQ ID NO. 25/SEQ ID NO. 49 (called 2D3 herein), SEQ ID NO. 50/SEQ ID NO. 51 (called 3A11 herein), SEQ ID NO. 52/SEQ ID NO. 53 (called 3B9 herein), SEQ ID NO. 54/SEQ ID NO. 55 (called 3D11 herein), SEQ ID NO. 56/SEQ ID NO. 57 (called 3D12 or 4E12 herein), SEQ ID NO. 58/SEQ ID NO. 59 (called 3E7 herein), SEQ ID NO. 60/SEQ ID NO. 61 (called 3E12 herein), SEQ ID NO. 62/SEQ ID NO. 63 (called 3F7 herein), SEQ ID NO. 64/SEQ ID NO. 65 (called 3G2 herein), SEQ ID NO. 66/SEQ ID NO. 67 (called 3G7 herein), SEQ ID NO. 68/SEQ ID NO. 69 (called 4A5 herein), SEQ ID NO. 70/SEQ ID NO. 71 (called 4E9 herein), SEQ ID NO. 72/SEQ ID NO. 73 (called 4F1 herein), SEQ ID NO. 74/SEQ ID NO. 75 (called 4F4 herein), SEQ ID NO. 76/SEQ ID NO. 77 (called 4H2 herein), SEQ ID NO. 78/SEQ ID NO. 79 (called 5A8 herein), SEQ ID NO. 80/SEQ ID NO. 81 (called 5F1 herein), SEQ ID NO. 82/SEQ ID NO. 83 (called 6A4 herein), SEQ ID NO. 84/SEQ ID NO. 85 (called 6F9 herein), SEQ ID NO. 15/SEQ ID NO. 86 (called 6G5 herein), SEQ ID NO. 87/SEQ ID NO. 88 (called 7B11 or 8B2 herein), SEQ ID NO. 89/SEQ ID NO. 90 (called 7H10 herein), SEQ ID NO. 15/SEQ ID NO. 91 (called 8D12 herein), SEQ ID NO. 92/SEQ ID NO. 93 (called 8H5 herein), SEQ ID NO. 94/SEQ ID NO. 95 (called 9A10 herein), SEQ ID NO. 96/SEQ ID NO. 97 (called 10A12 herein), SEQ ID NO. 98/SEQ ID NO. 99 (called 10B2 herein), SEQ ID NO. 100/SEQ ID NO. 101 (called 10C3 herein), SEQ ID NO. 102/SEQ ID NO. 103 (called 1OO7 herein), SEQ ID NO. 104/SEQ ID NO. 105 (called 11E3 herein), SEQ ID NO. 106/SEQ ID NO. 107 (called 11A12 herein), SEQ ID NO. 108/SEQ ID NO. 109 (called 11A7 herein), SEQ ID NO. 110/SEQ ID NO. 111 (called 11C3 herein), SEQ ID NO. 112/SEQ ID NO. 113 (called 11D3 herein), SEQ ID NO. 114/SEQ ID NO. 115 (called 11D4 herein), SEQ ID NO. 116/SEQ ID NO. 117 (called 11D7 herein), SEQ ID NO. 118/SEQ ID NO. 119 (called 11F3 herein), SEQ ID NO. 120/SEQ ID NO. 121 (called 11G3 herein), SEQ ID NO. 122/SEQ ID NO. 123 (called 12A4 herein), SEQ ID NO. 124/SEQ ID NO. 125 (called 12B11 or 14E10 herein), SEQ ID NO. 126/SEQ ID NO. 127 (called 12B4 herein), SEQ ID NO. 128/SEQ ID NO. 129 (called 12C1 herein), SEQ ID NO. 130/SEQ ID NO. 131 (called 12C6 herein), SEQ ID NO. 132/SEQ ID NO. 133 (called 12D11 herein), SEQ ID NO. 134/SEQ ID NO. 135 (called 12D3 herein), SEQ ID NO. 136/SEQ ID NO. 137 (called 12G10 herein), SEQ ID NO. 138/SEQ ID NO. 139 (called 13E10 herein), SEQ ID NO. 114/SEQ ID NO. 140 (called 13E4 herein), SEQ ID NO. 141/SEQ ID NO. 142 (called 13A3 herein), SEQ ID NO. 143/SEQ ID NO. 144 (called 13F8 herein), SEQ ID NO. 145/SEQ ID NO. 146 (called 13F9 herein), SEQ ID NO. 147/SEQ ID NO. 148 (called 13G9 herein), SEQ ID NO. 149/SEQ ID NO. 150 (called 14E5 herein), SEQ ID NO. 151/SEQ ID NO. 152 (called 14B11 herein), SEQ ID NO. 25/SEQ ID NO. 153 (called 14B4 herein), SEQ ID NO. 154/SEQ ID NO. 155 (called 14C10 herein), SEQ ID NO. 156/SEQ ID NO. 157 (called 14C11 herein), SEQ ID NO. 158/SEQ ID NO. 159 (called 14C3 herein), SEQ ID NO. 160/SEQ ID NO. 161 (called 14D7 herein), SEQ ID NO. 162/SEQ ID NO. 163 (called 14F11 herein), SEQ ID NO. 164/SEQ ID NO. 165 (called 14F8 herein), SEQ ID NO. 1664/SEQ ID NO. 167 (called 15C9 herein), SEQ ID NO. 168/SEQ ID NO. 169 (called 15D7 herein), SEQ ID NO. 170/SEQ ID NO. 171 (called 14D9 herein), SEQ ID NO. 172/SEQ ID NO. 173 (called 15F9 herein), SEQ ID NO. 174/SEQ ID NO. 175 (called 15G11 herein), SEQ ID NO. 176/SEQ ID NO. 177 (called 15G7 herein), SEQ ID NO. 19/SEQ ID NO. 178 (called 15G9 herein), SEQ ID NO. 179/SEQ ID NO. 180 (called 15H10 herein), SEQ ID NO. 181/SEQ ID NO. 182 (called 15H12 herein), SEQ ID NO. 183/SEQ ID NO. 184 (called 16E3 herein), SEQ ID NO. 185/SEQ ID NO. 186 (called 16A6 herein), SEQ ID NO. 187/SEQ ID NO. 188 (called 16A8 herein), SEQ ID NO. 189/SEQ ID NO. 190 (called 16B1 herein), SEQ ID NO. 191/SEQ ID NO. 192 (called 16B7 herein), SEQ ID NO. 193/SEQ ID NO. 194 (called 16F8 herein), SEQ ID NO. 195/SEQ ID NO. 196 (called 16F9 herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 25/SEQ ID NO. 49, SEQ ID NO. 50/SEQ ID NO. 51, SEQ ID NO. 52/SEQ ID NO. 53, SEQ ID NO. 54/SEQ ID NO. 55, SEQ ID NO. 56/SEQ ID NO. 57, SEQ ID NO. 58/SEQ ID NO. 59, SEQ ID NO. 60/SEQ ID NO. 61, SEQ ID NO. 62/SEQ ID NO. 63, SEQ ID NO. 64/SEQ ID NO. 65, SEQ ID NO. 66/SEQ ID NO. 67, SEQ ID NO. 68/SEQ ID NO. 69, SEQ ID NO. 70/SEQ ID NO. 71, SEQ ID NO. 72/SEQ ID NO. 73, SEQ ID NO. 74/SEQ ID NO. 75, SEQ ID NO. 76/SEQ ID NO. 77, SEQ ID NO. 78/SEQ ID NO. 79, SEQ ID NO. 80/SEQ ID NO. 81, SEQ ID NO. 82/SEQ ID NO. 83, SEQ ID NO. 84/SEQ ID NO. 85, SEQ ID NO. 15/SEQ ID NO. 86, SEQ ID NO. 87/SEQ ID NO. 88, SEQ ID NO. 89/SEQ ID NO. 90, SEQ ID NO. 15/SEQ ID NO. 91, SEQ ID NO. 92/SEQ ID NO. 93, SEQ ID NO. 94/SEQ ID NO. 95, SEQ ID NO. 96/SEQ ID NO. 97, SEQ ID NO. 98/SEQ ID NO. 99, SEQ ID NO. 100/SEQ ID NO. 101, SEQ ID NO. 102/SEQ ID NO. 103, SEQ ID NO. 104/SEQ ID NO. 105, SEQ ID NO. 106/SEQ ID NO. 107, SEQ ID NO. 108/SEQ ID NO. 109, SEQ ID NO. 110/SEQ ID NO. 111, SEQ ID NO. 112/SEQ ID NO. 113, SEQ ID NO. 114/SEQ ID NO. 115, SEQ ID NO. 116/SEQ ID NO. 117, SEQ ID NO. 118/SEQ ID NO. 119, SEQ ID NO. 120/SEQ ID NO. 121, SEQ ID NO. 122/SEQ ID NO. 123, SEQ ID NO. 124/SEQ ID NO. 125, SEQ ID NO. 126/SEQ ID NO. 127, SEQ ID NO. 128/SEQ ID NO. 129, SEQ ID NO. 130/SEQ ID NO. 131, SEQ ID NO. 132/SEQ ID NO. 133, SEQ ID NO. 134/SEQ ID NO. 135, SEQ ID NO. 136/SEQ ID NO. 137, SEQ ID NO. 138/SEQ ID NO. 139, SEQ ID NO. 114/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 25/SEQ ID NO. 153, SEQ ID NO. 154/SEQ ID NO. 155, SEQ ID NO. 156/SEQ ID NO. 157, SEQ ID NO. 158/SEQ ID NO. 159, SEQ ID NO. 160/SEQ ID NO. 161, SEQ ID NO. 162/SEQ ID NO. 163, SEQ ID NO. 164/SEQ ID NO. 165, SEQ ID NO. 1664/SEQ ID NO. 167, SEQ ID NO. 168/SEQ ID NO. 169, SEQ ID NO. 170/SEQ ID NO. 171, SEQ ID NO. 172/SEQ ID NO. 173, SEQ ID NO. 174/SEQ ID NO. 175, SEQ ID NO. 176/SEQ ID NO. 177, SEQ ID NO. 19/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, and combinations thereof.

Preferably, the disease to be treated is selected from the group consisting of rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma) Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphederma, malaria, malignamt Lymphoma, malignant histiocytosis, malignant melanoma, meningitis, meningococcemia, metabolic/idiopathic, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), myasthenia gravis, mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occulsive arterial disorders, okt3 therapy, orchitis/epidymitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, and xenograft rejection of any organ or tissue.

BRIEF DESCRIPTION OF THE FIGURE

FIG. 1 shows the binding of various IgG1 clones over time.

DETAILED DESCRIPTION

The present disclosure provides a fully human antibody of an IgG class that binds to a CXCR5 epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called 52A9 herein), SEQ ID NO. 3/SEQ ID NO. 4 (called 52A10 herein), SEQ ID NO. 5/SEQ ID NO. 6 (called 52B10 herein), SEQ ID NO. 7/SEQ ID NO. 8 (called 52C6 herein), SEQ ID NO. 9/SEQ ID NO. 10 (called 52D6 herein), SEQ ID NO. 11/SEQ ID NO. 12 (called 52D7 herein), SEQ ID NO. 13/SEQ ID NO. 14 (called 52D11 herein), SEQ ID NO. 15/SEQ ID NO. 16 (called 52E1 herein), SEQ ID NO. 17/SEQ ID NO. 18 (called 52E10 herein), SEQ ID NO. 19/SEQ ID NO. 20 (called 52H9 herein), SEQ ID NO. 21/SEQ ID NO. 22 (called PC12 herein), SEQ ID NO. 23/SEQ ID NO. 24 (called PD10 herein), SEQ ID NO. 25/SEQ ID NO. 26 (called D3-4 herein), SEQ ID NO. 27/SEQ ID NO. 28 (called E2-1 herein), SEQ ID NO. 29/SEQ ID NO. 30 (called A4 or 7A7 herein), SEQ ID NO. 31/SEQ ID NO. 32 (called A8 herein), SEQ ID NO. 33/SEQ ID NO. 34 (called A12 herein), SEQ ID NO. 35/SEQ ID NO. 36 (called B3 herein), SEQ ID NO. 37/SEQ ID NO. 38 (called C8 herein), SEQ ID NO. 39/SEQ ID NO. 40 (called F8 or 10G9 herein), SEQ ID NO. 41/SEQ ID NO. 42 (called G11 herein), SEQ ID NO. 43/SEQ ID NO. 44 (called H3 herein), SEQ ID NO. 45/SEQ ID NO. 46 (called H5 herein), SEQ ID NO. 47/SEQ ID NO. 48 (called H6 herein), SEQ ID NO. 25/SEQ ID NO. 49 (called 2D3 herein), SEQ ID NO. 50/SEQ ID NO. 51 (called 3A11 herein), SEQ ID NO. 52/SEQ ID NO. 53 (called 3B9 herein), SEQ ID NO. 54/SEQ ID NO. 55 (called 3D11 herein), SEQ ID NO. 56/SEQ ID NO. 57 (called 3D12 or 4E12 herein), SEQ ID NO. 58/SEQ ID NO. 59 (called 3E7 herein), SEQ ID NO. 60/SEQ ID NO. 61 (called 3E12 herein), SEQ ID NO. 62/SEQ ID NO. 63 (called 3F7 herein), SEQ ID NO. 64/SEQ ID NO. 65 (called 3G2 herein), SEQ ID NO. 66/SEQ ID NO. 67 (called 3G7 herein), SEQ ID NO. 68/SEQ ID NO. 69 (called 4A5 herein), SEQ ID NO. 70/SEQ ID NO. 71 (called 4E9 herein), SEQ ID NO. 72/SEQ ID NO. 73 (called 4F1 herein), SEQ ID NO. 74/SEQ ID NO. 75 (called 4F4 herein), SEQ ID NO. 76/SEQ ID NO. 77 (called 4H2 herein), SEQ ID NO. 78/SEQ ID NO. 79 (called 5A8 herein), SEQ ID NO. 80/SEQ ID NO. 81 (called 5F1 herein), SEQ ID NO. 82/SEQ ID NO. 83 (called 6A4 herein), SEQ ID NO. 84/SEQ ID NO. 85 (called 6F9 herein), SEQ ID NO. 15/SEQ ID NO. 86 (called 6G5 herein), SEQ ID NO. 87/SEQ ID NO. 88 (called 7B11 or 8B2 herein), SEQ ID NO. 89/SEQ ID NO. 90 (called 7H10 herein), SEQ ID NO. 15/SEQ ID NO. 91 (called 8D12 herein), SEQ ID NO. 92/SEQ ID NO. 93 (called 8H5 herein), SEQ ID NO. 94/SEQ ID NO. 95 (called 9A10 herein), SEQ ID NO. 96/SEQ ID NO. 97 (called 10A12 herein), SEQ ID NO. 98/SEQ ID NO. 99 (called 10B2 herein), SEQ ID NO. 100/SEQ ID NO. 101 (called 10C3 herein), SEQ ID NO. 102/SEQ ID NO. 103 (called 10O7 herein), SEQ ID NO. 104/SEQ ID NO. 105 (called 11E3 herein), SEQ ID NO. 106/SEQ ID NO. 107 (called 11A12 herein), SEQ ID NO. 108/SEQ ID NO. 109 (called 11A7 herein), SEQ ID NO. 110/SEQ ID NO. 111 (called 11C3 herein), SEQ ID NO. 112/SEQ ID NO. 113 (called 11D3 herein), SEQ ID NO. 114/SEQ ID NO. 115 (called 11D4 herein), SEQ ID NO. 116/SEQ ID NO. 117 (called 11D7 herein), SEQ ID NO. 118/SEQ ID NO. 119 (called 11F3 herein), SEQ ID NO. 120/SEQ ID NO. 121 (called 11G3 herein), SEQ ID NO. 122/SEQ ID NO. 123 (called 12A4 herein), SEQ ID NO. 124/SEQ ID NO. 125 (called 12B11 or 14E10 herein), SEQ ID NO. 126/SEQ ID NO. 127 (called 12B4 herein), SEQ ID NO. 128/SEQ ID NO. 129 (called 12C1 herein), SEQ ID NO. 130/SEQ ID NO. 131 (called 12C6 herein), SEQ ID NO. 132/SEQ ID NO. 133 (called 12D11 herein), SEQ ID NO. 134/SEQ ID NO. 135 (called 12D3 herein), SEQ ID NO. 136/SEQ ID NO. 137 (called 12G10 herein), SEQ ID NO. 138/SEQ ID NO. 139 (called 13E10 herein), SEQ ID NO. 114/SEQ ID NO. 140 (called 13E4 herein), SEQ ID NO. 141/SEQ ID NO. 142 (called 13A3 herein), SEQ ID NO. 143/SEQ ID NO. 144 (called 13F8 herein), SEQ ID NO. 145/SEQ ID NO. 146 (called 13F9 herein), SEQ ID NO. 147/SEQ ID NO. 148 (called 13G9 herein), SEQ ID NO. 149/SEQ ID NO. 150 (called 14E5 herein), SEQ ID NO. 151/SEQ ID NO. 152 (called 14B11 herein), SEQ ID NO. 25/SEQ ID NO. 153 (called 14B4 herein), SEQ ID NO. 154/SEQ ID NO. 155 (called 14C10 herein), SEQ ID NO. 156/SEQ ID NO. 157 (called 14C11 herein), SEQ ID NO. 158/SEQ ID NO. 159 (called 14C3 herein), SEQ ID NO. 160/SEQ ID NO. 161 (called 14D7 herein), SEQ ID NO. 162/SEQ ID NO. 163 (called 14F11 herein), SEQ ID NO. 164/SEQ ID NO. 165 (called 14F8 herein), SEQ ID NO. 1664/SEQ ID NO. 167 (called 15C9 herein), SEQ ID NO. 168/SEQ ID NO. 169 (called 15D7 herein), SEQ ID NO. 170/SEQ ID NO. 171 (called 14D9 herein), SEQ ID NO. 172/SEQ ID NO. 173 (called 15F9 herein), SEQ ID NO. 174/SEQ ID NO. 175 (called 15G11 herein), SEQ ID NO. 176/SEQ ID NO. 177 (called 15G7 herein), SEQ ID NO. 19/SEQ ID NO. 178 (called 15G9 herein), SEQ ID NO. 179/SEQ ID NO. 180 (called 15H10 herein), SEQ ID NO. 181/SEQ ID NO. 182 (called 15H12 herein), SEQ ID NO. 183/SEQ ID NO. 184 (called 16E3 herein), SEQ ID NO. 185/SEQ ID NO. 186 (called 16A6 herein), SEQ ID NO. 187/SEQ ID NO. 188 (called 16A8 herein), SEQ ID NO. 189/SEQ ID NO. 190 (called 16B1 herein), SEQ ID NO. 191/SEQ ID NO. 192 (called 16B7 herein), SEQ ID NO. 193/SEQ ID NO. 194 (called 16F8 herein), SEQ ID NO. 195/SEQ ID NO. 196 (called 16F9 herein), and combinations thereof.

The present disclosure provides a fully human antibody Fab fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 25/SEQ ID NO. 49, SEQ ID NO. 50/SEQ ID NO. 51, SEQ ID NO. 52/SEQ ID NO. 53, SEQ ID NO. 54/SEQ ID NO. 55, SEQ ID NO. 56/SEQ ID NO. 57, SEQ ID NO. 58/SEQ ID NO. 59, SEQ ID NO. 60/SEQ ID NO. 61, SEQ ID NO. 62/SEQ ID NO. 63, SEQ ID NO. 64/SEQ ID NO. 65, SEQ ID NO. 66/SEQ ID NO. 67, SEQ ID NO. 68/SEQ ID NO. 69, SEQ ID NO. 70/SEQ ID NO. 71, SEQ ID NO. 72/SEQ ID NO. 73, SEQ ID NO. 74/SEQ ID NO. 75, SEQ ID NO. 76/SEQ ID NO. 77, SEQ ID NO. 78/SEQ ID NO. 79, SEQ ID NO. 80/SEQ ID NO. 81, SEQ ID NO. 82/SEQ ID NO. 83, SEQ ID NO. 84/SEQ ID NO. 85, SEQ ID NO. 15/SEQ ID NO. 86, SEQ ID NO. 87/SEQ ID NO. 88, SEQ ID NO. 89/SEQ ID NO. 90, SEQ ID NO. 15/SEQ ID NO. 91, SEQ ID NO. 92/SEQ ID NO. 93, SEQ ID NO. 94/SEQ ID NO. 95, SEQ ID NO. 96/SEQ ID NO. 97, SEQ ID NO. 98/SEQ ID NO. 99, SEQ ID NO. 100/SEQ ID NO. 101, SEQ ID NO. 102/SEQ ID NO. 103, SEQ ID NO. 104/SEQ ID NO. 105, SEQ ID NO. 106/SEQ ID NO. 107, SEQ ID NO. 108/SEQ ID NO. 109, SEQ ID NO. 110/SEQ ID NO. 111, SEQ ID NO. 112/SEQ ID NO. 113, SEQ ID NO. 114/SEQ ID NO. 115, SEQ ID NO. 116/SEQ ID NO. 117, SEQ ID NO. 118/SEQ ID NO. 119, SEQ ID NO. 120/SEQ ID NO. 121, SEQ ID NO. 122/SEQ ID NO. 123, SEQ ID NO. 124/SEQ ID NO. 125, SEQ ID NO. 126/SEQ ID NO. 127, SEQ ID NO. 128/SEQ ID NO. 129, SEQ ID NO. 130/SEQ ID NO. 131, SEQ ID NO. 132/SEQ ID NO. 133, SEQ ID NO. 134/SEQ ID NO. 135, SEQ ID NO. 136/SEQ ID NO. 137, SEQ ID NO. 138/SEQ ID NO. 139, SEQ ID NO. 114/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 25/SEQ ID NO. 153, SEQ ID NO. 154/SEQ ID NO. 155, SEQ ID NO. 156/SEQ ID NO. 157, SEQ ID NO. 158/SEQ ID NO. 159, SEQ ID NO. 160/SEQ ID NO. 161, SEQ ID NO. 162/SEQ ID NO. 163, SEQ ID NO. 164/SEQ ID NO. 165, SEQ ID NO. 1664/SEQ ID NO. 167, SEQ ID NO. 168/SEQ ID NO. 169, SEQ ID NO. 170/SEQ ID NO. 171, SEQ ID NO. 172/SEQ ID NO. 173, SEQ ID NO. 174/SEQ ID NO. 175, SEQ ID NO. 176/SEQ ID NO. 177, SEQ ID NO. 19/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 25/SEQ ID NO. 49, SEQ ID NO. 50/SEQ ID NO. 51, SEQ ID NO. 52/SEQ ID NO. 53, SEQ ID NO. 54/SEQ ID NO. 55, SEQ ID NO. 56/SEQ ID NO. 57, SEQ ID NO. 58/SEQ ID NO. 59, SEQ ID NO. 60/SEQ ID NO. 61, SEQ ID NO. 62/SEQ ID NO. 63, SEQ ID NO. 64/SEQ ID NO. 65, SEQ ID NO. 66/SEQ ID NO. 67, SEQ ID NO. 68/SEQ ID NO. 69, SEQ ID NO. 70/SEQ ID NO. 71, SEQ ID NO. 72/SEQ ID NO. 73, SEQ ID NO. 74/SEQ ID NO. 75, SEQ ID NO. 76/SEQ ID NO. 77, SEQ ID NO. 78/SEQ ID NO. 79, SEQ ID NO. 80/SEQ ID NO. 81, SEQ ID NO. 82/SEQ ID NO. 83, SEQ ID NO. 84/SEQ ID NO. 85, SEQ ID NO. 15/SEQ ID NO. 86, SEQ ID NO. 87/SEQ ID NO. 88, SEQ ID NO. 89/SEQ ID NO. 90, SEQ ID NO. 15/SEQ ID NO. 91, SEQ ID NO. 92/SEQ ID NO. 93, SEQ ID NO. 94/SEQ ID NO. 95, SEQ ID NO. 96/SEQ ID NO. 97, SEQ ID NO. 98/SEQ ID NO. 99, SEQ ID NO. 100/SEQ ID NO. 101, SEQ ID NO. 102/SEQ ID NO. 103, SEQ ID NO. 104/SEQ ID NO. 105, SEQ ID NO. 106/SEQ ID NO. 107, SEQ ID NO. 108/SEQ ID NO. 109, SEQ ID NO. 110/SEQ ID NO. 111, SEQ ID NO. 112/SEQ ID NO. 113, SEQ ID NO. 114/SEQ ID NO. 115, SEQ ID NO. 116/SEQ ID NO. 117, SEQ ID NO. 118/SEQ ID NO. 119, SEQ ID NO. 120/SEQ ID NO. 121, SEQ ID NO. 122/SEQ ID NO. 123, SEQ ID NO. 124/SEQ ID NO. 125, SEQ ID NO. 126/SEQ ID NO. 127, SEQ ID NO. 128/SEQ ID NO. 129, SEQ ID NO. 130/SEQ ID NO. 131, SEQ ID NO. 132/SEQ ID NO. 133, SEQ ID NO. 134/SEQ ID NO. 135, SEQ ID NO. 136/SEQ ID NO. 137, SEQ ID NO. 138/SEQ ID NO. 139, SEQ ID NO. 114/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 25/SEQ ID NO. 153, SEQ ID NO. 154/SEQ ID NO. 155, SEQ ID NO. 156/SEQ ID NO. 157, SEQ ID NO. 158/SEQ ID NO. 159, SEQ ID NO. 160/SEQ ID NO. 161, SEQ ID NO. 162/SEQ ID NO. 163, SEQ ID NO. 164/SEQ ID NO. 165, SEQ ID NO. 1664/SEQ ID NO. 167, SEQ ID NO. 168/SEQ ID NO. 169, SEQ ID NO. 170/SEQ ID NO. 171, SEQ ID NO. 172/SEQ ID NO. 173, SEQ ID NO. 174/SEQ ID NO. 175, SEQ ID NO. 176/SEQ ID NO. 177, SEQ ID NO. 19/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, and combinations thereof.

The present disclosure further provides a method for treating a broad spectrum of mammalian cancers or inflammatory diseases or autoimmune diseases, comprising administering an effective amount of an anti-CXCR5 polypeptide, wherein the anti-CXCR5 polypeptide is selected from the group consisting of a fully human antibody of an IgG class that binds to a CXCR5 epitope with a binding affinity of at least $10^{-6}$M, a fully human antibody Fab fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 87, SEQ ID NO. 89, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 141, SEQ ID NO. 143, SEQ ID NO. 145, SEQ ID NO. 147, SEQ ID NO. 149, SEQ ID NO. 151, SEQ ID NO. 154, SEQ ID NO. 156, SEQ ID NO. 158, SEQ ID NO. 160, SEQ ID NO. 162, SEQ ID NO. 164, SEQ ID NO. 176, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 86, SEQ ID NO. 88, SEQ ID NO. 90, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 25/SEQ ID NO. 49, SEQ ID NO. 50/SEQ ID NO. 51, SEQ ID NO. 52/SEQ ID NO. 53, SEQ ID NO. 54/SEQ ID NO. 55, SEQ ID NO. 56/SEQ ID NO. 57, SEQ ID NO. 58/SEQ ID NO. 59, SEQ ID NO. 60/SEQ ID NO. 61, SEQ ID NO. 62/SEQ ID NO. 63, SEQ ID NO. 64/SEQ ID NO. 65, SEQ ID NO. 66/SEQ ID NO. 67, SEQ ID NO. 68/SEQ ID NO. 69, SEQ ID NO. 70/SEQ ID NO. 71, SEQ ID NO. 72/SEQ ID NO. 73, SEQ ID NO. 74/SEQ ID NO. 75, SEQ ID NO. 76/SEQ ID NO. 77, SEQ ID NO. 78/SEQ ID NO. 79, SEQ ID NO. 80/SEQ ID NO. 81, SEQ ID NO. 82/SEQ ID NO. 83, SEQ ID NO. 84/SEQ ID NO. 85, SEQ ID NO. 15/SEQ ID NO. 86, SEQ ID NO. 87/SEQ ID NO. 88, SEQ ID NO. 89/SEQ ID NO. 90, SEQ ID NO. 15/SEQ ID NO. 91, SEQ ID NO. 92/SEQ ID NO. 93, SEQ ID NO. 94/SEQ ID NO. 95, SEQ ID NO. 96/SEQ ID NO. 97, SEQ ID NO. 98/SEQ ID NO. 99, SEQ ID NO. 100/SEQ ID NO. 101, SEQ ID NO. 102/SEQ ID NO. 103, SEQ ID NO. 104/SEQ ID NO. 105, SEQ ID NO. 106/SEQ ID NO. 107, SEQ ID NO. 108/SEQ ID NO. 109, SEQ ID NO. 110/SEQ ID NO. 111, SEQ ID NO. 112/SEQ ID NO. 113, SEQ ID NO. 114/SEQ ID NO. 115, SEQ ID NO. 116/SEQ ID NO. 117, SEQ ID NO. 118/SEQ ID NO. 119, SEQ ID NO. 120/SEQ ID NO. 121, SEQ ID NO. 122/SEQ ID NO. 123, SEQ ID NO. 124/SEQ ID NO. 125, SEQ ID NO. 126/SEQ ID NO. 127, SEQ ID NO. 128/SEQ ID NO. 129, SEQ ID NO. 130/SEQ ID NO. 131, SEQ ID NO. 132/SEQ ID NO. 133, SEQ ID NO. 134/SEQ ID NO. 135, SEQ ID NO. 136/SEQ ID NO. 137, SEQ ID NO. 138/SEQ ID NO. 139, SEQ ID NO. 114/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 25/SEQ ID NO. 153, SEQ ID NO. 154/SEQ ID NO. 155, SEQ ID NO. 156/SEQ ID NO. 157, SEQ ID NO. 158/SEQ ID NO. 159, SEQ ID NO. 160/SEQ ID NO. 161, SEQ ID NO. 162/SEQ ID NO. 163, SEQ ID NO. 164/SEQ ID NO. 165, SEQ ID NO. 1664/SEQ ID NO. 167, SEQ ID NO. 168/SEQ ID NO. 169, SEQ ID NO. 170/SEQ ID NO. 171, SEQ ID NO. 172/SEQ ID NO. 173, SEQ ID NO. 174/SEQ ID NO. 175, SEQ ID NO. 176/SEQ ID NO. 177, SEQ ID NO. 19/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 25/SEQ ID NO. 49, SEQ ID NO. 50/SEQ ID NO. 51, SEQ ID NO. 52/SEQ ID NO. 53, SEQ ID NO. 54/SEQ ID NO. 55, SEQ ID NO. 56/SEQ ID NO. 57, SEQ ID NO. 58/SEQ ID NO. 59, SEQ ID NO. 60/SEQ ID NO. 61, SEQ ID NO. 62/SEQ ID NO. 63, SEQ ID NO. 64/SEQ ID NO. 65, SEQ ID NO. 66/SEQ ID NO. 67, SEQ ID NO. 68/SEQ ID NO. 69, SEQ ID NO. 70/SEQ ID NO. 71, SEQ ID NO. 72/SEQ ID NO. 73, SEQ ID NO. 74/SEQ ID NO. 75, SEQ ID NO. 76/SEQ ID NO. 77, SEQ ID NO. 78/SEQ ID NO. 79, SEQ ID NO. 80/SEQ ID NO. 81, SEQ ID NO. 82/SEQ ID NO. 83, SEQ ID NO. 84/SEQ ID NO. 85, SEQ ID NO. 15/SEQ ID NO. 86, SEQ ID NO. 87/SEQ ID NO. 88, SEQ ID NO. 89/SEQ ID NO. 90, SEQ ID NO. 15/SEQ ID NO. 91, SEQ ID NO. 92/SEQ ID NO. 93, SEQ ID NO. 94/SEQ ID NO. 95, SEQ ID NO. 96/SEQ ID NO. 97, SEQ ID NO. 98/SEQ ID NO. 99, SEQ ID NO. 100/SEQ ID NO. 101, SEQ ID NO. 102/SEQ ID NO. 103, SEQ ID NO. 104/SEQ ID NO. 105, SEQ ID NO. 106/SEQ ID NO. 107, SEQ ID NO. 108/SEQ ID NO. 109, SEQ ID NO. 110/SEQ ID NO. 111, SEQ ID NO. 112/SEQ ID NO. 113, SEQ ID NO. 114/SEQ ID NO. 115, SEQ ID NO. 116/SEQ ID NO. 117, SEQ ID NO. 118/SEQ ID NO. 119, SEQ ID NO. 120/SEQ ID NO. 121, SEQ ID NO. 122/SEQ ID NO. 123, SEQ ID NO. 124/SEQ ID NO. 125, SEQ ID NO. 126/SEQ ID NO. 127, SEQ ID NO. 128/SEQ ID NO. 129, SEQ ID NO. 130/SEQ ID NO. 131, SEQ ID NO. 132/SEQ ID NO. 133, SEQ ID NO. 134/SEQ ID NO. 135, SEQ ID NO. 136/SEQ ID NO. 137, SEQ ID NO. 138/SEQ ID NO. 139, SEQ ID NO. 114/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 25/SEQ ID NO. 153, SEQ ID NO. 154/SEQ ID NO. 155, SEQ ID NO. 156/SEQ ID NO. 157, SEQ ID NO. 158/SEQ ID NO. 159, SEQ ID NO. 160/SEQ ID NO. 161, SEQ ID NO. 162/SEQ ID NO. 163, SEQ ID NO. 164/SEQ ID NO. 165, SEQ ID NO. 1664/SEQ ID NO. 167, SEQ ID NO. 168/SEQ ID NO. 169, SEQ ID NO. 170/SEQ ID NO. 171, SEQ ID NO. 172/SEQ ID NO. 173, SEQ ID NO. 174/SEQ ID NO. 175, SEQ ID NO. 176/SEQ ID NO. 177, SEQ ID NO. 19/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 25/SEQ ID NO. 49, SEQ ID NO. 50/SEQ ID NO. 51, SEQ ID NO. 52/SEQ ID NO. 53, SEQ ID NO. 54/SEQ ID NO. 55, SEQ ID NO. 56/SEQ ID NO. 57, SEQ ID NO. 58/SEQ ID NO. 59, SEQ ID NO. 60/SEQ ID NO. 61, SEQ ID NO. 62/SEQ ID NO. 63, SEQ ID NO. 64/SEQ ID NO. 65, SEQ ID NO. 66/SEQ ID NO. 67, SEQ ID NO. 68/SEQ ID NO. 69, SEQ ID NO. 70/SEQ ID NO. 71, SEQ ID NO. 72/SEQ ID NO. 73, SEQ ID NO. 74/SEQ ID NO. 75, SEQ ID NO. 76/SEQ ID NO. 77, SEQ ID NO. 78/SEQ ID NO. 79, SEQ ID NO. 80/SEQ ID NO. 81, SEQ ID NO. 82/SEQ ID NO. 83, SEQ ID NO. 84/SEQ ID NO. 85, SEQ ID NO. 15/SEQ ID NO. 86, SEQ ID NO. 87/SEQ ID NO. 88, SEQ ID NO. 89/SEQ ID NO. 90, SEQ ID NO. 15/SEQ ID NO. 91, SEQ ID NO. 92/SEQ ID NO. 93, SEQ ID NO. 94/SEQ ID NO. 95, SEQ ID NO. 96/SEQ ID NO. 97, SEQ ID NO. 98/SEQ ID NO. 99, SEQ ID NO. 100/SEQ ID NO. 101, SEQ ID NO. 102/SEQ ID NO. 103, SEQ ID NO. 104/SEQ ID NO. 105, SEQ ID NO. 106/SEQ ID NO. 107, SEQ ID NO. 108/SEQ ID NO. 109, SEQ ID NO. 110/SEQ ID NO. 111, SEQ ID NO. 112/SEQ ID NO. 113, SEQ ID NO. 114/SEQ ID NO. 115, SEQ ID NO. 116/SEQ ID NO. 117, SEQ ID NO. 118/SEQ ID NO. 119, SEQ ID NO. 120/SEQ ID NO. 121, SEQ ID NO. 122/SEQ ID NO. 123, SEQ ID NO. 124/SEQ ID NO. 125, SEQ ID NO. 126/SEQ ID NO. 127, SEQ ID NO. 128/SEQ ID NO. 129, SEQ ID NO. 130/SEQ ID NO. 131, SEQ ID NO. 132/SEQ ID NO. 133, SEQ ID NO. 134/SEQ ID NO. 135, SEQ ID NO. 136/SEQ ID NO. 137, SEQ ID NO. 138/SEQ ID NO. 139, SEQ ID NO. 114/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 25/SEQ ID NO. 153, SEQ ID NO. 154/SEQ ID NO. 155, SEQ ID NO. 156/SEQ ID NO. 157, SEQ ID NO. 158/SEQ ID NO. 159, SEQ ID NO. 160/SEQ ID NO. 161, SEQ ID NO. 162/SEQ ID NO. 163, SEQ ID NO. 164/SEQ ID NO. 165, SEQ ID NO. 1664/SEQ ID NO. 167, SEQ ID NO. 168/SEQ ID NO. 169, SEQ ID NO. 170/SEQ ID NO. 171, SEQ ID NO. 172/SEQ ID NO. 173, SEQ ID NO. 174/SEQ ID NO. 175, SEQ ID NO. 176/SEQ ID NO. 177, SEQ ID NO. 19/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, and combinations thereof.

Preferably, the broad spectrum of mammalian cancers to be treated the cancer is an CXCR5-positive cancer. Preferably, the broad spectrum of mammalian cancers to be treated is selected from the group consisting of cancinomas, prostate cancer, non-small cell lung cancer, breast cancer, endometrial cancer, ovarian cancer, gastric cancers, head and neck cancers, and colon cancer.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, Dev. Comp. Immunol. 29:185-203; 2005) and AHo (Honegger and Pluckthun, J. Mol. Biol. 309(3):657-670; 2001).

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or VL domain (U.S. Pat. Nos. 6,846,634; 6,696,245, US Patent Applications 2002/02512; 2004/0202995; 2004/0038291; 2004/0009507; 2003/0039958, and Ward et al., Nature 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (Bird et al., 1988, Science 242:423-26 and Huston et al., 1988, Proc. Natl. Acad. Sci. USA 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

Further, the framework regions may be derived from one of the same anti-CXCR5 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody(-ies) from another species or belonging to another antibody class or subclass. Also included are fragments of such antibodies that exhibit the desired biological activity (i.e., the ability to specifically bind CXCR5).

A "neutralizing antibody" or an "inhibitory antibody" is an antibody that inhibits the activation of CXCR5 when an excess of the anti-CXCR5 antibody reduces the amount of activation by at least about 20% using an assay such as those described herein in the Examples. In various embodiments, the antigen binding protein reduces the amount of amount of activation of CXCR5 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CXCR5) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

95% Homology

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)). Near et al. *Mol. Immunol.* 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2).

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

CXCR5-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one specific embodiment, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$-1CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

Although PEG is well-known, this is the first demonstration that a pegylated $^{10F}$n3 polypeptide can be pegylated and retain ligand binding activity. In a preferred embodiment, the pegylated $^{10F}$n3 polypeptide is produced by site-directed pegylation, particularly by conjugation of PEG to a cysteine moiety at the N- or C-terminus. Accordingly, the present disclosure provides a target-binding $^{10F}$n3 polypeptide with improved pharmacokinetic properties, the polypeptide comprising: a $^{10F}$n3 domain having from about 80 to about 150 amino acids, wherein at least one of the loops of said $^{10F}$n3 domain participate in target binding; and a covalently bound PEG moiety, wherein said $^{10F}$n3 polypeptide binds to the target with a $K_D$ of less than 100 nM and has a clearance rate of less than 30 mL/hr/kg in a mammal. The PEG moiety may be attached to the $^{10F}$n3 polypeptide by site directed pegylation, such as by attachment to a Cys residue, where the Cys residue may be positioned at the N-terminus of the $^{10F}$n3 polypeptide or between the N-terminus and the most N-terminal beta or beta-like strand or at the C-terminus of the $^{10F}$n3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., *J. Biol. Chem.*, 252, 3571 (1977) and *J. Biol. Chem.*, 252, 3582 (1977), Zalipsky, et al., and Harris et. al., in: *Poly(ethylene glycol) Chemistry: Biotechnical and Biomedical Applications*; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

A variety of molecular mass forms of PEG can be selected, e.g., from about 1,000 Daltons (Da) to 100,000 Da (n is 20 to 2300), for conjugating to CXCR5-binding polypeptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the disclosure an CXCR5 binding polypeptide is covalently linked to one poly(ethylene glycol) group of the formula: —CO—$(CH_2)_x$—$(OCH_2CH_2)_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's ε-amino group of a lysine is the available (free) amino group.

The above conjugates may be more specifically presented by formula (II): P—NHCO—$(CH_2)_x$—$(OCH_2CH_2)_m$—OR (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group.

In another embodiment, the pegylated binding polypeptides of the invention will preferably retain at least 25%, 50%, 60%, 70%, 80%, 85%, 90%, 95% or 100% of the biological activity associated with the unmodified protein. In one embodiment, biological activity refers to its ability to bind to CXCR5, as assessed by KD, $k_{on}$ or $k_{off}$. In one specific embodiment, the pegylated binding polypeptide protein shows an increase in binding to CXCR5 relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Formulations and Modes of Administration

The present disclosure features methods for treating conditions or preventing pre-conditions which respond to an inhibition of CXCR5 biological activity. Preferred examples are conditions that are characterized by inflammation or cellular hyperproliferation. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Exemplary Uses

The CXCR5 binding proteins described herein and their related variants are useful in a number of therapeutic and diagnostic applications. These include the inhibition of the biological activity of CXCR5 by competing for or blocking the binding to a CXCR5 as well as the delivery of cytotoxic or imaging moieties to cells, preferably cells expressing CXCR5. The small size and stable structure of these molecules can be particularly valuable with respect to manufacturing of the drug, rapid clearance from the body for certain applications where rapid clearance is desired or formulation into novel delivery systems that are suitable or improved using a molecule with such characteristics.

On the basis of their efficacy as inhibitors of CXCR5 biological activity, the polypeptides of this disclosure are effective against a number of cancer conditions as well as complications arising from cancer, such as pleural effusion and ascites, colorectal cancers, head and neck cancers, small cell lung cancer, non-small cell lung cancer (NSCLC) and pancreatic cancer. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer.

In certain embodiments, the subject anti-CXCR5 antibodies agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

Depending on the nature of the combinatory therapy, administration of the polypeptide therapeutic agents may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

In one example of a diagnostic application, a biological sample, such as serum or a tissue biopsy, from a patient suspected of having a condition characterized by inappropriate angiogenesis is contacted with a detectably labeled polypeptide of the disclosure to detect levels of CXCR5. The levels of CXCR5 detected are then compared to levels of CXCR5 detected in a normal sample also contacted with the labeled polypeptide. An increase of at least 10%, 20%, 30%, 40%, 50%, 60%, 70%, 80%, or 90% in the levels of the CXCR5 may be considered a diagnostic indicator.

In certain embodiments, the CXCR5 binding polypeptides are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. Immunoscintigraphy using CXCR5 binding polypeptides directed at CXCR5 may be used to detect and/or diagnose cancers and vasculature. For example, any of the binding polypeptide against a CXCR5 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The CXCR5 binding polypeptides can also be used to deliver additional therapeutic agents (including but not limited to drug compounds, chemotherapeutic compounds, and radiotherapeutic compounds) to a cell or tissue expressing CXCR5. In one example, the CXCR5 binding polypeptide is fused to a chemotherapeutic agent for targeted delivery of the chemotherapeutic agent to a tumor cell or tissue expressing CXCR5.

The CXCR5 binding polypeptides are useful in a variety of applications, including research, diagnostic and therapeutic applications. For instance, they can be used to isolate and/or purify receptor or portions thereof, and to study receptor structure (e.g., conformation) and function.

In certain embodiments, the binding polypeptides of fragments thereof can be labeled or unlabeled for diagnostic purposes. Typically, diagnostic assays entail detecting the formation of a complex resulting from the binding of a binding polypeptide to CXCR5. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a CXCR5 protein is combined with the subject binding polypeptides, binding occurs between the binding polypeptides and the CXCR5 protein. In one embodiment, a sample containing cells expressing a CXCR5 protein (e.g., endothelial cells) is combined with the subject antibodies, and binding occurs between the binding polypeptides and cells bearing a CXCR5 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a CXCR5 protein in a biological sample can also be prepared. Such kits will include a CXCR5 binding polypeptide which binds to a CXCR5 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present disclosure also provides a method of detecting and/or quantitating expression of CXCR5, wherein a composition comprising a cell or fraction thereof (e.g., membrane fraction) is contacted with a binding polypeptide which binds to a CXCR5 or portion of the receptor under conditions appropriate for binding thereto, and the binding is monitored. Detection of the binding polypeptide, indicative of the formation of a complex between binding polypeptide and CXCR5 or a portion thereof, indicates the presence of the receptor. Binding of a polypeptide to the cell can be determined by standard methods, such as those described in the working examples. The method can be used to detect expression of CXCR5 on cells from an individual. Optionally, a quantitative expression of CXCR5 on the surface of endothelial cells can be evaluated, for instance, by flow cytometry, and the staining intensity can be correlated with disease susceptibility, progression or risk.

The present disclosure also provides a method of detecting the susceptibility of a mammal to certain diseases. To illustrate, the method can be used to detect the susceptibility of a mammal to diseases which progress based on the amount of CXCR5 present on cells and/or the number of CXCR5-positive cells in a mammal.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

Antigen Binding Proteins

Antigen binding proteins (e.g., antibodies, antibody fragments, antibody derivatives, antibody muteins, and antibody variants) are polypeptides that bind to EGFR, (preferably, human CXCR5). Antigen binding proteins include antigen binding proteins that inhibit a biological activity of CXCR5.

Oligomers that contain one or more antigen binding proteins may be employed as CXCR5 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have CXCR5 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a CXCR5 binding fragment of an anti-CXCR5 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of *facile* purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-CXCR5 antibody fragment or derivative fused to a leucine zipper peptide are expressed in suitable host cells, and the soluble oligomeric anti-CXCR5 antibody fragments or derivatives that form are recovered from the culture supernatant.

Antigen-binding fragments of antigen binding proteins of the invention may be produced by conventional techniques. Examples of such fragments include, but are not limited to, Fab and F(ab')$_2$ fragments.

The present disclosure provides monoclonal antibodies that bind to CXCR5. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against CXCR5 can be used, for example, in assays to detect the presence of CXCR5 polypeptides, either in vitro or in vivo. The antigen binding proteins also may be employed in purifying CXCR5 proteins by immunoaffinity chromatography. Blocking antigen binding proteins can be used in the methods disclosed herein. Such antigen binding proteins that function as CXCR5 antagonists may be employed in treating any CXCR5-induced condition, including but not limited to various cancers.

Antigen binding proteins may be employed in an in vitro procedure, or administered in vivo to inhibit CXCR5-induced biological activity. Disorders caused or exacerbated (directly or indirectly) by the proteolytic activation of CXCR5, examples of which are provided herein, thus may be treated. In one embodiment, the present invention provides a therapeutic method comprising in vivo administration of a CXCR5 blocking antigen binding protein to a mammal in need thereof in an amount effective for reducing a CXCR5-induced biological activity.

Antigen binding proteins include fully human monoclonal antibodies that inhibit a biological activity of CXCR5.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of CXCR5 bound thereto. Polypeptides contemplated for use herein include substantially homogeneous recombinant mammalian anti-CXCR5 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-CXCR5 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, Methods Mol. Biol. 178:303-16). Moreover, if an IgG4 is desired, it may also be desired to introduce a point mutation (CPSCP→CPPCP) in the hinge region (Bloom et al., 1997, Protein Science 6:407) to alleviate a tendency to form intra-H chain disulfide bonds that can lead to heterogeneity in the IgG4 antibodies.

In particular embodiments, antigen binding proteins of the present invention have a binding affinity ($K_a$) for CXCR5 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from CXCR5. In one embodiment, the antigen binding protein has a $K_{off}$ of $1 \times 10^{-4}$ to $^{-1}$ or lower. In another embodiment, the $K_{off}$ is $5 \times 10^{-5}$ to $^{-1}$ or lower. In another embodiment, the $K_{off}$ is substantially the same as an antibody described herein. In another embodiment, the antigen binding protein binds to CXCR5 with substantially the same $K_{off}$ as an antibody described herein.

In another aspect, the present disclosure provides an antigen binding protein that inhibits an activity of CXCR5. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of CXCR5 with substantially the same $IC_{50}$ as an antibody described herein.

In another aspect, the present disclosure provides an antigen binding protein that binds to human CXCR5 expressed on the surface of a cell and, when so bound, inhibits CXCR5 signaling activity in the cell without causing a significant reduction in the amount of CXCR5 on the surface of the cell. Any method for determining or estimating the amount of CXCR5 on the surface and/or in the interior of the cell can be used. In other embodiments, binding of the antigen binding protein to the CXCR5-expressing cell causes less than about 75%, 50%, 40%, 30%, 20%, 15%, 10%, 5%, 1%, or 0.1% of the cell-surface CXCR5 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of CXCR5, or to an epitope of CXCR5 and an epitope of another molecule, via two different antigen binding sites or regions. Moreover, bispecific antigen binding protein as disclosed herein can comprise an CXCR5 binding site from one of the herein-described antibodies and a second CXCR5 binding region from another of the herein-described antibodies, including those described herein by reference to other publications. Alternatively, a bispecific antigen binding protein may comprise an antigen binding site from one of the herein described antibodies and a second antigen binding site from another CXCR5 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. No. 5,959,083; and U.S. Pat. No. 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Therapeutic Methods and Administration of Antigen Binding Proteins

Certain methods provided herein comprise administering a CXCR5 binding antigen binding protein to a subject, thereby reducing a CXCR5-induced biological response that plays a role in a particular condition. In particular embodiments, methods of the invention involve contacting endogenous CXCR5 with an CXCR5 binding antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient a CXCR5 antagonist in an amount and for a time sufficient to induce a sustained improvement over baseline of an indicator that reflects the severity of the particular disorder.

Use of antigen binding proteins in ex vivo procedures also is contemplated. For example, a patient's blood or other bodily fluid may be contacted with an antigen binding protein that binds CXCR5 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to an EGFR binding antigen binding protein Combination Therapy In another aspect, the present disclosure provides a method of treating a subject with an CXCR5 inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue.

In another embodiment, a combination therapy method comprises administering to the subject two, three, four, five, six, or more of the CXCR5 agonists or antagonists described herein. In another embodiment, the method comprises administering to the subject two or more treatments that together inhibit or activate (directly or indirectly) CXCR5-mediated signal transduction. Examples of such methods include using combinations of two or more CXCR5 inhibiting antigen binding proteins, of an CXCR5 inhibiting antigen binding protein and one or more other therapeutic moiety having anti-cancer properties (for example, cytotoxic agents, and/or immunomodulators), or of an CXCR5 inhibiting antigen binding protein and one or more other treatments (e.g., surgery, or radiation). Furthermore, one or more anti-CXCR5 antibodies or antibody derivatives can be used in combination with one or more molecules or other treatments, wherein the other molecule(s) and/or treatment(s) do not directly bind to or affect CXCR5, but which combination is effective for treating or preventing the condition being treated. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the CXCR5 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

Example 1

This example describes a cellular binding assay to determine the $EC_{50}$ for anti-CXCR5 antibodies binding to human CXCR5. This example shows the binding characteristics for these antibodies in terms of the maximal cell binding and the concentration at which 50% binding saturation ($EC_{50}$) is reached. In this example, CHO-CXCR5 cells were lifted from culture flasks using non-enzymatic Cell Dissociation Buffer—PBS based (Life Technologies #13151-014). Cells were resuspended in FACS Buffer (2% Fetal Bovine Serum in PBS) at $1\times10^6$ cells/ml and 50 ($0.5\times10^5$ cells) were aliquoted into the wells of a 96-well plate. Plated cells were spun down and the supernatant discarded. Cells were resuspended in 30 µl FACS Buffer serially diluted concentrations of CXCR5 IgG in triplicate. Plates were incubated for 1 hr at 4° C. and then washed 2× with FACS Buffer. Cells were resuspended in 50 µl goat anti-human IgG (γ-chain specific)-PE conjugated secondary antibody (Southern Biotech #2040-09) diluted 1:500 in FACS Buffer. Cells were further incubated for 30 min at 4° C. and then washed 1× with FACS Buffer. The cells were resuspended in a final volume of 30 µl FACS Buffer and analyzed using the Intellicyt Flow Cytometer. Median fluorescence in the FL-2H channel was determined using FlowJo software and $EC_{50}$ value was determined by plotting the data in GraphPad Prism and analyzing using a variable slope non-linear regression. The results are shown in Table 1.

TABLE 1

$EC_{50}$ of anti-CXCR5 antibodies to human CXCR5.

| Name | EC50 (nM), hu-CHO |
|---|---|
| 4C10 | 0.7 |
| 11A7 | 0.9 |
| 11D3 | 2.7 |
| 11E3-0 | 10 |
| 11E3 | 1.8 |
| 11G3 | 2.6 |
| 12C1 | 12 |
| 12D3 | 1.3 |
| 12D11 | 2.1 |
| 12G10 | 0.5 |
| 13A3 | 7.4 |

TABLE 1-continued $EC_{50}$ of anti-CXCR5 antibodies to human CXCR5.

| Name | EC50 (nM), hu-CHO |
|---|---|
| 13E4 | 0.9 |
| 13E10 | 0.7 |
| 13F9 | 1.6 |
| 13G9 | 3 |
| 14B11 | 10 |
| 14C10 | 0.7 |
| 14C11 | 21 |
| 14D7 | 4 |
| 14D9 | 22 |
| 14E5 | 0.3 |
| 14F8 | 2.5 |
| 14F11 | 3.8 |
| 15G11 | 0.4 |
| 15H2 | 6.1 |
| 16A8 | 2.3 |
| 16F8 | 3.6 |
| 16F9 | 0.7 |
| 52A10 | 0.5 |
| 52B10 | 0.5 |
| 52C6 | 3 |
| 16E3 | 250 |
| 15H10 | 132 |
| 11F3 | 13 |
| 16A6 | 37 |
| 12B11 | 53 |
| 16B7 | 88 |
| 14E10 | 57 |
| 14C3 | 21 |
| PC12 | 4.2 |
| 52D6 | 24 |
| 52A9* | 31 |
| 52B10 | 0.46 |
| 52C6 | 2.8 |
| 52H9 | 4 |
| 52A10 | 0.54 |

N/A = little detectable binding.

Example 2

This example shows a cellular binding assay to determine the $EC_{50}$ for anti-CXCR5 antibodies binding to murine CXCR5. This example shows the binding characteristics for these antibodies in terms of the maximal cell binding and the concentration at which 50% binding saturation ($EC_{50}$) is reached. In this example, mouse spleen cells were harvested from either C57Bl/6 or athymic nu/nu mice. Cells were cultured at $2\times10^6$ per ml with LPS at 10 micrograms per ml in RPMI+10% FCS for up to 4 days at 37° C. in 5% CO2. Cells were harvested, washed and resuspended in FACS Buffer (2% Fetal Bovine Serum in PBS) at $1\times10^6$ cells/ml and 50 µl ($0.5\times10^5$ cells) were aliquoted into the wells of a 96-well plate. Plated cells were spun down and the supernatant discarded. Cells were resuspended in 30 µl FACS Buffer containing serially diluted concentrations of CXCR5 IgG in triplicate. Plates were incubated for 1 hr at 4° C. and then washed 2× with FACS Buffer. Cells were resuspended in 50 µl goat anti-human IgG (γ-chain specific)-PE conjugated secondary antibody (Southern Biotech #2040-09) diluted 1:500 in FACS Buffer. Cells were further incubated for 30 min at 4° C. and then washed 1× with FACS Buffer. The cells were resuspended in a final volume of 30 µl FACS Buffer and analyzed using the Intellicyt Flow Cytometer. Median fluorescence in the FL-2H channel was determined using FlowJo software and $EC_{50}$ value was determined by plotting the data in GraphPad Prism and analyzing using a variable slope non-linear regression. The results are shown in Table 2.

TABLE 2

EC50 of anti-CXCR5 antibodies to murine CXCR5.

| Name | EC50 (nM), mur |
|---|---|
| 11A7 | >100 |
| 11D3 | N/A |
| 11E3 | 11 |
| 11G3 | 37 |
| 12C1 | N/A |
| 12D3 | 27 |
| 12D11 | N/A |
| 12G10 | 2.5 |
| 13E4 | 5.5 |
| 13E10 | 25 |
| 13F9 | 23 |
| 13G9 | >50 |
| 14B11 | N/A |
| 14C10 | 375 |
| 14E5 | 2.8 |
| 14F11 | N/A |
| 15G11 | 4.8 |
| 16A8 | >100 |
| 16F8 | 15 |
| 16F9 | 3.1 |
| 12B11 | N/A |
| 16B7 | N/A |

N/A = little detectable binding.

Example 3

In this example, CHO-CXCR5 cells were lifted from culture flasks using non-enzymatic Cell Dissociation Buffer—PBS based (Life Technologies #13151-014). Cells were resuspended in FACS Buffer (2% Fetal Bovine Serum in PBS) with sodium azide at 1×10$^6$ cells/ml and 800 were aliquoted into a tube for each antibody. Antibody was added to a final concentration of 5 µg/ml and incubated at room temperature for 1 h. The samples were then placed on ice and a 105 aliquot at various time points was removed and added to 190 µl FACS buffer in a 96-well plate and centrifuged for 3 min. Supernatant was discarded, the cells were resuspended in 105 µl of FACS buffer, aliquoted (50 µl) in duplicates into another 96-well plate containing 150 µl FACS buffer and incubated at room temperature. After all of the time points were collected, the plate was centrifuged for 3 min, supernatant discarded and the cells were resuspended in 50 µl goat anti-human IgG (γ-chain specific)-PE conjugated secondary antibody (Southern Biotech #2040-09) diluted 1:500 in FACS Buffer. Cells were further incubated for 30 min at 4° C. and then washed 1× with FACS Buffer. The cells were resuspended in a final volume of 30 µl FACS Buffer and analyzed using the Intellicyt Flow Cytometer. The binding of various IgG1 clones over time is shown in FIG. 1.

Example 4

This example shows a Calcium assay with CHO-CXCR5 cells. CHO-CXCR5 cells (CHO cells transfected with human CXCR5 gene) were used in the calcium assay. Cells (0.1×10$^5$) were seeded in 20 µl of growth medium per well of a 384 well plate (#781091, Greiner) and incubated for 20 hours. The growth medium is F-12K (#21127, Life Technologies) plus 10% FBS. Serial diluted doses of mAbs (5 µl) were added into 20 µl cells and incubated 20 min at room temperature. Then, 25 µl of Calcium 4 Assay kit reagent (R8142, Molecular Devices), including 0.5 mM probenecid (Sigma #P8761-25G), were added to the 25 µl cells pre-incubated with the mAbs. After 1 h incubation at 37° C., 5% CO$_2$, followed by 15 minutes at room temperature, 12.5 of 5× dose of ligand was added to each well of the plate as a challenge agonist with detection of the calcium response on the FlexStation3 (Molecular Devices). The final concentration of ligand used in the assay was 9 nM of CXCL13 (#801-CX-025/CF, R&D). The IC$_{50}$ value of each mAb indicated Table 3 was calculated by Prism5. Each IC50 value represents Mean±S.D. (n=2) and one of two independent experiments which had similar results. R&D mAb (Cat# MAB 190, R&D) was used as a control anti-CXCR5 antibody. Antibody 11A7 is a fully human IgG1.

TABLE 3

IC50 [nM] of mAbs in calcium flux assay using CHO-CXCR5 cells

| | R&D mAb | 11A7 |
|---|---|---|
| CXCL13 | 10 | 5 |

Example 6

This example shows a chemotaxis assay with Sultan cells. Human B lymphocyte SH-Sultan cell line (CRL-1484, ATCC) was used for the chemotaxis assays. The chemotaxis assays were set up using 96-well chemotaxis chamber (ChemoTX; NeuroProbe, Gaithersburg, Md.) with the 2 compartments separated by a 5-µm polycarbonate membrane. Assay buffer used for chemotaxis was RPMI plus 0.5% FBS, 0.5 mM sodium pyruvate and 0.5% BSA. Serial diluted concentrations of mAbs were pre-incubated with the activated T cells (0.1×10$^6$ cells in 25 µl of the assay buffer) at room temperature for 20 min. Ligand (CXCL13) at 25 nM was loaded in the wells of plate in the lower chambers, whereas the pre-incubated cells with mAbs were loaded on top of membrane. After 4 h incubation at 37° C., 5% CO$_2$, migrated cells in the lower chamber were transferred to an opaque white 96 well plate and incubated with CellTiter GLO (Cat#G7571, Promega) for 10 min at room temperature. Luminescent signals generated from the cells in each well were detected by a fluorescent plate reader (FlexStation3, Molecular Devices). The IC$_{50}$ value of each mAb indicated in Table 4 was calculated by Prism5. Each IC$_{50}$ value represents Mean±S.D. (n=3) and one of two independent experiments which had similar results. The SAR113244 antibody used as a control in the assay is a Sanofi antibody expressed as an IgG1.

TABLE 4

IC50 [nM] of mAbs in chemotaxis assay using HS-Sultan cells

| | SAR113244 | 11A7 | R&D mAb |
|---|---|---|---|
| CXCL13 | 4.7 | 4.8 | 4.1 |

Sequence Listing

| | Heavy chain variable domain region | Light chain variable domain region |
|---|---|---|
| 52A9 | EVQLVESGGGVVQPGRSLRLSCAASGFTFSSYGMH WVRQAPGKGLEWVAVISYDGSNKYYADSVKGRFTI SRDNSKNTLYLQMNSLRAEDTAVYYCAKVPFYSSSS DYWGQGTLVTVSS SEQ ID NO. 1 | QSVVTQPASVSGSPGQSITISCTGTSSDVGG SKYVSWFQQHPGKAPKLMIYDVSNRPSGV SYRFSGSKSGNTASLTISGLQAEDEADYYCTS YTSSRTWVFGGGTKLTVL SEQ ID NO. 2 |
| 52A10 | QVQLVQSGAEVKKPGASVKVSCKASGYTFTSYGISW VRQAPGQGLEWVGWISAYNGNTNYAQKLQGRVT MTTDTSTSTAYMELRSLRSDDTAVYYCARGSDYWG QGTLVTVSS SEQ ID NO. 3 | SYELTQPPSASGTPGQRVTISCSGSSSNIGSN YVVWYQQLPGTAPKLLIYRNNQRPSGVPDR FSGSKSGTSASLAISGLRSEDEADYYCAAWD DSLSGPVFGGGTQLTVL SEQ ID NO. 4 |
| 52B10 | EVQLLESGGGLVQPGGSLRLSCAGSESTFGDSWLN WVRQAPGKGLEWVANINKDGSKKEYVESVKGRFTI SRDNAKKSVYLQMNSLRVEDTAVYYCLLKGVWGQ GTLVTVSS SEQ ID NO. 5 | AIQLTQSPSFLSASVGDRVTITCRASQGISSY LAWYQQKPGKAPKLLIYAASTLQSGVPSRFS GSGSGTEFTLTISSLQPEDFATYYCQQLNSYP ITFGPGTKVDIK SEQ ID NO. 6 |
| 52C6 | QVQLVESGGGLVQPGGSLRLSCAASGFTFDDYAMH WVRQAPGKGLQWVAVISHDGSAKYYADSVKGRFTI SRDNAKNSLYLQMNSLRAEDTAVYYCARSRWGDN WGQGTLVTVSS SEQ ID NO. 7 | SYELMQPASVSGSPGQSITISCTGTSSDVGG YNYVSWYQQHPGKAPKLMIYDVSKRPSGV SNRFSGSKSGNTASLTISGLQAEDEADYYCS SYTSSSTPYVFGTGTKLTVL SEQ ID NO. 8 |
| 52D6 | EVQLLESGGGLVQPGRSLRLSCAASGFNFDAYAMH WVRQAPGKGLEWVSGISWNSGYIAYADSVEGRFAI SRDNSKNTVFLQMNSLRAEDTAIYYCARDRWLSYW GQGTLVTVSS SEQ ID NO. 9 | QSVLTQPASVSGSPGQSITISCTGTSSDVGG YNYVSWYQQHPGKAPKLMIYDVSKRPSGV SNRFSGSKSGNTASLTVSGLQAEDEAEYYCS SYAGSNFVVFGGGTKLTVL SEQ ID NO. 10 |
| 52D7 | QVQLVQSGAEVKKPGASVKISCKASGYTITTHYIHW VRQAPGQGLEWMGIINPNSGRTKYPQKFQGRVTM TRDTSTNTVYMEVNSLRSEDTAVYYCATGSGSYGN WFDPWGQGTLVTVSS SEQ ID NO. 11 | QTVVTQPPSVSGAPGQRVTVSCTGSSSNIG SVVTQPPSVSAAPGQKVTISCSGSSSNIGNN YVSWYQQLPGTAPKLLIYDNNKRPSGIPDRF SGSKSGTSATLGITGLQTGDEADYYCGTWD SSLTLYVFGTGTKLTVL SEQ ID NO. 12 |
| 52D11 | QVQLVQSGGEVKKPGALVKVSCKASGYTFSTHGIS WVRQAPGQGLAWMGWISAYNGKATYAQTFQGR VTMTTDTSTNTAYMELRNLRSDDTAVYYCARVGAV TGMDSWGQGTLVTVSSS SEQ ID NO. 13 | QSVVTQPPSVSAAPGQTVTISCSGSSSNIGS KFVSWYQHVPGTAPKLLIYDNDKRPSGIPD RFSGSKSGTSATLGITGLQTGDEADYYCGT WDSSLSAYVFGTGTKVTVL SEQ ID NO. 14 |
| 52E1 | EVQLLESGAEVKKPGASVKVSCKASGYTFSRYAMH WVRQAPGQRLEWMGWIHAGNGNTKYSQKFQGR VTISRDTSASTAYMELSSLRSEDTAVYYCARGSIAAA GGFDYWGQGTLVTVSS SEQ ID NO. 15 | QAVLTQPPSASGTPGQRVTLSCSGSSSNIGR NYVYWYQQLPGTAPKLVLYVNDKRPSGIPD RFSGSKSGTSATLGITGLQTGDEADYYCGT WDSSLRAYVFGTGTKVTVL SEQ ID NO. 16 |
| 52E10 | QVQLVESGGGVVQPGRSLRLSCAASGFTFSSYGMH WVRQAPGKGLEWVAVISYDGSNKYYADSVKGRFTI SRDNSKNTLYLQMNSLRAEDTAVYYCAKGANFDY WGQGTLVTVSS SEQ ID NO. 17 | QAGLTQPPSASGSPGQSVTISCTGTSSDVG GYNYVSWYQQHPGKAPKLMIYEVSKRPSG VPDRFSGSKSGNTASLTVSGLQAEDEADYY CSSYAGSNKGVVFGGGTKLTVL SEQ ID NO. 18 |
| 52H9 | QVQLVESGGGVVQPGRSLRLSCAASGFTFSSYGMH WVRQAPGKGLEWVAVISYDGSNKYYADSVKGRFTI SRDNSKNTLYLQMNSLRAEDTAVYYCAKLSGPTAKF DYWGQGTLVTVSS SEQ ID NO. 19 | QSVLTQPASVSGSPGQSVTISCTGTSRDVG GYNFVSWYQQHPGKAPKLMIYDVSNRPSG VSNRFTGSKSGNTASLTISGLQAEDEADYHC SSYRRGDTLVFGGGTKLTVL SEQ ID NO. 20 |
| PC12 | EVQLLESGAEVKKPGASVKVSCKASGYTFTSYYVHW VRQAPGQGLEWMGIINPSGGTTSYAQKFQGRVTM TRDTSTSTVYMELSSLRSEDTAVYYCVRDRRVVAAT TPSAFDVWGQGTMVTVSS SEQ ID NO. 21 | QSVVTQPPSVSAAPGQKVTISCSGSSSNIGN NYVSWYQQLPGTAPKLLIYDNNKRPSGIPD RFSGSKSGTSATLGIVGLQTGDEADYYCAT WDGSLSTFLFGPGTKLTVL SEQ ID NO. 22 |
| PD10 | QMQLVQSGSEVKKPGASVKVSCRASGYLFTNYGIS WVRQAPGQGLEWMGWVSAHGEFTKYAPSLQDR VTMTSDISTTTAYMELRSLRSDDTGVYYCARDRGAD HFDTWGQGTLVTVSS SEQ ID NO. 23 | DIVMTQTPLSSPVTLGQPASISCRSSQSLVH SDGNTYLSWLQQRPGQPPRLLIYKISNRFSG VPDRFSGSGAGTDFTLKISRVEAEDVGVYYC TQATQFPFTFGQGTKLEIK SEQ ID NO. 24 |
| D3-4 | QVQLQQSGPGLLNPSQTLSLTCVISGDSVSSNSATW NWIRQSPSRGLEWLGRTYYRSQWFNDYAVSVKSRI TINPDTSKNQFSLQLSSVTPEDTAVYYCARWLHVW GQGTTVTVSS SEQ ID NO. 25 | LPVLTQPPSASGTPGQRVTISCSGGTSNIGN NNVYWYQQVPGMAPKLLIFRNSQRPSGVP DRFSGSKSGNTASLTISGLQAEDEGDYYCGS YAGPRTYVFGSGTKVTVL SEQ ID NO. 26 |
| E2-1 | EVQLLESGGGLVQPGGSLRLSCAASGFTFSSYGMH WVRQAPGKGLEWVAVISYDGSNKYYADSVKGRFTI SRDNSKNTLYLQLNSLRAEDTAVYYCARGQNLDYW GQGTLVTVSS SEQ ID NO. 27 | QPVLTQPASVSGSPGQSITISCTGTSSDVGG YNYISWYQQHPGKAPKLMIYEVSNRPSGVS NRFSGSKSGNTASLTISGLQAEDEADYYCSS YRSSTQVFGGGTKLTVL SEQ ID NO. 28 |
| A4 and 7A7 | QMQLVQSGAVVKPPGSSVKVSCKASGGTISRYVIS WVRQAPGQRLEWMGWINAANGRTKYLDKFQGR VTFTRDMSTSTASMELSSLTSEDTAVYFCARSLREQ VGGNYYYLMDVWGRGTTVTVSS SEQ ID NO. 29 | DIQLTQSPSSLSASVGDRVTITCRASQGIGTY LAWFQQKPGKVPKPLIYAASTLQSGVPSRFS GSGSGADFTLTISSLQPEDVATYYCQKYNSV PQTFGQGTKVEIK SEQ ID NO. 30 |

-continued

Sequence Listing

| | Heavy chain variable domain region | Light chain variable domain region |
|---|---|---|
| A8 | QVQLVESGGGVVQPGRSLRLSCAASGFTFSSYAMH WVRQAPGKGLEWVGRIKSKTDGGTTDYAAPVKGR FTISRDDSKNTLYLQMNSLKTEDTAVYYCTTGRHSG SYLRGTLVTVSS SEQ ID NO. 31 | NFMLTQPPSVSKGLRQTATLTCTGNSNNV QSALTQPRSVSGSPGQSVTISCTGTSSDVGT YNYVSWYQQHPGKAPKLIIYDVSIRPSGVSN RFSGSKSGNTASLTITGLQAEDEADYYCQSY DSSLSGVFGGGTQLTVL SEQ ID NO. 32 |
| A12 | QVQLVQSGAEVKKPGASVKVSCKASGNTLSNYAIH WVRQAPGQGLEWMGWINAVNGNTKYSQKFQGR VTATRDTSATIFYLELSSLRSEDTAVYYCVLITGAYWG EGTTVTVSS SEQ ID NO. 33 | LPVLTQPPSASGTPGQRVTISCSGNVSNIAN NYVYWYRHLPGTAPKLLMYRNNKRPSGVP DRFTASKSGTSASLAISGLRSEDEADYYCAA WDDSLHGYVFGTGTKVTVL SEQ ID NO. 34 |
| B3 | QVQLVESGGGLVKPGGSLRLSCAASGFTFSDYYMV WVRRSPGKGLEWISYISSSGGTIIYADSVKGRFTISRH NSENTLYLQMNSLRAEDTAVYYCATRSKGHALDVW GQGTTVTVSS SEQ ID NO. 35 | LPVLTQSPSASGTPGQRVTISCSGSSSNIGSN YVVWYQQLPGTAPKLLIYRNNQRPSGVPDR FSGSKSGTSASLAISGLQPEDEAYYYCASWD DRLTGYVFGSGTKVTVL SEQ ID NO. 36 |
| C8 | QVQLVESGGGVVQPGRSLRLSCAASGFTFSSYAMH WVRQAPGKGLEWVAVISYDGSNKYYADSVKGRFTI SRDNSKNTLYLQMNSLRAEDTAVYYCARRRAVAGH YYGMDVWGQGTTVTVSS SEQ ID NO. 37 | QAVLTQPPSVSKGLRQTATLTCTGNSNNVG NQGAVWLQQHQGHPPKFLSSRKNNRPSGI SERFSASRSGNTASLTITGLQPDDEADYYCS AWDSSLSSWVFGGGTKLTVL SEQ ID NO. 38 |
| F8 and 10G9 | EVQLVESGGGLVQPGGSLRLSCSGSGFSFSNYAMH WVRQAPGKGLEHVSAISSNGGSIYYADSVKGRFTIS RDNSKNMLYFQMSSLRTEDTAVYYCVKRVPGTSNF DYWGQGTLVTVSS SEQ ID NO. 39 | QPVLTQPPSASGTPGQRVTISCSGSSSNIGS NYVYWYQQLPGTAPKLLIYRNNQRPSGVPD RFSGSKSGTSASLAISGLRSEDEADYYCAAW DDSLSGRVFGGGTKLTVL SEQ ID NO. 40 |
| G11 | QVQLVESGGGLVQSGGSLRLSCAASGFTFSSYGMQ WVRQAPGKGLEWSSISSSGGSTFYADSVKGRFTIS RDNSKKTLYLQMSNLRAEDAAVYFCVKGGVLMPAA YFWGQGTLVTVSS SEQ ID NO. 41 | QSVLTQPPSASGTPGQRVTISCSGSSSNIGSF YVVWYQHPGTAPKLLIYRNNRRPSGVPDR FSGSKSGNTASLTISGLQAEDEADYYCSSYPR NTVLFGGGTKLTVL SEQ ID NO. 42 |
| H3 | QVQLVESGAEVKKPGASVKVSCKASGWTRNYMH WVRQAPGQGLEWMGWINPKNGGTNYAQKFQDR VTMTRDSSISTAYMELSSLRSEDTAVYYCATGIRSTV RGLDNWGQGTLVTVSS SEQ ID NO. 43 | QSALTQPASVSGSPGQSITISCSGSNRDVGG YYFVSWYQKHPGKAPRLMIYDVINRPSGVP DRFSGSKSGNTASLTISGLQPEDEGEYYCSSF TSSRTLAFGGGTKLTVL SEQ ID NO. 44 |
| H5 | QVQLVESGAEVKKPGASVKVSCKASGYTLTSYYMH WVRQAPGQGLEWMGIINPSGGNTSYAQKFQGRV TMTRDTSTSTVYMELSSLRPDDTAVYYCATDGELEI AAYWGQGTLVTVSS SEQ ID NO. 45 | LPVLTQPPSVSGAPGQRVTISCTGSSSNIGA AYDVHWYQQLPGTAPKLLIYSNNERPSGVP DRFSGSKSGTSASLAISGLQSEDEADYYCAA WDDSLNGYVFGTGTKLTVL SEQ ID NO. 46 |
| H6 | EVQLLESGGGVVQPGRSLRLSCAASGFTFSSYAMH WVRQAPGKGLEWVAVISYDGSNKYYADSVKGRFTI SRDNSKNTLYLQMNSLRAEDTAVYYCAKHRRGDHG DYWGQGTLVTVSS SEQ ID NO. 47 | QAGLTQPASVSGSPGQSITISCTGTSTDIGVY DHVSWYQQHPGKAPRLILSGVYKRPSAVSD RFFGSKSGSTASLTISGLQPDDEAEYRCMSY TTSKTYVFGTGTKLTVL SEQ ID NO. 48 |
| 2D3 | QVQLQQSGPGLLNPSQTLSLTCVISGDSVSSNSATW NWIRQSPSRGLEWLGRTYYRSQWFNDYAVSVKSRI TINPDTSKNQFSLQLSSVTPEDTAVYYCARWLHVW GQGTTVTVSS SEQ ID NO. 25 | QAGLTQPSSLSASPGASASLTCTLRSGINVG TYRIYWYQQKPGSPPQYLLMYKSDSDKQQ GSGVPSRFSGSKDASANAGILLISGLQSEDE ADYYCMIWHSSAYVFGTGTKVTVL SEQ ID NO. 49 |
| 3A11 | QVQLVQSGGGVVQPGRSLRLSCAASGFTFSSYGMH WVRQAPGKGLEWVAVISYDGSNKYYADSVKGRFTI SRDNSKNTLYLQMNSLRAEDTAVYYCAHGGDYYW GQGTPVTVSS SEQ ID NO. 50 | QSALTQPPSVSAAPGQKVTISCSGSSSNIGN NYVSWYQQLPGTAPKLLIYDNNKRPSGIPD RFSGSKSGTSATLGITGLQTGDGADYYCGT WDDSLSAGVFGGGTKLTVL SEQ ID NO. 51 |
| 3B9 | EVQLVESGGGLVKPGESLRLSCAASGFTFKSYPMA WVRQAPGKGLEWSSISSSGDHRYYADSVKGRFTIS RDNARNSLSLQMNNLRAEDTAVYYCPAGRDFDHW GRGTLVTVSS SEQ ID NO. 52 | QAGLTQPASVSGSPGQSITISCTGTSSDVGG YNYVSWYQQHPGKAPKLIINEVFNRPSGSS NRFSGSKSGNTASLTISGLQAEDEADYYCSS PTTSKTLVFGGGTKVTVL SEQ ID NO. 53 |
| 3D11 | EVQLVQSGGGLVQPGGSLRLSCSASGFTFSSYAMH WVRQAPGKGLEYVSAISSNGGSTYYADSVKGRFTIS RDNSKNTLYLQMSSLRAEDTAVYYCVKRTGRDGY NDWGQGTLVTVSS SEQ ID NO. 54 | DIVMTQSPPSLSASVGDSVAITCRASQDIRN DLGWFQQKPGTAPKRLIFAASGLQSGVPSR FRGSGSGTEFTLTINNLQPEDSATYYCLQHY RFPRVFGQGTKVEIK SEQ ID NO. 55 |

Sequence Listing

| | Heavy chain variable domain region | Light chain variable domain region |
|---|---|---|
| 3D12 and 4E12 | EVQLVESGGGLVQPGGSPRLSCAASGFTFSSYAMS WVRQAPGKGLEWVSVISGSGGTTYYADSVKGRFTI SRDNSKNTLYLMNSLRAEDTALYYCAKAVRGVSPF DYWGQGTLVTVSS SEQ ID NO. 56 | QSVVTQPPSVSGAPGQRVTVSCTGSSSNIG SRYAVNWYQQLPGRAPKLLIYGNTNRPSGV PDRFSASKSGTSASLAISGLQAEDEADYYCQ SFDSSLRGYVFGTGTKVTVL SEQ ID NO. 57 |
| 3E7 | QVQLQQSGPGLVRPSQTVSLTCVISGDSVSSNRVG WNWLRQSPSRGLEWLGGTAYRSTWRLYYPPSLKSR VTITPDTSRNQFSLLLNSVTPDDTAVYYCARGFVEAF DVWGQGTMVTVSS SEQ ID NO. 58 | QAGLTQPASVSGSPGQSITISCTGTSSDVGG YNYVSWYQQHPGKAPKLMIYDVSKRPSGV SHRFSGSKSGNTASLTISGLQAEDEADYYCS SYRSRSTLVFGGGTQLTVL SEQ ID NO. 59 |
| 3E12 | QVQLQQSGPGLVKPSQTLSLTCAISGDSVSSNSAA WNWIRQSPSRGLEWLGRTYYRSKWFYDYAVSVKS RITINPDTSKNQFSLQLSSVTPEDTAVYYCARWLHV WGQGTTVTVSS SEQ ID NO. 60 | QSVLTQPPSASGTPGQRVTIPCSGSSSNIGS KTVSWYQQLPGTAPKLLIYSSDQRPSGVPD RFSASKSGTSASLAISGLQSEDEADYYCAAW DGSLDGYVFGTGTKVTVL SEQ ID NO. 61 |
| 3F7 | QVQLVESGGGVVQPGRSLRLSCAASGFTFSDYGMH WVRQAPGKGLEWVAVISYDGSNKYYADSVKGRFTI SRDNSKNTLYLMNSLRAEDTAVYYCARIQARSGSS LGQGTLVTVSS SEQ ID NO. 62 | QAVLTQPPSVSQALRQTATLTCTGNSNNVG SQGAAWLQQHQGHPPKLLSYRNNNRPSGI SERFSASRSGDTASLTISGLQPEDEADYFCSA WDNSLRAWVFGGGTKLTVL SEQ ID NO. 63 |
| 3G2 | QMQLVQSGAEVKKPGASVKVSCKASGYTFTSYAM HWVRQAPGQRLEWMGWINAGNGNTKYSQKFQG RVTITADKSTSTAYMELSSLRSEDTAVYYCARGRVVR NQNYYYYGMDVWGQGTTVTVSS SEQ ID NO. 64 | DIQLTQSPLSLPVTLGQPASISCMSSQSLVHS DGNTYLNWFQQRPGQSPRRLIYKVSNRDS GVPDRFSGSGSGTDFTLKISRVEAEDVGVYY CMQGSHWPRTFGQGTRLEIK SEQ ID NO. 65 |
| 3G7 | EVQLVESGGGVVQPGRSLRLSCAASGFTFSSYAMH WVRQAPGKGLEWVAVISYDGSNKYYADSVKGRFTI SRDNSKNTLYLMNSLRAEDTAVYYCARGALAGYW GQGTLVTVSS SEQ ID NO. 66 | DVVMTQSPLSLPVTLGQPASISCRSSQSLVH SDGNTYLNWFQQRPGQSPRRLIYKVSNRDS GVPDRFSGSGSGTDFTLKISRVEAEDVGVYY CMQGTHWPPWTFGGGTKLEIK SEQ ID NO. 67 |
| 4A5 | EVQLVESGGGLIQPGGSLTLSCAASGVIVSSYYMSW VRQAPGKGLEWVSVVSPSGRTYYKDSVKGRFTISRD TSKNTVSLQMNNLRGEDAAIYYCTRTSGLYGTDVW GQGTTVTVSS SEQ ID NO. 68 | AIRMTQSPSSVSASVGDRVTITCRASQSISS WLAWYQQKPGKAPKLLIYKASSLQSGVPSR FSGSGSGTEFSLTISSLQPDDFATYYCQQYNS YTYTFGQGTKLEIK SEQ ID NO. 69 |
| 4E9 | QVQLVESGGGVVQPGRSLRLSCAASGLDFSNYAMH WVRQAPGKGLEWVAVISYDGTKKYYADSVKGRFTI SRDNSKNTLYLQMNSLETEDTAVYYCTRGFRIFGYW GQGTLVTVSS SEQ ID NO. 70 | DIVMTQSPLSSPVTLGQPASISCRSSQSLVHS NGNTYLSWLQQRPGQPPRLLLYRISNRFSG VPDRFSGSGAGTNFTLKISRVEAEDVGVYYC MQATQFPRTFGQGTKVDIK SEQ ID NO. 71 |
| 4F1 | EVQLVQSGAEVKKPGASVKVSCKASGYTFSDYYMH WVRQAPGEGLEWMGWINPNSGDTNYPQKFQGR VTMTRDTSISTAYMELSSLRSDDTAVYYCAREMAKL GIRNLDYWGQGTLVTVSS SEQ ID NO. 72 | QSALTQPPSASGTPGQRVTISCSGSSSNIGS YRVNWYQQLSGAAPKLLIYRNNQRPSGVS NRFSGSKSGNTASLTISGLQAEDEADYYCSS YTSSSAVVFGGGTKLTVL SEQ ID NO. 73 |
| 4F4 | QVQLQQSGPGLVKPSQTLSLTCVISGDSVSNNRAA WNWIRQSPSGGLEWLGRTYYRSKWYSDYGASVKS RITVNPDTSKNQFSLQVNSVTPDDTAVYYCARGKVS AFDIWGQGTMVTVSS SEQ ID NO. 74 | QSVLTQPPSASGTPGQRVTISCSGGSSNIGR HAVNWYQQLPGTAPKLLIYRSNQRPSGVS NRFSGSKSGNTASLTISGLQAEDEADYYCSS YTSSSTPYVFGTGTKLTVL SEQ ID NO. 75 |
| 4H2 | EVQLVQSGGGLVKPGGSLRLSCAASGFTFSDYYMS WIRQAPGKGLEWVSYISSSGSTIYYADSVKGRFTISR DNAKNSLYLQMNSLTVEDTAVYYCARGGYPRGWG QGTLVTVSS SEQ ID NO. 76 | DIVMTQSPLSLPVTLGQPASISCRSSQSLVHS NGITYLNWFQQRPGQSPRRLIYKVSNRDSG VPDRFSGSGSGTDFTLKISRLEAEDVGVYYC MQGTHWPPTFGQGTKVEIK SEQ ID NO. 77 |
| 5A8 | QVQLVQSGAEVKKPGASVKVSCKASGYTFTNYGIS WVRQAPGQGLEWMGWISAYNGNTNYAQKFQGR VTMTDTSTSTAYMELSSLKSEDTAVYYCATLGGAT WGQGTTVTVSS SEQ ID NO. 78 | LPVLTQPASVSGSPGQSITISCTGTSSDVGGY NYVSWYQQHPGKAPKLMIYDVSKRPSGVS NRFSGSKSGNTASLTISGLQAEDEADYYCSS YTSSSTVVFGGGTKLTVL SEQ ID NO. 79 |
| 5F1 | QVQLQQSGPGLVKPSQTLSLTCVISGDSVSSNSAA WNWIRQSPSGALEWLGRTYYRSKWYNDYAPSVKS RITINPDTSKNQFSLQLNSVTPEDTAVYYCAKWLSV WGQGTTVTVSS SEQ ID NO. 80 | QAGLTQPPSASGTPGQRVTIPCSGSSSNIGS KTVSWYQQLPGTAPKLLIYSSDQRPSGVPD RFSASKSGTSASLAISGLQSEDEADYYCAAW DGSLDGYVFGTGTKLTVL SEQ ID NO. 81 |

Sequence Listing

| | Heavy chain variable domain region | Light chain variable domain region |
|---|---|---|
| 6A4 | QVQLVQSGSVLKKPGASVKVSCETSGYSFTSYGLHW LRQAPGQGLQWMGWIHPNTGNPSYAPGFTGRYV FSRDTSVSTTYLQINSLEDGDTAIYFCARARYGLDVW GQGTTVTVSS SEQ ID NO. 82 | QTVVTQPPSVSAAPGQKVTISCSGSSSNIGS HFVSWYQQLPGTAPKLLIYDNKKRPSGIPDR FSGSKSGTSATLGITGLQTGDEADYYCGTW DSSLSAGVFGGGTKVTVL SEQ ID NO. 83 |
| 6F9 | EVQLVESGGGLVQPGGSLRLSCAASGFTFSDYYMS WIRQAPGKGLEWVSYISSSGSTMYYADSVKGRFTIS RDNAKNSLFLQMNSLRDDDTAVYYCARGGYPRYW GQGTTVTVSS SEQ ID NO. 84 | QPVLTQPPSVSKGLRQTATLTCTGNSSNVG NLGAAWLQQHQGRPPKLLSYRNNNRPSGI SERLSASRSGNTASLTITGLQPEDEADYYCA AWDTSLRVWVFGGGTKLTVL SEQ ID NO. 85 |
| 6G5 | EVQLLESGAEVKKPGASVKVSCKASGYTFSRYAMH WVRQAPGQRLEWMGWIHAGNGNTKYSQKFQGR VTISRDTSASTAYMELSSLRSEDTAVYYCARGSIAAA GGFDYWGQGTLVTVSS SEQ ID NO. 15 | SYVLTQPPSASGTPGQRVTLSCSGSSSNIGR NYVYWYQQLPGTAPKLVLYVNDKRPSGIPD RFSGSKSGTSATLGITGLQTGDEADYYCGT WDSSLRAYVFGTGTQLTVL SEQ ID NO. 86 |
| 7B11 and 8B2 | QVTLRESGGGLVQPGGSLRLSCAASGFTFSPYWMS WVRQAPGKGLEWVASIKKDASGEYYVDSVKGRFSI SRDNAKNSVYLQMNSLRAEDTAVYYCARGGWVLD VWGQGTTVTVSS SEQ ID NO. 87 | ETTLTQSPGTLSLSPGERATLSCRASQSVRSS YLAWYQQKPGQAPRLLIYGASSRATGIPDRF SGSGSGTDFTLTISRLEPEDFAVYYCQQYGSS PLTFGQGTKVEIK SEQ ID NO. 88 |
| 7H10 | EVQLVESGGGLIQPGGSLRLSCSASGFTLNNYYMN WVRQAPGKGLEWVSVIYSGGNTFYADSVKGRFIISR DSSKNILYLQMNSLRAEDTAVYYCARKYCSGGYCKY DYWGQGTLVTVSS SEQ ID NO. 89 | QPVLTQPPSASGTPGQRVTISCSGSSSNIGS NFVYWYQQFPGMAPKLLIYRNNQRPSGVP DRFSGSKSGTSASLVISGLRSEDEATYYCAS WETSLSGPRVFGGGTKL SEQ ID NO. 90 |
| 8D12 | EVQLLESGAEVKKPGASVKVSCKASGYTFSRYAMH WVRQAPGQRLEWMGWIHAGNGNTKYSQKFQGR VTISRDTSASTAYMELSSLRSEDTAVYYCARGSIAAA GGFDYWGQGTLVTVSS SEQ ID NO. 15 | LLVLTQSPSASGTPGQRVTLSCSGSSSNIGR NYVYWYQQLPGTAPKLVLYVNDKRPSGIPD RFSGSKSGTSATLGITGLQTGDEADYYCGT WDSSLRAYVFGTGTKVTVL SEQ ID NO. 91 |
| 8H5 | QVQLVESGGGLVQPGGSLRLSCAASGFTFSDYYMS WIRQAPGKGLEWVSYISSSGSTMYYADSVKGRFTIS RDNAKNSLFLQMNSLRDDDTAVYYCARGGYPRYW GQGTTVTVSS SEQ ID NO. 92 | QSVLTQPPSVSKGLRQTATLTCTGNSSNVG NLGAAWLQQHQGRPPKLLSYRNNNRPSGI SERLSASRSGNTASLTITGLQPEDEADYYCA AWDTSLRVWVFGGGTQLTVL SEQ ID NO. 93 |
| 9A10 | EVQLVQSGGGLVKPGGSLRLSCAASGFTFSDYYMS WIRQAPGKGLEWVSYISSSGSTIYYADSVKGRFTISR DNAKNSLYLQMNSLRAEDTAVYYCASGLSGVGATN VHYWGQGTLVTVSS SEQ ID NO. 94 | LPVLTQPPSVSKGLRQTATLTCTGNTNNVG NQGAAWLQQHQGHPPKLLSYRNNNRPSG ISERLSASRSGNTASLTITGLQPEDEADYYCS AWDSSLNVWVFGGGTKLTVL SEQ ID NO. 95 |
| 10A12 | EVQLVQSGAEVKKPGASVKVSCKASGYTFTSYAMH WVRRAPGQRLEWMGWINAGNGNTKYSQKFQGR VTITRDTSASTAYMELSSLRSEDTAVYYCARDGIVATI WGQGTLVTVSS SEQ ID NO. 96 | QPVLTQPASVSGSPGQSITISCTGTRSDVGT YNLVSWYQRHPGRAPKLMIYEVSKRPSGIS NLFSGSKSGNTASLTISGLQSEDEADYYCCSY TGRLTLVFGGGTKLTVL SEQ ID NO. 97 |
| 10B2 | QVQLVQSGAEVKKPGASVKVSCKASGYTFTSYGISW VRQAPGQGLEWMGWISAYNGNTNYAQKLQGRVT MTTDTSTSTAYMELRSLRSDDTAVYYCARARAVAG RGSYWGQGTLVTVSS SEQ ID NO. 98 | QPVLTQPRSVSGSPGQSVTISCTGTSSDVGS YNLVSWYQRHPGKAPKLVIYEVNKRPSGVS NRFSGSKSGNTASLTISGLQAEDEADYYCSS YTSSSTYVFGTGTKLTVL SEQ ID NO. 99 |
| 10C3 | QVQLVESGGGVVQPGRSLRLSCAASGFTFSNYAMH WVRLAPGKGLEWVAVISYDGSNKYYGDSVKGRFTI SRDNSKNTLYLQMNSLRAEDTAVYYCARRNNLDY WGQGTLVTVSS SEQ ID NO. 100 | QPVLTQPPSASGSPGQSVTISCTGTSSDIGR YNYVSWYQQYPGKAPKLIIYEVNKRPSGVP DRFSGSKSGNTASLTVSGLQAEDEADYYCSS YTSSRTLVFGGGTKLTVL SEQ ID NO. 101 |
| 10C7 | QVQLVQSGGGLVQPGGSLRLSCAASGFTFSSYSMN WVRQAPGKGLEWVSYISSSSTIYYADSVKGRFTISR DNSKNTLYLQMNSLRAEDTAIYYCARKGLAAPGKGY WGQGTLVTVSS SEQ ID NO. 102 | LPVLTQPRSVSGSPGQSVTISCTGTSSDVGR YGYVSWYQQHPGKAPQLMIYEVNKRPSGV PDRFSGSKSDNTASLTISGLQAEDEADYYCS SYTSSSTRVFGTGTKVTVL SEQ ID NO. 103 |
| 11E3 | EVQLVESGGGVVQPGRSLRLSCAASGFTFSSYAMH WVRQAPGKGLEWVAVISYDGSNKYYADSVKGRFTI SRDNSKNTLYLQMNSLRAEDTAVYYCARLPIPKQST VAGTSYWGQGTLVTVSS SEQ ID NO. 104 | LPVLTQPASVSGSPGQSITISCTGTSSDVGGY NYVSWYQQHPGNAPKLMIYDVSNRPSGVS NRFSGSKSGNTASLTISGLQAEDEADYYCSS YTSSSTLYVFGTGTKLTVL SEQ ID NO. 105 |
| 11A12 | EVQLVESGGGVVQPGGSLRLSCETSGFVFSDYAMH WVRQAPGKGLDWVAVMSSDGSNKYYGNSVKGRF TISRDNSKNTLYLQMNSLRGEDTAVYFCARTNTRLF FGGKLRGDFWGQGTLVTVSS SEQ ID NO. 106 | QSVLTQPPSVSKGLRQTATLTCTGNSNNVG NQGAAWLQQHQGHPPKLLFYRNNNRPSG ISERFSASRSGNTASLTITGLQPEDEADYYCS AWDSSLSARVFGGGTKLTVL SEQ ID NO. 107 |

Sequence Listing

| | Heavy chain variable domain region | Light chain variable domain region |
|---|---|---|
| 11A7 | EVQLVESGGGLVQPGGSLRLSCAASGFTVSSNYMS WVRQAPGKGLEWVSVIYSGGSTYYADSVKGRFTISR HNSKNTLYLQMNSLRAEDTAVYYCARGYVVWGQG TLVTVSS SEQ ID NO. 108 | QPVLTQPPSVSKDLRQTATLTCTGNSNNVG NQGAPTWLQQHQGHPPKLLSYKNNNRPSGI SERFSASRSGNTASLTITGLQPEDEADYYCSA WDSSLSAWVFGGGTQLTVL SEQ ID NO. 109 |
| 11C3 | QVQLVESGGGLVKPGGSLRLSCEASGFTFSSYAMH WVRQAPGKGLEWVAVISYDGSNKYYADSVKGRFTI SRDNTKNSLYLQLSSLRAEDTALYYCATGRTMALWG QGTTVTVSS SEQ ID NO. 110 | QAVLTQPASVSGSPGQSITISCTGTSSDVGG YNYVSWYQQHPGKAPKFMIYDVSKRPSGV SDRFSGSKSGNTASLTISGLQAEDEADYYCS SYTSSSTLVFGGGTKLTVL SEQ ID NO. 111 |
| 11D3 | QVQLVQSGGGVVQPGRSLRLSCAASGFTFSNFGM HWVRQAPGKGLEWVAVISYDGSNKYYADSVKGRF TISRDNSKNTLYLQMNSLRAEDTAVYYCARNTVTYH DVWGQGTTVTVSS SEQ ID NO. 112 | QPVLTQPASVSGSPGQSITISCTGTSSDVGG YNYVSWYQQHPGKAPKLMINDVSNRPSGV SSRFSGSKSGNTASLTISGLQAEDEADYYCSS YTSSSTLVFGGGTKLTVL SEQ ID NO. 113 |
| 11D4 | QITLKESGGGVVQPGRSLRLSCAASGFTFSSYGMH WVRQAPGKGLEWVAVISYDGSNKYYADSVKGRFTI SRDNSKNTLYLQMNSLRAEDTAVYYCANNGWATY PDYWGQGTLVTVSS SEQ ID NO. 114 | QSVLTQPASVSGSQGQSITISCTGTSSDVGA YNYVSWYQQYPGEAPRLILYDVSQRPSGIS NRFSGSKSGNMASLTISGLQAEDEADYYCSS YRSSSTVVFGGGTKVTVL SEQ ID NO. 115 |
| 11D7 | EVQLVQSGGGVVQPGRSLRLSCAASGFTFSSYGMH WVRQAPGKGLEWVAVISYDGSNKYYADSVKGRFTI SRDNSKNTLYLQMNSLRAEDTAVYYCAKLSGPTAKF DYWGQGTLVTVSS SEQ ID NO. 116 | QAGLTQPASVSGSPGQSITISCTGTSSDVGG YKYVSWYQQHPGKAPKLMIYDVSKRPSGVS NRFSGSKSGNTASLTISGLQAEDEADYYCSS YTSRSTLFVFGTGTKVTVL SEQ ID NO. 117 |
| 11F3 | QVQLVESGGGVVQPGRSLRLYCAASGFIFSSYAIHW VRQAPGKGLEWVAVISYDGSKKYYADSVEGRFTISR DNSKNSLYLQMNSLRVDDTAVYYCAAHRQLGYWG QGTLVTVSS SEQ ID NO. 118 | QSVLTQPPSASGSPGQSVTISCTGTSSDVGG YNYVSWYQQHPGKAPKLMIYDVSKRPSGVS SNRFSGSKSGNTASLTISGLQAEDEADYYCS SYTSSSTLVFGGGTKLTVL SEQ ID NO. 119 |
| 11G3 | EVQLVQSGGGVVQPGRSLRLSCAASGFTFSSYAMH WVRQAPGKGLEWVAVISYDGSNKYYADSVKGRFTI SRDNSKNTLYLQMNSLRAEDTAVYYCARLTRGSDYY GSGRSMNDYWGQGTLVTVSS SEQ ID NO. 120 | DIVMTQTPLSLPVTLGQPASISCRSSQSLVHS DGNTYLNWFQQRPGQSPRRLIYKVSNRDS GVPDRFSGSGSGTDFTLKISRVEAEDVGVYY CMQGTHWPPTFGQGTKVEIK SEQ ID NO. 121 |
| 12A4 | QVQLVESGGGLVQPGRSLRLSCTASGFTFGDYAVT WVRQAPGKGLEWVGFIRSMTYGGPTQYAASVKGR FTISRDDSKGIAYLQMNRLKTEDTAVYFCTVAGQH WGQGTLVTVSS SEQ ID NO. 122 | SYELTQPLSVSVALGQTARITCGGNNIGSKN VHWYQQKPGQAPVLVIYRDSNRPSGIPERF SGSNSGNTATLTISRAQAGDEADYYCQVW DSSTHNYVFGTGTKVTVL SEQ ID NO. 123 |
| 12B11 and 14E10 | EVQLVESGGGLVKPGRSLRLSCTASGFPEGDYAMS WFRQAPGKGLEWVALISYDGRNNYYADSVKGRFTI SRDNSKNTLYLQMNSLRAEDTAVFYCARDRMRGP GGRFYYYHAMDVWGQGTTVTVSS SEQ ID NO. 124 | SYELMQPPSVSRGLRQTATLTCAGTRNDVG NEGASWLQQHQGHPPKLLSYRDTNRPSGIS DRFSASRSGNTASLTISGLQPEDEADYYCSA WDSSLRAWVFGGGTKLTVL SEQ ID NO. 125 |
| 12B4 | QVTLRESGGGLVKPGGSLRLSCAASGFTFSDYYMT WIRQAPGKGLEWVSYISTGGTIYYADSVKGRFTISRD NAKNSLYLQMDSLRAEDTAVYYCAGGARDCGGGT CKRRGFHWGQGTLVTVSS SEQ ID NO. 126 | QPVLTQPRSVSGSPGQSVTISCTGTSSDVGS YDYVSWYQQHPGKAPKVMIYDVSKRPSGV SNRFSGSKSGNTASLTISGLQDEDEADYYCR SYTSSATYVFGTGTKVTVL SEQ ID NO. 127 |
| 12C1 | EVQLLESGGGLVKPGGSLRLSCAASGFTFNNYAMH WVRQAPGKGLEWLTV'SFYGGKQYYADSVKGRFTI SRDNSRNTLYLQMNSLRADDTAVYYCARDNGRHF DYWGQGTLVTVSS SEQ ID NO. 128 | QPVLTQPASVSGSPGQSITISCTGTSSDVGG YNYVSWYQQHPGKAPKLMIYDVSKRPSGV SNRFSGSKSGNTASLTISGLQAEDEADYYCT SYRSGRTYVFGSGTKVTVL SEQ ID NO. 129 |
| 12C6 | EVQLVQSGAEVKKPGASVKISCKASGYTITTHYIHW VRQAPGQGLEWMGIINPNSGRTKYPQKFQGRVTM TRDTSTNTVYMEVNSLRSEDTAVYYCATGSGSYGN WFDPWGQGTLVTVSS SEQ ID NO. 130 | QSVVTQPPSVSAAPGQKVTISCSGSSSNIGN NYVSWYQQLPGTAPKLLIYDNNKRPSGIPD RFSGSKSGTSATLGITGLQTGDEADYYCGT WDSSLTLYVFGTGTKLTVL SEQ ID NO. 131 |
| 12D11 | EVQLVQSGAEVKKPGASVKVSCKASGYTFTGYYLN WVRQAPGQGLEWMGWINPNNGGTNYAQRFQG RVTMTRDTSISTAYMDLSRLRSDDTAVYYCVRGTRK YYHDSNGRRRDYYYGMDVWGQGTTVTVSS SEQ ID NO. 132 | A1RMTQSPSSLSASVGDRVTITCRASQSISSY LNWYQQKPGKAPKLLIYAASSLQSGVPSKFS GSGSGTEFTLTISSLQPEDFATYYCQQYKFYP PNFGGGTKVEI SEQ ID NO. 133 |

| | Heavy chain variable domain region | Light chain variable domain region |
|---|---|---|
| 12D3 | EVQLVESGGGLVKPGRSLRLSCAASGFTFSSYAMH WVRQAPGKGLEWVAVISYDGSNKYYADSVKGRFTI SRDNSKNTLYLQMNSLRAEDTAVYYCARLRWLDY WGQGTLVTVSS SEQ ID NO. 134 | QPVLTQPASVSGSPGQSIAISCTGTSSDVGS NNRVSWYQQHPGKAPKLMIYEVDKRPSGV SNRFSGSKSGNTASLTISGLQAEDEADYYCG TWDSSLSAYVFGTGTKLTVL SEQ ID NO. 135 |
| 12G10 | EVQLVESGGGVVQPGRSLRLSCAASGFTFSSYAMH WVRQAPGKGLEWVAVISYDGSNKYYADSVKGRFTI SRDNSKNTLYLQMNSLRAEDTAVYYCARIAVAGTHF DYWGQGTLVTVSS SEQ ID NO. 136 | SYELMQPPSVSGTPGQRVTISCSGSTSNVGS NTVNWYRQPPGTAPKLLIYANNQRPSGVS DRFSGSKSGTSASLAISGLQSENEADYYCAA WDDSLNGYVFGTGTKLTVL SEQ ID NO. 137 |
| 13E10 | EVQLVQSGAEVKKPGASLKISCRASGYTFTRNYIHW VRQAPGQGLEWLGIINPNGGSTRYSQKFQGRVTM TRDTSTRTVYMELSSLRSEDTAVYYCAREAPKYCSGS SCYSGGVDYWGQGTLVTVSS SEQ ID NO. 138 | QPVLTQPLSASGTPGQRVTISCSGSSSNIGS NYVYWYQQLPGTAPKLLIYRNYQRPSGVPD RFSGSTSGTSASLAISGLRSEDEADYHCAAW DGSMRGWVFGGGTKLTVL SEQ ID NO. 139 |
| 13E4 | QITLKESGGGVVQPGRSLRLSCAASGFTFSSYGMH WVRQAPGKGLEWVAVISYDGSNKYYADSVKGRFTI SRDNSKNTLYLQMNSLRAEDTAVYYCANNGWATY PDYWGQGTLVTVSS SEQ ID NO. 114 | QPVLTQPASVSGSPGQSITISCTGTSSDVGG YNYVSWYQQHPGKAPKLMIYDVSNRPSGV SNRFSGSKSGNTASLTISGLQAEDEADYYCS SYTSSSTLVFGGGTKLTVL SEQ ID NO. 140 |
| 13A3 | EVQLVQSGGGVVQPGRSLRLSCVASGFTFRTYGMH WVRQAPGKGLEWVAVISHDGSNKYYADSVKGRFTI SRDNSKNTLYLQMSSLRAEDTAVYYCARATFGQGTL VTVSS SEQ ID NO. 141 | QAGLTQPASVSGSPGQSITISCTGTSSDVGS YNLVSWYQQHPGKAPKLMIYEGSKRPSGVS NRFSGSKSGNTASLTISGLQAEDEADYYCCS HAGSSTYVFGTGTKVTVL SEQ ID NO. 142 |
| 13F8 | EVQLLESGGGVVQPGRSLRLSCAASGFTFSSYAMH WVRQAPGKGLEWVAVISYDGSNKYYADSVKGRFTI SRDNSKNTLYLQMNSLRAEDTAVYYCARLTRGSDYY GSGRSMNDYWGQGTLVTVSS SEQ ID NO. 143 | DIVMTQSPLSLPVTLGQPASISCRSSQSLVHS DGNTYLNWFQQRPGQSPRRLIYKVSNRDS GVPDRFSGSGSGTDFTLKISRVEAEDVGVYY CMQGTHWPTFGQGTKLEIK SEQ ID NO. 144 |
| 13F9 | EVQLLESGGGLIQPGGSLRLSCAASGFIFSRYGMHW VRQAPGKGLEWVAVTSYDGRSKYYTDSVQGRFTIS RDNSKNTLDLQMNSLRAEDTAVYYCARLHTVGPW HFDLWGRGTLVTVSS SEQ ID NO. 145 | SYELTQPRSVSGSPGQSVTISCTGTSSDVGG YNYVSWYQQHPGKVPKLMIYEVSNRPSGV SNRFSGSKSGNAASLTISGLQAEDEADYYCS SYTSSSTLVFGGGTKLTVL SEQ ID NO. 146 |
| 13G9 | EVQLVESGGGVVQPGRSLRLSCAASGFTFSRYGMH WVRQSPGKGLEWVAGISYDGSDKYYADSVKGRFTI SRANSKNTLFLQMNSLRAEDTAVYYCARARGLDYW GQGTTVTVSS SEQ ID NO. 147 | QAVLTQPASVSGSPGQSITISCTGTSSDIGSY NLVSWYQQHPGKAPKLIIYEVNKRPSGVSN RFSGSKSGNTASLTISGLQAEDEADYYCSSYR SINTVVFGGGTQLTVL SEQ ID NO. 148 |
| 14E5 | EVQLVESGGGVVQPGRSLRLSCAASGFTFSSYGMH WVRQAPGKGLEWVAVISYDGSNKYYADSVKGRFTI SRDNSKNTLYLQMNSLRAEDTAVYYCAKVYSRGSDY WGQGTLVTVSS SEQ ID NO. 149 | QSVLTQPASVSGSPGQSITISCTGTSSDVGG YNYVSWYQQHPGKAPKLLIYDVSRRPSGIS RFSGSKSGNTASLTISGLQTEDDGDYYCLSYT TSRAVVFGGGTKLTVL SEQ ID NO. 150 |
| 14B11 | QVQLVESGGGVVQPGMSLRLSCAASGFTFSSHAM HWVRQAPGKGLEWVAQIWSDGSNRYYSDSVKGR FTISRDQSKNTVSLQMNSLRAEDTAVYFCARDGQS MAPYAMDVWGQGTMVTVSS SEQ ID NO. 151 | DIVMTQTPLSLPVTPGEPASISCRSSQSLLHK NGNNYLDWYLQRPGQSPQLLIYLASNRASG VPDRFSGSGSGTDFTLEISRVQPEDVGVYYC MQGLQTPTFGPGTKVEIK SEQ ID NO. 152 |
| 14B4 | QVQLQQSGPGLLNPSQTLSLTCVISGDSVSSNSATW NWIRQSPSRGLEWLGRTYYRSQWFNDYAVSVKSRI TINPDTSKNQFSLQLSSVTPEDTAVYYCARWLHVW GQGTTVTVSS SEQ ID NO. 25 | QSVVTQPPSVSAAPGQKVTISCSGSSSNIGS KAVNWYQQLPGTAPKLLIYGNNQRPSGVP DRFSGSKSGTSASLAISGLQSEDEADYYCAA WDASLNGYVFGTGTKVTVL SEQ ID NO. 153 |
| 14C10 | EVQLLESGGGLIQPGGSLRLSCAASGFTFNSYGMH WVRQAPGKGLEWVAVISYDGSNTYYADSVKGRFT MSRDNSKNTLYLQMNSLRAEDTAVYYCARLQKQV RQLLRNDAFDIWGQGTMVTVSS SEQ ID NO. 154 | QSVLTQPASVSGSPGQSITISCTGTSSDVGG YKYVSWYQQHPGKAPKLMIYDVTKRPSGV SNRFAGSKSGNTASLTISGLQAEDEADYYCS SYTSSSTFMVFGGGTKLTVL SEQ ID NO. 155 |
| 14C11 | QVQLQQSGPGLVKPSQTLSLTCAISGDTVSTNRAA WYWIRQSPSRGLEWLGRTHYRSRWLNDYAPSVKS RITINPDTSKNQFSLQLNSVTPEDTAVYYCARGAAG RAFDIWGQGTLVTVSS SEQ ID NO. 156 | QAGLTQPPSASGTPGQRVTISCSGSSSNIGS NYVYWYQQLPGTAPKLLIYRNNQRPSGVS RFSGSKSGTSASLAISGLRSEDEADYYCAAW DDSLSGWVFGGGTQLTVL SEQ ID NO. 157 |
| 14C3 | QVQLVQSGGGVVQPGRSLRLSCAASGFAFNNYGM HWVRQAPGKGLEWMAVISNDGNRQYYVDSVKGR | DIVMTQSPSSLSASVGDRVTITCRASQTISTY LNWYQQKPGKAPKLLIYDASSLQSGVPSRFT |

Sequence Listing

| | Heavy chain variable domain region | Light chain variable domain region |
|---|---|---|
| | FLISRDNPTRTVYLEMNSLTTDDTGTYYCAKPSSGW FRAFDVWGPGTMVTVSS SEQ ID NO. 158 | GSASGTDFTLTISSLQPEDFATYYCQQSYSIP LTFGGGTKLEIK SEQ ID NO. 159 |
| 14D7 | QVQLVQSGGGVVQPGRSLRLSCAASGFTFSSYGMH WVRQAPGKGLEWVAVISYDGSNKYYADSVKGRFTI SRDNSKNTLYLQMNSLRAEDTAVYYCAKWGRRGA PDYWGQGTLVTVSS SEQ ID NO. 160 | ETTLTQSPGTLSVSPGERATLSCRASQSVSS NLAWYQQKPGQAPRLLIYGASTRATGIPAR FSGSGSGTDFTLTISSLEPEDFAVYYCQQRN NWPLTFGGGTKVEIK SEQ ID NO. 161 |
| 14F11 | EVQLVQSGAEVKKPGASVKVSCKASGSTFTNYYIHW VRQAPGQGLEWMGIINPSGGSIGSPQKFQGRVTM TRDTSTNTVYMELSSLRSEDTAVYYCASRSFGNDGV FDIWGQGTMVTVSS SEQ ID NO. 162 | LPVLTQPRSVSGSPRQSVTISCTGTSSDVGG YNYVSWYQQHPGKAPKLMIYDVSKRPSGV PDRFSGSKSGNTASLTISGLQAEDEAHYYCK SYTTSRTWVFGGGTKLTVL SEQ ID NO. 163 |
| 14F8 | QVQLVESGGGVVQPGRSLRLSCAASGFTFSSYGMH WVRQAPGKGLEWVAVISYDGSNKYYADSVKGRFTI SRDNSKNTLYLQMNSLRAEDTAVYYCAKGNRYFDY WGQGTLVTVSS SEQ ID NO. 164 | QSVLTQPPSASGTPGQRVTISCTGSSSNIGS RYDVHWYQQLPGGAPKLLIYSNTNRPSGVP DRFSASKSGTSASLAISGLQAGDEADYFCQS FDSSLRGYVFGTGTKVTVL SEQ ID NO. 165 |
| 15C9 | EVQLVQSGAEVKKPGASVKVSCKASGYTFTSYGISW VRQAPGQGLEWMGWISAYNGNTNYAQKLQGRVT MTTDTSTSTAYMELRSLRSDDTAVYYCARVRLVGRL GAFDIWGQGTMVTVSS SEQ ID NO. 166 | QSVLTQPPSVSGAPGQRVTISCTGSSSNIGA GYDVHWYQQLPGTAPKLLIYRNSNRPSGVP DRFSGSKSDTSASLTISGLQAEDEADYYCSSY RSGSTPYVFGTGTKLTVL SEQ ID NO. 167 |
| 15D7 | QVQLVQSGAEVKKPGASVKVSCKASGYTFTSYGISW VRQAPGQGLEWMGWISAYNGNTNYAQKLQGRVT MTTDTSTSTAYMELRSLRSDDTAVYYCARGSDYWG QGTLVTVSS SEQ ID NO. 168 | SYELMQPPSASETPGQRVTISCSGSSSNIGS NFVYWYQQLPGMAPKLLIYKNDQRPSGVP DRFSGSKSGTSASLAISGLRSEDEADYYCAAR DDDSLSGSVVFGGGTKVTVL SEQ ID NO. 169 |
| 14D9 | EVQLVESGGGVVQPGRSLRLSCAASGFTFSSYAMH WVRQAPGKGLEWVAVISYDGSNKYYADSVKGRFTI SRDNSKNTLYLQMNSLRAEDTAVYYCARSAWLDS WGQGTLVTVSS SEQ ID NO. 170 | QAGLTQPHSVSGSPGQSVTISCTGTSSDVG SYNHVSWYQQHPGKAPKLMIYDVSKRPSG VSNRFSGSKSGNTASLTISGLQAEDEADYYC SSYTSSSTYVFGTGTKVTVL SEQ ID NO. 171 |
| 15F9 | QVQLVQSGAEVKKPGASVKVSCKASGYTFSSYYMH WVRQAPGQGPEWMGIINPIGGSTTYAQKFQGRVT MTSDTATSTAYMELSGLRSEDTAIYYCARSRKNQW HYGMDVWGEGTTVTVSS SEQ ID NO. 172 | AIQLTQSPSSLSASVGDRVTITCRASQSISSYL NWYQQKPGKAPKLLIYAASSLQSGVPSRFS GSGSGTDFTLTISSLQPEDFATYYCQQSHSV PPTFGQGTKVEIK SEQ ID NO. 173 |
| 15G11 | QVQLVQSGGGVVQPGGSLRLSCAASGFAFNRYGM HWVRQAPGQGLEWVAVISYDGSLKYYADSVKGRF TISRDNSNNTLYLQMNSLSADDTAVYYCAKGGAAL DSWGQGTLVTVSS SEQ ID NO. 174 | DVVMTQSPLSSPVTLGQPASISCRSSQSLVH SDGTTYLSWLQQRPGQPPRLLIYKISNRFSG VPDRFSGSGAGTDFTLKISRVEAEDVGVYYC MQTTQFPPMFGQGTKVEIK SEQ ID NO. 175 |
| 15G7 | QVQLVQSGGGVVQPGRSLRLSCAASGFTFSSYGMH WVRQAPGKGLEWVAVISYDGSNKYYADSVKGRFTI SRDNSKNTLYLQMNSLRAEDTAVYYCAKLSGPTAKF DYWGQGTLVTVSS SEQ ID NO. 176 | QSVLTQPASVSGSPGQSISISCTGTSSDVGG YNYVSWYQQHPGKAPKLMIYDVSNRPSGIS DRFSGSKSGNTASLTISGLQAEDEADYYCSS YRRSSTPWVFGGGTKLTVL SEQ ID NO. 177 |
| 15G9 | QVQLVESGGGVVQPGRSLRLSCAASGFTFSSYGMH WVRQAPGKGLEWVAVISYDGSNKYYADSVKGRFTI SRDNSKNTLYLQMNSLRAEDTAVYYCAKLSGPTAKF DYWGQGTLVTVSS SEQ ID NO. 19 | QSVLTQPPSASGSPGQSVTISCTGTSSDVGG YNYVSWYQQHPGKAPKLKIYDVSKWPSGIS SRFSGSKSGNTASLTISGLQAEDEADYYCSSY TKNKTLIFGGGTKLTVL SEQ ID NO. 178 |
| 15H10 | EVQLVESGGGVVQPGRSLRLSCAASGFTFSDYGMH WVRQAPGKGLEWVAVISYDGSNKYYADSVKGRFTI SRDNSKNTLYLQMNSLRAEDTAVYYCARATFGQGT LVTVSS SEQ ID NO. 179 | QPVLTQPASVSGSPGQSITVSCTGTSSDVG GYNYVSWYQQHPGKAPKLMIYDVTKRPSG VSNRFSGSKSGNTASLTISGLQAEDEADYYC SSYTSSSTPYVFGTGTKVTVL SEQ ID NO. 180 |
| 15H2 | EVQLVESGGGVVQPGRSLRLSCAASGFTFSSYAMH WVRQAPGKGLEWVAVISYDGSKKYYADSVKGRFTI SRDNSKNTLYLQMNSLRAEDTAVYYCARVGIAAAV GMDVWGQGTTVTVSS SEQ ID NO. 181 | DIVMTQTPLSLPVTLGQPASISCRSSQSLVYR DGNTYLNWFQQRPGQSPRRLIYKVSNRDS GVPDRFSGSGSGTDFTLKISRVEAEDVGVYY CMQGTHWPLTFGQGTKVEI SEQ ID NO. 182 |
| 16E3 | QVQLVESGGGVVQPGRSLRLSCAASGFTFSSNGMH WVRQAPGKGLEWVAAISYNGRNQYYADSLKGRFTI SRDNSKNSLYLQMNSLRAEDTAVYYCATPAATLDY WGQGTLVTVSS SEQ ID NO. 183 | QSVLTQPASVSGSPGQSITSCTGTSSDVGG YNYVSWYQHPGKAPKLMIYDVTYRPSGV SNRFSGSKSGNTASLTISGLQAEDEADYYCS SYTSSSTLVFGTGTKVTVL SEQ ID NO. 184 |

| | Heavy chain variable domain region | Light chain variable domain region |
|---|---|---|
| 16A6 | QMQLVQSGGGVVQPGRSLRLSCAASGFTFSSYGM HWVRQAPGKGLEWVAVISYDGSNKYYADSVKGRF TISRDNSKNTLYLQMNSLRAEDTAVYYCARATFGQG TLVTVSS SEQ ID NO. 185 | QSALTQPPSASGTPGQRVTISCSGSRSNIGS NTVNWYQQLPGTAPKLLIHSNTQRPSGVP DRFSGSKSGTSASLAISGLQSEDEADYYCAT WDDSLNGYVFGSGTKVTVL SEQ ID NO. 186 |
| 16A8 | QVQLVESGGGVVQPGRSLRLSCAASGFTFSNYGMH WVRQAPGKGLEWVATISYDGSNNYYAASVKGRFT VSRDNSTLYLQMNSLRAEDTAVYYCAGAIAAAGVW GQGTLVTVSS SEQ ID NO. 187 | LPVLTQPASVSGSPGQSITISCTGTSSDVGGY NYVSWYQQHPGKAPKLMIYDVSNRPSGVS DRFSGSKSGNTASLNISGLQPDDEAEYYCSS YRTKNTLVFGGGTKLTVL SEQ ID NO. 188 |
| 16B1 | EVQLVESGGGVVQPGRSLRLSCAASGFTFSTYGMH WVRQAPGKGLEWVAALAYDGTNKYYAESVKGRFA ISRDNSKNTVFLQMNSLRAEDTAIYYCARDRWLSY WGQGTLVTVSS SEQ ID NO. 189 | QAGLTQPPSLSGSPGQTVTISCTGTSSDVGG YNHVSWYQQHPDKAPQVIIYDVNKRPSEV PDRFSGSKSGNTASLTISGLQPEDEAHYYCT SYAGSHKLLFGGGTKLTVL SEQ ID NO. 190 |
| 16B7 | QVQLVESGAEVKKPGASVKVSCKASGYTFTSYYVH WVRQAPGQGLEWMGIINPSGGTTSYAQKFQGRVT MTRDTSTSTVYMELSSLRSEDTAVYYCVRDRRVVAA TTPSAFDVWGQGTMVTVSS SEQ ID NO. 191 | QSVVTQPPSVSAAPGQRVTISCSGSTSNIGS NYVSWYHQLPGTAPKLLVYHNDKRPSGIPD RFSGSKSGTSATLGITGLQTGDEADYYCGT WDSSLSVWVFGGGTKVTVL SEQ ID NO. 192 |
| 16F8 | EVQLLESGGGLVQPGGSLRLSCAASGFTFSSYGMH WVRQAPGKGLEWVAVISYDGSNKYYADSVKGRFTI SRDNSKNTLYLQLNSLRAEDTAVYYCARGQNLDYW GQGTLVTVSS SEQ ID NO. 193 | QPVLTQPASVSGSPGQSITISCTGTSSDVGG YNYISWYQQHPGKAPKLMIYEVSNRPSGVS NRFSGSKSGNTASLTISGLQAEDEADYYCSS YRSSSTQVFGGGTKLTVL SEQ ID NO. 194 |
| 16F9 | EVQLVESGGEVKKPGASVKLSCKSSGYTFTSYYMH WVRQAPGQGLEWMGIINPSGGSTSSAQKFQGRVT MTRDTSTRTVYMELSSLRSEDTAVYYCARGAPNWN YARTLFDYWGQGTLVTVSS SEQ ID NO. 195 | SYELTQPRSVSGSPGQSVTISCTGTSSDVGG YNSVSWYQQHPGKAPKLMIYDVSKRPSGV PDRFSGSKSGNTASLTISGLQAEDEADYYCS SYSSSTTHVVFGGGTKLTVL SEQ ID NO. 196 |

We claim:

1. A recombinant fully human anti-CXC chemokine receptor 5 (CXCR5) antibody, or an antigen-binding fragment thereof, comprising a heavy chain variable domain comprising complementarity determining regions (CDRs) as set forth in a heavy chain variable domain amino acid sequence selected from the group consisting of SEQ ID NO. 108, SEQ ID NO. 136, SEQ ID NO. 138, SEQ ID NO. 149, and SEQ ID NO. 174; and comprising a light chain variable domain comprising CDRs as set forth in a light chain variable domain amino acid sequence selected from the group consisting of SEQ ID NO. 109, SEQ ID NO. 137, SEQ ID NO. 139, SEQ ID NO. 150, and SEQ ID NO. 175.

2. The recombinant fully human anti-CXCR5 antibody, or antigen binding fragment thereof, of claim 1, wherein the heavy chain variable domain is selected from the group consisting of
   a) a heavy chain variable domain comprising the CDRs as set forth in SEQ ID NO. 108 and comprising an amino acid sequence that is at least 95% identical to SEQ ID NO. 108;
   b) a heavy chain variable domain comprising the CDRs as set forth in SEQ ID NO. 136 and an amino acid sequence that is at least 95% identical to SEQ ID NO. 136;
   c) a heavy chain variable domain comprising the CDRs as set forth in SEQ ID NO. 138 and an amino acid sequence that is at least 95% identical to SEQ ID NO. 138;
   d) a heavy chain variable domain comprising the CDRs as set forth in SEQ ID NO. 149 and an amino acid sequence that is at least 95% identical to SEQ ID NO. 149; and
   e) a heavy chain variable domain comprising the CDRs as set forth in SEQ ID NO. 174 and an amino acid sequence that is at least 95% identical to SEQ ID NO. 174; and wherein the light chain variable domain is selected from the group consisting of a) a light chain variable domain comprising the CDRs as set forth in SEQ ID NO. 109 and an amino acid sequence that is at least 95% identical to SEQ ID NO. 109;

b) a light chain variable domain comprising the CDRs as set forth in SEQ ID NO. 137 and an amino acid sequence that is at least 95% identical to SEQ ID NO. 137;

c) a light chain variable domain comprising the CDRs as set forth in SEQ ID NO. 139 and an amino acid sequence that is at least 95% identical to SEQ ID NO. 139 d) a light chain variable domain comprising the CDRs as set forth in SEQ ID NO. 150 and an amino acid sequence that is at least 95% identical to SEQ ID NO. 150; and e) a light chain variable domain comprising the CDRs as set forth in SEQ ID NO. 175 and an amino acid sequence that is at least 95% identical to SEQ ID NO. 175.

3. The recombinant fully human anti-CXCR5 antibody fragment of claim 2, which is a Fab fragment.

4. The recombinant fully human anti-CXCR5 antibody, or antigen binding-fragment, of claim 1, wherein the heavy chain variable domain comprises an amino acid sequence selected from the group consisting of SEQ ID NO. 108, SEQ ID NO. 136, SEQ ID NO. 138, SEQ ID NO. 149, and SEQ ID NO. 174, and the light chain variable domain comprises an amino acid sequence selected from the group consisting of SEQ ID NO. 109, SEQ ID NO. 137, SEQ ID NO. 139, SEQ ID NO. 150, and SEQ ID NO. 175.

5. The recombinant fully human anti-CXCR5 antibody of claim 1, wherein the antibody is an IgG.

6. The recombinant fully human anti-CXCR5 antibody of claim 5, wherein the antibody is an IgG1 or an IgG4.

7. The recombinant fully human anti-CXCR5 antigen-binding fragment of claim 1, wherein the fragment is a Fab fragment.

8. The recombinant fully human anti-CXCR5 antigen-binding fragment of claim 1, which is a single chain antibody.

9. The recombinant fully human anti-CXCR5 antibody, or antigen-binding fragment thereof, of claim 1, comprising heavy chain/light chain variable domain sequences as set forth in SEQ ID NO. 108/SEQ ID NO. 109.

10. The recombinant fully human anti-CXCR5 antibody, or antigen-binding fragment thereof, of claim 1, comprising heavy chain/light chain variable domain sequences as set forth in SEQ ID NO. 136/SEQ ID NO. 137.

11. The recombinant fully human anti-CXCR5 antibody, or antigen-binding fragment thereof, of claim 1, comprising heavy chain/light chain variable domain sequences as set forth in SEQ ID NO. 138/SEQ ID NO. 139.

12. The recombinant fully human anti-CXCR5 antibody, or antigen-binding fragment thereof, of claim 1, comprising heavy chain/light chain variable domain sequences as set forth in SEQ ID NO. 149/SEQ ID NO. 150.

13. The recombinant fully human anti-CXCR5 antibody, or antigen-binding fragment thereof, of claim 1, comprising heavy chain/light chain variable domain sequences as set forth in SEQ ID NO. 174/SEQ ID NO. 175.

14. The recombinant, fully human antibody, or antigen-binding fragment thereof, of claim 1, wherein the antibody, or antigen-binding fragment thereof, comprises a heavy chain variable domain comprising CDRs as set forth in SEQ ID NO. 108 and comprises a light chain variable domain comprising CDRs as set forth in SEQ ID NO. 109.

15. The recombinant, fully human antibody, or antigen-binding fragment thereof, of claim 1, wherein the antibody, or antigen-binding fragment thereof, comprises a heavy chain variable domain comprising CDRs as set forth in SEQ ID NO. 136 and comprises a light chain variable domain comprising CDRs as set forth in SEQ ID NO. 137.

16. The recombinant, fully human antibody, or antigen-binding fragment thereof, of claim 1, wherein the antibody, or antigen-binding fragment thereof, comprises a heavy chain variable domain comprising CDRs as set forth in SEQ ID NO. 138 and comprises a light chain variable domain comprising CDRs as set forth in SEQ ID NO. 139.

17. The recombinant, fully human antibody, or antigen-binding fragment thereof, of claim 1, wherein the antibody, or antigen-binding fragment thereof, comprises a heavy chain variable domain comprising CDRs as set forth in SEQ ID NO. 149 and comprises a light chain variable domain comprising CDRs as set forth in SEQ ID NO. 150.

18. The recombinant, fully human antibody, or antigen-binding fragment thereof, of claim 1, wherein the antibody, or antigen-binding fragment thereof, comprises a heavy chain variable domain comprising CDRs as set forth in SEQ ID NO. 174 and comprises a light chain variable domain comprising CDRs as set forth in SEQ ID NO. 175.

19. A pharmaceutical composition comprising the recombinant fully human anti-CXCR5 antibody, or antigen-binding fragment thereof, of claim 1, and a pharmaceutically acceptable excipient.

* * * * *